US006927056B2

(12) United States Patent
Todd et al.

(10) Patent No.: US 6,927,056 B2
(45) Date of Patent: Aug. 9, 2005

(54) PROTEASES

(75) Inventors: Stephen Todd, San Francisco, CA (US); Angelo M. Delegeane, Milpitas, CA (US); Ameena R. Gandhi, San Francisco, CA (US); Danniel B. Nguyen, San Jose, CA (US); April J. A. Hafalia, Daly City, CA (US); Liam Kearney, San Francisco, CA (US); Yan Lu, Palo Alto, CA (US); Ernestine A. Lee, Castro Valley, CA (US); Narinder K. Chawla, Union City, CA (US); Debopriya Das, Mountain View, CA (US); Chandra S. Arvizu, San Jose, CA (US); Monique G. Yao, Carmel, IN (US); Deborah A. Kallick, Stanford, CA (US); Vicki S. Elliott, San Jose, CA (US); Li Ding, Creve Coeur, MO (US); Henry Yue, Sunnyvale, CA (US); Roopa M. Reddy, Fremont, CA (US); Dyung Aina M. Lu, San Jose, CA (US); Jayalaxmi Ramkumar, Fremont, CA (US); Junming Yang, San Jose, CA (US); Catherine M. Tribouley, San Francisco, CA (US); Neil Burford, Durham, CT (US); Mariah R. Baughn, San Leandro, CA (US); Preeti G. Lal, Santa Clara, CA (US); Mark L. Borowsky, Redwood City, CA (US); Farrah A. Khan, Des Plaines, IL (US); Rajagopal Gururajan, San Jose, CA (US); Y. Tom Tang, San Jose, CA (US); Janice K. Au-Young, Brisbane, CA (US); Bridget A. Warren, Encinitas, CA (US); Roberto Hernandez, Canterbury (GB); Brendan M. Duggan, Sunnyvale, CA (US)

(73) Assignee: Incyte Corporation, Wilmington, DE (US)

( * ) Notice: Subject to any disclaimer, the term of this patent is extended or adjusted under 35 U.S.C. 154(b) by 29 days.

(21) Appl. No.: 10/363,937
(22) PCT Filed: Sep. 6, 2001
(86) PCT No.: PCT/US01/28161

§ 371 (c)(1),
(2), (4) Date: Mar. 4, 2003

(87) PCT Pub. No.: WO02/20736
PCT Pub. Date: Mar. 14, 2002

(65) Prior Publication Data
US 2004/0053269 A1 Mar. 18, 2004

(51) Int. Cl.$^7$ .......................... C12N 9/64; C12N 1/20; C12N 15/00; C12N 15/63; C07H 21/04
(52) U.S. Cl. ............... 435/226; 435/252.3; 435/252.33; 435/325; 435/320.1; 435/348; 435/419; 435/254.1; 435/254.2; 536/23.2
(58) Field of Search ............... 435/226, 252.3, 435/252.33, 325, 320.1, 348, 419, 254.1, 254.2, 69.1; 536/23.2

(56) References Cited

U.S. PATENT DOCUMENTS 5,710,014 A * 1/1998 Gottesman ................. 435/68.1

OTHER PUBLICATIONS

Barrett et al Handbook of Proteolytic Enzymes Academic Press, New York, NY. 1998 p. 549.*
N_Geneseq Data Base Acc# AVV13921 May 15, 1998 Smith et al. Alignment with SEQ ID No.: 1.*
Whisstock et al Prediction of protein function from protein sequence and structure.Q Rev Biophys. Aug. 2003;36(3):307–40.*
Krem et al Trends Cardiovasc Med. May 2000;10(4):171–6.*

* cited by examiner

Primary Examiner—Tekchand Saidha
Assistant Examiner—Sheridan L. Swope
(74) Attorney, Agent, or Firm—Foley & Lardner LLP

(57) ABSTRACT

The invention provides a human cysteine proteases and polynucleotides which encode those proteases. The invention also provides expression vectors, host cells, antibodies, agonists, and antagonists, as well as methods for diagnosing, treating, or preventing disorders associated with aberrant expression of cysteine proteases.

7 Claims, No Drawings

SEQUENCE LISTING

<160> NUMBER OF SEQ ID NOS: 34

<210> SEQ ID NO 1
<211> LENGTH: 333
<212> TYPE: PRT
<213> ORGANISM: Homo sapiens
<220> FEATURE:
<221> NAME/KEY: misc_feature
<223> OTHER INFORMATION: Incyte ID No: 6930294CD1

<400> SEQUENCE: 1

Met Asn Pro Thr Leu Ile Leu Ala Ala Phe Cys Leu Gly Ile Ala
1               5                   10                  15

Ser Ala Thr Leu Thr Phe Asp His Ser Leu Glu Ala Gln Trp Thr
                20                  25                  30

Lys Trp Lys Ala Met His Asn Arg Leu Tyr Gly Met Asn Glu Glu
                35                  40                  45

Gly Trp Arg Arg Ala Val Trp Glu Lys Asn Met Lys Met Ile Glu
                50                  55                  60

Leu His Asn Gln Glu Tyr Arg Glu Gly Lys His Ser Phe Thr Met
                65                  70                  75

Ala Met Asn Ala Phe Gly Asp Met Thr Ser Glu Glu Phe Arg Gln
                80                  85                  90

Val Met Asn Gly Phe Gln Asn Arg Lys Pro Arg Lys Gly Lys Val
                95                  100                 105

Phe Gln Glu Pro Leu Phe Tyr Glu Ala Pro Arg Ser Val Asp Trp
                110                 115                 120

Arg Glu Lys Gly Tyr Val Thr Pro Val Lys Asn Gln Gly Gln Cys
                125                 130                 135

-continued

```
Gly Ser Cys Trp Ala Phe Ser Ala Thr Gly Ala Leu Glu Gly Gln
                140                 145                 150
Met Phe Arg Lys Thr Gly Arg Leu Ile Ser Leu Ser Glu Gln Asn
            155                 160                 165
Leu Val Asp Cys Ser Gly Pro Gln Gly Asn Glu Gly Cys Asn Gly
        170                 175                 180
Gly Leu Met Asp Tyr Ala Phe Gln Tyr Val Gln Asp Thr Gly Gly
    185                 190                 195
Leu Asp Ser Glu Glu Ser Tyr Pro Tyr Glu Ala Thr Glu Glu Ser
200                 205                 210
Cys Arg Tyr Asn Pro Lys Tyr Ser Ala Ala Asn Asp Thr Gly Phe
            215                 220                 225
Val Asp Ile Pro Ser Gln Glu Lys Asp Leu Ala Lys Ala Val Ala
        230                 235                 240
Thr Val Gly Pro Ile Ser Val Ala Ala Gly Ala Ser His Val Ser
    245                 250                 255
Phe Gln Phe Tyr Lys Lys Gly Ile Tyr Phe Glu Pro Arg Cys Asp
260                 265                 270
Pro Glu Gly Leu Asp His Ala Met Leu Leu Val Gly Tyr Ser Tyr
            275                 280                 285
Glu Gly Ala Asp Ser Asp Asn Asn Lys Tyr Trp Leu Val Lys Asn
        290                 295                 300
Arg Tyr Gly Lys Asn Trp Gly Met Asp Gly Tyr Ile Lys Met Ala
    305                 310                 315
Lys Asp Gln Arg Asn Asn Cys Gly Ile Ala Thr Ala Ala Ser Tyr
320                 325                 330
Pro Thr Val

<210> SEQ ID NO 2
<211> LENGTH: 90
<212> TYPE: PRT
<213> ORGANISM: Homo sapiens
<220> FEATURE:
<221> NAME/KEY: misc_feature
<223> OTHER INFORMATION: Incyte ID No: 7473018CD1

<400> SEQUENCE: 2

Met Ala Asp Gln Leu Arg Lys Lys Arg Ile Phe Ile His
1               5                   10                  15
Ser Val Gly Ala Gly Thr Ile Asn Ala Leu Leu Asp Cys Leu Leu
            20                  25                  30
Glu Asp Glu Val Ile Ser Gln Glu Asp Met Asn Lys Val Arg Asp
        35                  40                  45
Glu Asn Asp Thr Val Met Asp Lys Ala Arg Val Leu Ile Asp Leu
    50                  55                  60
Val Thr Gly Lys Gly Pro Lys Ser Cys Cys Lys Phe Ile Lys His
65                  70                  75
Leu Cys Glu Glu Asp Pro Gln Leu Ala Ser Lys Met Gly Leu His
            80                  85                  90

<210> SEQ ID NO 3
<211> LENGTH: 605
<212> TYPE: PRT
<213> ORGANISM: Homo sapiens
<220> FEATURE:
<221> NAME/KEY: misc_feature
<223> OTHER INFORMATION: Incyte ID No: 7479221CD1
```

<400> SEQUENCE: 3

```
Met Ser Gln Leu Ser Ser Thr Leu Lys Arg Tyr Thr Glu Ser Ala
1               5                   10                  15

Arg Tyr Thr Asp Ala His Tyr Ala Lys Ser Gly Tyr Gly Ala Tyr
                20                  25                  30

Thr Pro Ser Ser Tyr Gly Ala Asn Leu Ala Ala Ser Leu Leu Glu
                35                  40                  45

Lys Glu Lys Leu Gly Phe Lys Pro Val Pro Thr Ser Ser Phe Leu
                50                  55                  60

Thr Arg Pro Arg Thr Tyr Gly Pro Ser Ser Leu Leu Asp Tyr Asp
                65                  70                  75

Arg Gly Arg Pro Leu Leu Arg Pro Asp Ile Thr Gly Gly Lys
                80                  85                  90

Arg Ala Glu Ser Gln Thr Arg Gly Thr Glu Arg Pro Leu Gly Ser
                95                  100                 105

Gly Leu Ser Gly Gly Ser Gly Phe Pro Tyr Gly Val Thr Asn Asn
                110                 115                 120

Cys Leu Ser Tyr Leu Pro Ile Asn Ala Tyr Asp Gln Gly Val Thr
                125                 130                 135

Leu Thr Gln Lys Leu Asp Ser Gln Ser Asp Leu Ala Arg Asp Phe
                140                 145                 150

Ser Ser Leu Arg Thr Ser Asp Ser Tyr Arg Ile Asp Pro Arg Asn
                155                 160                 165

Leu Gly Arg Ser Pro Met Leu Ala Arg Thr Arg Lys Glu Leu Cys
                170                 175                 180

Thr Leu Gln Gly Leu Tyr Gln Thr Ala Ser Cys Pro Glu Tyr Leu
                185                 190                 195

Val Asp Tyr Leu Glu Asn Tyr Gly Arg Lys Gly Ser Ala Ser Gln
                200                 205                 210

Val Pro Ser Gln Ala Pro Pro Ser Arg Val Pro Glu Ile Ile Ser
                215                 220                 225

Pro Thr Tyr Arg Pro Ile Gly Arg Tyr Thr Leu Trp Glu Thr Gly
                230                 235                 240

Lys Gly Gln Ala Pro Gly Pro Ser Arg Ser Ser Pro Gly Arg
                245                 250                 255

Asp Gly Met Asn Ser Lys Ser Ala Gln Gly Leu Ala Gly Leu Arg
                260                 265                 270

Asn Leu Gly Asn Thr Cys Phe Met Asn Ser Ile Leu Gln Cys Leu
                275                 280                 285

Ser Asn Thr Arg Glu Leu Arg Asp Tyr Cys Leu Gln Arg Leu Tyr
                290                 295                 300

Met Arg Asp Leu His His Gly Ser Asn Ala His Thr Ala Leu Val
                305                 310                 315

Glu Glu Phe Ala Lys Leu Ile Gln Thr Ile Trp Thr Ser Ser Pro
                320                 325                 330

Asn Asp Val Val Ser Pro Ser Glu Phe Lys Thr Gln Ile Gln Arg
                335                 340                 345

Tyr Ala Pro Arg Phe Val Gly Tyr Asn Gln Gln Asp Ala Gln Glu
                350                 355                 360

Phe Leu Arg Phe Leu Leu Asp Gly Leu His Asn Glu Val Asn Arg
                365                 370                 375

Val Thr Leu Arg Pro Lys Ser Asn Pro Glu Asn Leu Asp His Leu
```

-continued

```
                380                 385                 390
Pro Asp Asp Glu Lys Gly Arg Gln Met Trp Arg Lys Tyr Leu Glu
            395                 400                 405
Arg Glu Asp Ser Arg Ile Gly Asp Leu Phe Val Gly Gln Leu Lys
        410                 415                 420
Ser Ser Leu Thr Cys Thr Asp Cys Gly Tyr Cys Ser Thr Val Phe
    425                 430                 435
Asp Pro Phe Trp Asp Leu Ser Leu Pro Ile Ala Lys Arg Gly Tyr
440                 445                 450
Pro Glu Val Thr Leu Met Asp Cys Met Arg Leu Phe Thr Lys Glu
            455                 460                 465
Asp Val Leu Asp Gly Asp Glu Lys Pro Thr Cys Cys Arg Cys Arg
        470                 475                 480
Gly Arg Lys Arg Cys Ile Lys Lys Phe Ser Ile Gln Arg Phe Pro
    485                 490                 495
Lys Ile Leu Val Leu His Leu Lys Arg Phe Ser Glu Ser Arg Ile
500                 505                 510
Arg Thr Ser Lys Leu Thr Thr Phe Val Asn Phe Pro Leu Arg Asp
            515                 520                 525
Leu Asp Leu Arg Glu Phe Ala Ser Glu Asn Thr Asn His Ala Val
        530                 535                 540
Tyr Asn Leu Tyr Ala Val Ser Asn His Ser Gly Thr Thr Met Gly
    545                 550                 555
Gly His Tyr Thr Ala Tyr Cys Arg Ser Pro Gly Thr Gly Glu Trp
560                 565                 570
His Thr Phe Asn Asp Ser Ser Val Thr Pro Met Ser Ser Ser Gln
            575                 580                 585
Val Arg Thr Ser Asp Ala Tyr Leu Leu Phe Tyr Glu Leu Ala Ser
        590                 595                 600
Pro Pro Ser Arg Met
            605
```

<210> SEQ ID NO 4
<211> LENGTH: 743
<212> TYPE: PRT
<213> ORGANISM: Homo sapiens
<220> FEATURE:
<221> NAME/KEY: misc_feature
<223> OTHER INFORMATION: Incyte ID No: 2923874CD1

<400> SEQUENCE: 4

```
Met Leu Ile Ser Gly Ile Leu Trp Thr Phe Met His Gln Lys Pro
1               5                   10                  15
Thr Ala Ser His Tyr Leu Gln Val Lys Ser Gln Asp Gly Ile Leu
            20                  25                  30
Ser Pro Gly Lys Gly Leu Glu Asp Thr Asp Val Val Tyr Lys Ser
        35                  40                  45
Glu Asn Gly His Val Ile Lys Leu Asn Ile Glu Thr Asn Ala Thr
    50                  55                  60
Thr Leu Leu Leu Glu Asn Thr Thr Phe Val Thr Phe Lys Ala Ser
65                  70                  75
Arg His Ser Val Ser Pro Asp Leu Lys Tyr Val Leu Leu Ala Tyr
            80                  85                  90
Asp Val Lys Gln Ile Phe His Tyr Ser Tyr Thr Ala Ser Tyr Val
        95                  100                 105
```

-continued

```
Ile Tyr Asn Ile His Thr Arg Glu Val Trp Glu Leu Asn Pro Pro
            110                 115                 120

Glu Val Glu Asp Ser Val Leu Gln Tyr Ala Ala Trp Gly Val Gln
            125                 130                 135

Gly Gln Gln Leu Ile Tyr Ile Phe Glu Asn Asn Ile Tyr Tyr Gln
            140                 145                 150

Pro Asp Ile Lys Ser Ser Ser Leu Arg Leu Thr Ser Ser Gly Lys
            155                 160                 165

Glu Glu Ile Ile Phe Asn Gly Ile Ala Asp Trp Leu Tyr Glu Glu
            170                 175                 180

Glu Leu Leu His Ser His Ile Ala His Trp Trp Ser Pro Asp Gly
            185                 190                 195

Glu Arg Leu Ala Phe Leu Met Ile Asn Asp Ser Leu Val Pro Thr
            200                 205                 210

Met Val Ile Pro Arg Phe Thr Gly Ala Leu Tyr Pro Lys Gly Lys
            215                 220                 225

Gln Tyr Pro Tyr Pro Lys Ala Gly Gln Val Asn Pro Thr Ile Lys
            230                 235                 240

Leu Tyr Val Val Asn Leu Tyr Gly Pro Thr His Thr Leu Glu Leu
            245                 250                 255

Met Pro Pro Asp Ser Phe Lys Ser Arg Glu Tyr Tyr Ile Thr Met
            260                 265                 270

Val Lys Trp Val Ser Asn Thr Lys Thr Val Arg Trp Leu Asn
            275                 280                 285

Arg Pro Gln Asn Ile Ser Ile Leu Thr Val Cys Glu Thr Thr Thr
            290                 295                 300

Gly Ala Cys Ser Lys Lys Tyr Glu Met Thr Ser Asp Thr Trp Leu
            305                 310                 315

Ser Gln Gln Asn Glu Glu Pro Val Phe Ser Arg Asp Gly Ser Lys
            320                 325                 330

Phe Phe Met Thr Val Pro Val Lys Gln Gly Gly Arg Gly Glu Phe
            335                 340                 345

His His Ile Ala Met Phe Leu Ile Gln Ser Lys Ser Glu Gln Ile
            350                 355                 360

Thr Val Arg His Leu Thr Ser Gly Asn Trp Glu Val Ile Lys Ile
            365                 370                 375

Leu Ala Tyr Asp Glu Thr Thr Gln Lys Ile Tyr Phe Leu Ser Thr
            380                 385                 390

Glu Ser Ser Pro Arg Gly Arg Gln Leu Tyr Ser Ala Ser Thr Glu
            395                 400                 405

Gly Leu Leu Asn Arg Gln Cys Ile Ser Cys Asn Phe Met Lys Glu
            410                 415                 420

Gln Cys Thr Tyr Phe Asp Ala Ser Phe Ser Pro Met Asn Gln His
            425                 430                 435

Phe Leu Leu Phe Cys Glu Gly Pro Arg Val Pro Val Val Ser Leu
            440                 445                 450

His Ser Thr Asp Asn Pro Ala Lys Tyr Phe Ile Leu Glu Ser Asn
            455                 460                 465

Ser Met Leu Lys Glu Ala Ile Leu Lys Lys Ile Gly Lys Pro
            470                 475                 480

Glu Ile Lys Ile Leu His Ile Asp Asp Tyr Glu Leu Pro Leu Gln
            485                 490                 495

Leu Ser Leu Pro Lys Asp Phe Met Asp Arg Asn Gln Tyr Ala Leu
```

-continued

```
                500                 505                 510
Leu Leu Ile Met Asp Glu Glu Pro Gly Gly Gln Leu Val Thr Asp
            515                 520                 525
Lys Phe His Ile Asp Trp Asp Ser Val Leu Ile Asp Met Asp Asn
        530                 535                 540
Val Ile Val Ala Arg Phe Asp Gly Arg Gly Ser Gly Phe Gln Gly
    545                 550                 555
Leu Lys Ile Leu Gln Glu Ile His Arg Arg Leu Gly Ser Val Glu
560                 565                 570
Val Lys Asp Gln Ile Thr Ala Val Lys Phe Leu Leu Lys Leu Pro
            575                 580                 585
Tyr Ile Asp Ser Lys Arg Leu Ser Ile Phe Gly Lys Gly Tyr Gly
        590                 595                 600
Gly Tyr Ile Ala Ser Met Ile Leu Lys Ser Asp Glu Lys Leu Phe
    605                 610                 615
Lys Cys Gly Ser Val Val Ala Pro Ile Thr Asp Leu Lys Leu Tyr
620                 625                 630
Ala Ser Ala Phe Ser Glu Arg Tyr Leu Gly Met Pro Ser Lys Glu
            635                 640                 645
Glu Ser Thr Tyr Gln Ala Ala Ser Val Leu His Asn Val His Gly
        650                 655                 660
Leu Lys Glu Glu Asn Ile Leu Ile Ile His Gly Thr Ala Asp Thr
    665                 670                 675
Lys Val His Phe Gln His Ser Ala Glu Leu Ile Lys His Leu Ile
680                 685                 690
Lys Ala Gly Val Asn Tyr Thr Met Gln Val Tyr Pro Asp Glu Gly
            695                 700                 705
His Asn Val Ser Glu Lys Ser Lys Tyr His Leu Tyr Ser Thr Ile
        710                 715                 720
Leu Lys Phe Phe Ser Asp Cys Leu Lys Glu Glu Ile Ser Val Leu
    725                 730                 735
Pro Gln Glu Pro Glu Glu Asp Glu
            740

<210> SEQ ID NO 5
<211> LENGTH: 650
<212> TYPE: PRT
<213> ORGANISM: Homo sapiens
<220> FEATURE:
<221> NAME/KEY: misc_feature
<223> OTHER INFORMATION: Incyte ID No: 55122335CD1

<400> SEQUENCE: 5

Met Ala Ser Gly Glu His Ser Pro Gly Ser Gly Ala Ala Arg Arg
1               5                   10                  15
Pro Leu His Ser Ala Gln Ala Val Asp Val Ala Ser Ala Ser Asn
            20                  25                  30
Phe Arg Ala Phe Glu Leu Leu His Leu His Leu Asp Leu Arg Ala
        35                  40                  45
Glu Phe Gly Pro Pro Gly Pro Gly Ala Gly Ser Arg Gly Leu Ser
    50                  55                  60
Gly Thr Ala Val Leu Asp Leu Arg Cys Leu Glu Pro Glu Gly Ala
65                  70                  75
Ala Glu Leu Arg Leu Asp Ser His Pro Cys Leu Glu Val Thr Ala
            80                  85                  90
```

-continued

```
Ala Ala Leu Arg Arg Glu Arg Pro Gly Ser Glu Pro Pro Ala
         95                 100                 105

Glu Pro Val Ser Phe Tyr Thr Gln Pro Phe Ser His Tyr Gly Gln
             110                 115                 120

Ala Leu Cys Val Ser Phe Pro Gln Pro Cys Arg Ala Ala Glu Arg
             125                 130                 135

Leu Gln Val Leu Leu Thr Tyr Arg Val Gly Glu Gly Pro Gly Val
             140                 145                 150

Cys Trp Leu Ala Pro Glu Gln Thr Ala Gly Lys Lys Pro Phe
             155                 160                 165

Val Tyr Thr Gln Gly Gln Ala Val Leu Asn Arg Ala Phe Phe Pro
             170                 175                 180

Cys Phe Asp Thr Pro Ala Val Lys Tyr Lys Tyr Ser Ala Leu Ile
             185                 190                 195

Glu Val Pro Asp Gly Phe Thr Ala Val Met Ser Ala Ser Thr Trp
             200                 205                 210

Glu Lys Arg Gly Pro Asn Lys Phe Phe Gln Met Cys Gln Pro
             215                 220                 225

Ile Pro Ser Tyr Leu Ile Ala Leu Ala Ile Gly Asp Leu Val Ser
             230                 235                 240

Ala Glu Val Gly Pro Arg Ser Arg Val Trp Ala Glu Pro Cys Leu
             245                 250                 255

Ile Asp Ala Ala Lys Glu Glu Tyr Asn Gly Val Ile Glu Phe
             260                 265                 270

Leu Ala Thr Gly Glu Lys Leu Phe Gly Pro Tyr Val Trp Gly Arg
             275                 280                 285

Tyr Asp Leu Leu Phe Met Pro Pro Ser Phe Pro Phe Gly Gly Met
             290                 295                 300

Glu Asn Pro Cys Leu Thr Phe Val Thr Pro Cys Leu Leu Ala Gly
             305                 310                 315

Asp Arg Ser Leu Ala Asp Val Ile Ile His Glu Ile Ser His Ser
             320                 325                 330

Trp Phe Gly Asn Leu Val Thr Asn Ala Asn Trp Gly Glu Phe Trp
             335                 340                 345

Leu Asn Glu Gly Phe Thr Met Tyr Ala Gln Arg Arg Ile Ser Thr
             350                 355                 360

Ile Leu Phe Gly Ala Ala Tyr Thr Cys Leu Glu Ala Ala Thr Gly
             365                 370                 375

Arg Ala Leu Leu Arg Gln His Met Asp Ile Thr Gly Glu Glu Asn
             380                 385                 390

Pro Leu Asn Lys Leu Arg Val Lys Ile Glu Pro Gly Val Asp Pro
             395                 400                 405

Asp Asp Thr Tyr Asn Glu Thr Pro Tyr Glu Lys Gly Phe Cys Phe
             410                 415                 420

Val Ser Tyr Leu Ala His Leu Val Gly Asp Gln Asp Gln Phe Asp
             425                 430                 435

Ser Phe Leu Lys Ala Tyr Val His Glu Phe Lys Phe Arg Ser Ile
             440                 445                 450

Leu Ala Asp Asp Phe Leu Asp Phe Tyr Leu Glu Tyr Phe Pro Glu
             455                 460                 465

Leu Lys Lys Lys Arg Val Asp Ile Ile Pro Gly Phe Glu Phe Asp
             470                 475                 480

Arg Trp Leu Asn Thr Pro Gly Trp Pro Pro Tyr Leu Pro Asp Leu
```

-continued

```
                485                 490                 495
Ser Pro Gly Asp Ser Leu Met Lys Pro Ala Glu Glu Leu Ala Gln
                500                 505                 510
Leu Trp Ala Ala Glu Leu Asp Met Lys Ala Ile Glu Ala Val
            515                 520                 525
Ala Ile Ser Pro Trp Lys Thr Tyr Gln Leu Val Tyr Phe Leu Asp
                530                 535                 540
Lys Ile Leu Gln Lys Ser Pro Leu Pro Gly Asn Val Lys Lys
            545                 550                 555
Leu Gly Asp Thr Tyr Pro Ser Ile Ser Asn Ala Arg Asn Ala Glu
                560                 565                 570
Leu Arg Leu Arg Trp Gly Gln Ile Ile Leu Lys Asn Asp His Gln
            575                 580                 585
Glu Asp Phe Trp Lys Val Lys Glu Phe Leu His Asn Gln Gly Lys
                590                 595                 600
Gln Lys Tyr Thr Leu Pro Leu Tyr His Ala Met Met Gly Gly Ser
            605                 610                 615
Glu Val Ala Gln Thr Leu Ala Lys Glu Thr Phe Ala Ser Thr Ala
                620                 625                 630
Ser Gln Leu His Ser Asn Val Val Asn Tyr Val Gln Gln Ile Val
            635                 640                 645
Ala Pro Lys Gly Ser
            650

<210> SEQ ID NO 6
<211> LENGTH: 932
<212> TYPE: PRT
<213> ORGANISM: Homo sapiens
<220> FEATURE:
<221> NAME/KEY: misc_feature
<223> OTHER INFORMATION: Incyte ID No: 7473550CD1

<400> SEQUENCE: 6

Met Gly Leu Leu Ala Ser Ala Gly Leu Leu Leu Leu Val Ile
1               5                   10                  15
Gly His Pro Arg Ser Leu Gly Leu Lys Cys Gly Ile Arg Met Val
            20                  25                  30
Asn Met Lys Ser Lys Glu Pro Ala Val Gly Ser Arg Phe Phe Ser
            35                  40                  45
Arg Ile Ser Ser Trp Arg Asn Ser Thr Val Thr Gly His Pro Trp
            50                  55                  60
Gln Val Tyr Leu Lys Ser Asp Glu His His Phe Cys Gly Gly Ser
            65                  70                  75
Leu Ile Gln Glu Asp Arg Val Val Thr Ala Ala His Cys Leu His
            80                  85                  90
Ser Leu Ser Glu Lys Gln Leu Lys Asn Ile Thr Val Thr Ser Gly
            95                  100                 105
Glu Tyr Ser Leu Phe Gln Lys Asp Lys Gln Glu Gln Asn Ile Pro
            110                 115                 120
Val Ser Lys Ile Ile Thr His Pro Glu Tyr Asn Ser Arg Glu Tyr
            125                 130                 135
Met Ser Pro Asp Ile Ala Leu Leu Tyr Leu Lys His Lys Val Lys
            140                 145                 150
Phe Gly Asn Ala Val Gln Pro Ile Cys Leu Pro Asp Ser Asp Asp
            155                 160                 165
```

-continued

```
Lys Val Glu Pro Gly Ile Leu Cys Leu Ser Gly Trp Gly Lys
            170                 175                 180

Ile Ser Lys Thr Ser Glu Tyr Ser Asn Val Leu Gln Glu Met Glu
                185                 190                 195

Leu Pro Ile Met Asp Asp Arg Ala Cys Asn Thr Val Leu Lys Ser
            200                 205                 210

Met Asn Leu Pro Pro Leu Gly Arg Thr Met Leu Cys Ala Gly Phe
            215                 220                 225

Pro Asp Trp Gly Met Asp Ala Cys Gln Gly Asp Ser Gly Gly Pro
            230                 235                 240

Leu Val Cys Arg Arg Gly Gly Gly Ile Trp Ile Leu Ala Gly Ile
            245                 250                 255

Thr Ser Trp Val Ala Gly Cys Ala Gly Gly Ser Val Pro Val Arg
            260                 265                 270

Asn Asn His Val Lys Ala Ser Leu Gly Ile Phe Ser Lys Val Ser
            275                 280                 285

Glu Leu Met Asp Phe Ile Thr Gln Asn Leu Phe Thr Gly Leu Asp
            290                 295                 300

Arg Gly Gln Pro Leu Ser Lys Val Gly Ser Arg Tyr Ile Thr Lys
            305                 310                 315

Ala Leu Ser Ser Val Gln Glu Val Asn Gly Ser Gln Arg Asp Lys
            320                 325                 330

Ile Ile Leu Ile Lys Phe Thr Ser Leu Asp Met Glu Lys Gln Val
            335                 340                 345

Gly Cys Asp His Asp Tyr Val Ser Leu Arg Ser Ser Ser Gly Val
            350                 355                 360

Leu Phe Ser Lys Val Cys Gly Lys Ile Leu Pro Ser Pro Leu Leu
            365                 370                 375

Ala Glu Thr Ser Glu Ala Met Val Pro Phe Val Ser Asp Thr Glu
            380                 385                 390

Asp Ser Gly Ser Gly Phe Glu Leu Thr Val Thr Ala Val Gln Lys
            395                 400                 405

Ser Glu Ala Gly Ser Gly Cys Gly Ser Leu Ala Ile Leu Val Glu
            410                 415                 420

Glu Gly Thr Asn His Ser Ala Lys Tyr Pro Asp Leu Tyr Pro Ser
            425                 430                 435

Asn Thr Arg Cys His Trp Phe Ile Cys Ala Pro Glu Lys His Ile
            440                 445                 450

Ile Lys Leu Thr Phe Glu Asp Phe Ala Val Lys Phe Ser Pro Asn
            455                 460                 465

Cys Ile Tyr Asp Ala Val Val Ile Tyr Gly Asp Ser Glu Glu Lys
            470                 475                 480

His Lys Leu Ala Lys Leu Cys Gly Met Leu Thr Ile Thr Ser Ile
            485                 490                 495

Phe Ser Ser Ser Asn Met Thr Val Ile Tyr Phe Lys Ser Asp Gly
            500                 505                 510

Lys Asn Arg Leu Gln Gly Phe Lys Ala Arg Phe Thr Ile Leu Pro
            515                 520                 525

Ser Glu Ser Leu Asn Lys Phe Glu Pro Lys Leu Pro Pro Gln Asn
            530                 535                 540

Asn Pro Val Ser Thr Val Lys Ala Ile Leu His Asp Val Cys Gly
            545                 550                 555

Ile Pro Pro Phe Ser Pro Gln Trp Leu Ser Arg Arg Ile Ala Gly
```

-continued

```
                    560                 565                 570
Gly Glu Glu Ala Cys Pro His Cys Trp Pro Trp Gln Val Gly Leu
                575                 580                 585
Arg Phe Leu Gly Asp Tyr Gln Cys Gly Gly Ala Ile Ile Asn Pro
                590                 595                 600
Val Trp Ile Leu Thr Ala Ala His Cys Val Gln Leu Lys Asn Asn
                605                 610                 615
Pro Leu Ser Trp Thr Ile Ile Ala Gly Asp His Asp Arg Asn Leu
                620                 625                 630
Lys Glu Ser Thr Glu Gln Val Arg Arg Ala Lys His Ile Ile Val
                635                 640                 645
His Glu Asp Phe Asn Thr Leu Ser Tyr Asp Ser Asp Ile Ala Leu
                650                 655                 660
Ile Gln Leu Ser Ser Pro Leu Glu Tyr Asn Ser Val Val Arg Pro
                665                 670                 675
Val Cys Leu Pro His Ser Ala Glu Pro Leu Phe Ser Ser Glu Ile
                680                 685                 690
Cys Ala Val Thr Gly Trp Gly Ser Ile Ser Ala Glu Leu Ser Leu
                695                 700                 705
Asn Val Ser Ser Leu Asp Gly Gly Leu Ala Ser Arg Leu Gln Gln
                710                 715                 720
Ile Gln Val His Val Leu Glu Arg Glu Val Cys Glu His Thr Tyr
                725                 730                 735
Tyr Ser Ala His Pro Gly Gly Ile Thr Glu Lys Met Ile Cys Ala
                740                 745                 750
Gly Phe Ala Ala Ser Gly Glu Lys Asp Phe Cys Gln Gly Asp Ser
                755                 760                 765
Gly Gly Pro Leu Val Cys Arg His Glu Asn Gly Pro Phe Val Leu
                770                 775                 780
Tyr Gly Ile Val Ser Trp Gly Ala Gly Cys Val Gln Pro Trp Lys
                785                 790                 795
Pro Gly Val Phe Ala Arg Val Met Ile Phe Leu Asp Trp Ile Gln
                800                 805                 810
Ser Lys Ile Asn Gly Lys Leu Phe Ser Asn Val Ile Lys Thr Ile
                815                 820                 825
Thr Ser Phe Phe Arg Val Gly Leu Gly Thr Val Ser Cys Cys Ser
                830                 835                 840
Glu Ala Glu Leu Glu Lys Pro Arg Gly Phe Phe Pro Thr Pro Arg
                845                 850                 855
Tyr Leu Leu Asp Tyr Arg Gly Arg Leu Glu Cys Ser Trp Val Leu
                860                 865                 870
Arg Val Ser Ala Ser Ser Met Ala Lys Phe Thr Ile Glu Tyr Leu
                875                 880                 885
Ser Leu Leu Gly Ser Pro Val Cys Gln Asp Ser Val Leu Ile Ile
                890                 895                 900
Tyr Glu Glu Arg His Ser Lys Arg Lys Thr Ala Gly Asn Pro Ser
                905                 910                 915
Trp His Leu Pro Met Glu Ile Ser Ser Pro Phe Lys Ser His His
                920                 925                 930
Ser Ala
```

<210> SEQ ID NO 7
<211> LENGTH: 990

-continued

```
<212> TYPE: PRT
<213> ORGANISM: Homo sapiens
<220> FEATURE:
<221> NAME/KEY: misc_feature
<223> OTHER INFORMATION: Incyte ID No: 7478108CD1

<400> SEQUENCE: 7

Met Gly Pro Pro Ser Ser Ser Gly Phe Tyr Val Ser Arg Ala Val
1               5                   10                  15

Ala Leu Leu Leu Ala Gly Leu Val Ala Ala Leu Leu Leu Ala Leu
                20                  25                  30

Ala Val Leu Ala Ala Leu Tyr Gly His Cys Glu Arg Val Pro Pro
                35                  40                  45

Ser Glu Leu Pro Gly Leu Arg Asp Ser Glu Ala Glu Ser Ser Pro
                50                  55                  60

Pro Leu Arg Gln Lys Pro Thr Pro Thr Pro Lys Pro Ser Ser Ala
                65                  70                  75

Arg Glu Leu Ala Val Thr Thr Thr Pro Ser Asn Trp Arg Pro Pro
                80                  85                  90

Gly Pro Trp Asp Gln Leu Arg Leu Pro Pro Trp Leu Val Pro Leu
                95                  100                 105

His Tyr Asp Leu Glu Leu Trp Pro Gln Leu Arg Pro Asp Glu Leu
                110                 115                 120

Pro Ala Gly Ser Leu Pro Phe Thr Gly Arg Val Asn Ile Thr Val
                125                 130                 135

Arg Cys Thr Val Ala Thr Ser Arg Leu Leu His Ser Leu Phe
                140                 145                 150

Gln Asp Cys Glu Arg Ala Glu Val Arg Gly Pro Leu Ser Pro Gly
                155                 160                 165

Thr Gly Asn Ala Thr Val Gly Arg Val Pro Val Asp Val Trp
                170                 175                 180

Phe Ala Leu Asp Thr Glu Tyr Met Val Leu Glu Leu Ser Glu Pro
                185                 190                 195

Leu Lys Pro Gly Ser Ser Tyr Glu Leu Gln Leu Ser Phe Ser Gly
                200                 205                 210

Leu Val Lys Glu Asp Leu Arg Glu Gly Leu Phe Leu Asn Val Tyr
                215                 220                 225

Thr Asp Gln Gly Glu Arg Arg Ala Leu Leu Ala Ser Gln Leu Glu
                230                 235                 240

Pro Thr Phe Ala Arg Tyr Val Phe Pro Cys Phe Asp Glu Pro Ala
                245                 250                 255

Leu Lys Ala Thr Phe Asn Ile Thr Met Ile His His Pro Ser Tyr
                260                 265                 270

Val Ala Leu Ser Asn Met Pro Lys Leu Gly Gln Ser Glu Lys Glu
                275                 280                 285

Asp Val Asn Gly Ser Lys Trp Thr Val Thr Thr Phe Ser Thr Thr
                290                 295                 300

Pro His Met Pro Thr Tyr Leu Val Ala Phe Val Ile Cys Asp Tyr
                305                 310                 315

Asp His Val Asn Arg Thr Glu Arg Gly Lys Glu Ile Arg Ile Trp
                320                 325                 330

Ala Arg Lys Asp Ala Ile Ala Asn Gly Ser Ala Asp Phe Ala Leu
                335                 340                 345

Asn Ile Thr Gly Pro Ile Phe Ser Phe Leu Glu Asp Leu Phe Asn
                350                 355                 360
```

-continued

```
Ile Ser Tyr Ser Leu Pro Lys Thr Asp Ile Ile Ala Leu Pro Ser
            365                 370                 375
Phe Asp Asn His Ala Met Glu Asn Trp Gly Leu Met Ile Phe Asp
            380                 385                 390
Glu Ser Gly Leu Leu Leu Glu Pro Lys Asp Gln Leu Thr Glu Lys
            395                 400                 405
Lys Thr Leu Ile Ser Tyr Val Ser His Glu Ile Gly His Gln
            410                 415                 420
Trp Phe Gly Asn Leu Val Thr Met Asn Trp Trp Asn Asn Ile Trp
            425                 430                 435
Leu Asn Glu Gly Phe Ala Ser Tyr Phe Glu Phe Glu Val Ile Asn
            440                 445                 450
Tyr Phe Asn Pro Lys Leu Pro Arg Asn Glu Ile Phe Phe Ser Asn
            455                 460                 465
Ile Leu His Asn Ile Leu Arg Glu Asp His Ala Leu Val Thr Arg
            470                 475                 480
Ala Val Ala Met Lys Val Glu Asn Phe Lys Thr Ser Glu Ile Gln
            485                 490                 495
Glu Leu Phe Asp Ile Phe Thr Tyr Ser Lys Gly Ala Ser Met Ala
            500                 505                 510
Arg Met Leu Ser Cys Phe Leu Asn Glu His Leu Phe Val Ser Ala
            515                 520                 525
Leu Lys Ser Tyr Leu Lys Thr Phe Ser Tyr Ser Asn Ala Glu Gln
            530                 535                 540
Asp Asp Leu Trp Arg His Phe Gln Met Ala Ile Asp Asp Gln Ser
            545                 550                 555
Thr Val Ile Leu Pro Ala Thr Ile Lys Asn Ile Met Asp Ser Trp
            560                 565                 570
Thr His Gln Ser Gly Phe Pro Val Ile Thr Leu Asn Val Ser Thr
            575                 580                 585
Gly Val Met Lys Gln Glu Pro Phe Tyr Leu Glu Asn Ile Lys Asn
            590                 595                 600
Arg Thr Leu Leu Thr Ser Asn Asp Thr Trp Ile Val Pro Ile Leu
            605                 610                 615
Trp Ile Lys Asn Gly Thr Thr Gln Pro Leu Val Trp Leu Asp Gln
            620                 625                 630
Ser Ser Lys Val Phe Pro Glu Met Gln Val Ser Asp Ser Asp His
            635                 640                 645
Asp Trp Val Ile Leu Asn Leu Asn Met Thr Gly Tyr Tyr Arg Val
            650                 655                 660
Asn Tyr Asp Lys Leu Gly Trp Lys Lys Leu Asn Gln Gln Leu Glu
            665                 670                 675
Lys Asp Pro Lys Ala Ile Pro Val Ile His Arg Leu Gln Phe Ile
            680                 685                 690
Asp Asp Ala Phe Ser Leu Ser Lys Asn Asn Tyr Ile Glu Ile Glu
            695                 700                 705
Thr Ala Leu Glu Leu Thr Lys Tyr Leu Ala Glu Glu Asp Glu Ile
            710                 715                 720
Ile Val Trp His Thr Val Leu Val Asn Leu Val Thr Arg Asp Leu
            725                 730                 735
Val Ser Glu Val Asn Ile Tyr Asp Ile Tyr Ser Leu Leu Lys Arg
            740                 745                 750
```

-continued

```
Tyr Leu Leu Lys Arg Leu Asn Leu Ile Trp Asn Ile Tyr Ser Thr
            755                 760                 765

Ile Ile Arg Glu Asn Val Leu Ala Leu Gln Asp Asp Tyr Leu Ala
            770                 775                 780

Leu Ile Ser Leu Glu Lys Leu Phe Val Thr Ala Cys Trp Leu Gly
            785                 790                 795

Leu Glu Asp Cys Leu Gln Leu Ser Lys Glu Leu Phe Ala Lys Trp
            800                 805                 810

Val Asp His Pro Glu Asn Glu Ile Pro Tyr Pro Ile Lys Asp Val
            815                 820                 825

Val Leu Cys Tyr Gly Ile Ala Leu Gly Ser Asp Lys Glu Trp Asp
            830                 835                 840

Ile Leu Leu Asn Thr Tyr Thr Asn Thr Thr Asn Lys Glu Glu Lys
            845                 850                 855

Ile Gln Leu Ala Tyr Ala Met Ser Cys Ser Lys Asp Pro Trp Ile
            860                 865                 870

Leu Asn Arg Tyr Met Glu Tyr Ala Ile Ser Thr Ser Pro Phe Thr
            875                 880                 885

Ser Asn Glu Thr Asn Ile Ile Glu Val Val Ala Ser Ser Glu Val
            890                 895                 900

Gly Arg Tyr Val Ala Lys Asp Phe Leu Val Asn Asn Trp Gln Ala
            905                 910                 915

Val Ser Lys Arg Tyr Gly Thr Gln Ser Leu Ile Asn Leu Ile Tyr
            920                 925                 930

Thr Ile Gly Arg Thr Val Thr Thr Asp Leu Gln Ile Val Glu Leu
            935                 940                 945

Gln Gln Phe Phe Ser Asn Met Leu Glu Glu His Gln Arg Ile Arg
            950                 955                 960

Val His Ala Asn Leu Gln Thr Ile Lys Asn Glu Asn Leu Lys Asn
            965                 970                 975

Lys Lys Leu Ser Ala Arg Ile Ala Ala Trp Leu Arg Arg Asn Thr
            980                 985                 990

<210> SEQ ID NO 8
<211> LENGTH: 396
<212> TYPE: PRT
<213> ORGANISM: Homo sapiens
<220> FEATURE:
<221> NAME/KEY: misc_feature
<223> OTHER INFORMATION: Incyte ID No: 7482021CD1

<400> SEQUENCE: 8

Met Arg Thr Ser Tyr Thr Val Thr Leu Pro Glu Asp Pro Pro Ala
1               5                   10                  15

Ala Pro Phe Pro Ala Leu Ala Lys Glu Leu Arg Pro Arg Ser Pro
                20                  25                  30

Leu Ser Pro Ser Leu Leu Ser Thr Phe Val Gly Leu Leu Leu
                35                  40                  45

Asn Lys Ala Lys Asn Ser Lys Ser Ala Gln Gly Leu Ala Gly Leu
            50                  55                  60

Arg Asn Leu Gly Asn Thr Cys Phe Met Asn Ser Ile Leu Gln Cys
65                  70                  75

Leu Ser Asn Thr Arg Glu Leu Arg Asp Tyr Cys Leu Gln Arg Leu
            80                  85                  90

Tyr Met Arg Asp Leu His His Gly Ser Asn Ala His Thr Ala Leu
            95                  100                 105
```

```
Val Glu Glu Phe Ala Lys Leu Ile Gln Thr Ile Trp Thr Ser Ser
            110                 115                 120

Pro Asn Asp Val Val Ser Pro Ser Glu Phe Lys Thr Gln Ile Gln
            125                 130                 135

Arg Tyr Ala Pro Arg Phe Val Gly Tyr Asn Gln Gln Asp Ala Gln
            140                 145                 150

Glu Phe Leu Arg Phe Leu Leu Asp Gly Leu His Asn Glu Val Asn
            155                 160                 165

Arg Val Thr Leu Arg Pro Lys Ser Asn Pro Glu Asn Leu Asp His
            170                 175                 180

Leu Pro Asp Asp Glu Lys Gly Arg Gln Met Trp Arg Lys Tyr Leu
            185                 190                 195

Glu Arg Glu Asp Ser Arg Ile Gly Asp Leu Phe Val Gly Gln Leu
            200                 205                 210

Lys Ser Ser Leu Thr Cys Thr Asp Cys Gly Tyr Cys Ser Thr Val
            215                 220                 225

Phe Asp Pro Phe Trp Asp Leu Ser Leu Pro Ile Ala Lys Arg Gly
            230                 235                 240

Tyr Pro Glu Val Thr Leu Met Asp Cys Met Arg Leu Phe Thr Lys
            245                 250                 255

Glu Asp Val Leu Asp Gly Asp Glu Lys Pro Thr Cys Cys Arg Cys
            260                 265                 270

Arg Gly Arg Lys Arg Cys Ile Lys Lys Phe Ser Ile Gln Arg Phe
            275                 280                 285

Pro Lys Ile Leu Val Leu His Leu Lys Arg Phe Ser Glu Ser Arg
            290                 295                 300

Ile Arg Thr Ser Lys Leu Thr Thr Phe Val Asn Phe Pro Leu Arg
            305                 310                 315

Asp Leu Asp Leu Arg Glu Phe Ala Ser Glu Asn Thr Asn His Ala
            320                 325                 330

Val Tyr Asn Leu Tyr Ala Val Ser Asn His Ser Gly Thr Thr Met
            335                 340                 345

Gly Gly His Tyr Thr Ala Tyr Cys Arg Ser Pro Gly Thr Gly Glu
            350                 355                 360

Trp His Thr Phe Asn Asp Ser Ser Val Thr Pro Met Ser Ser Ser
            365                 370                 375

Gln Val Arg Thr Ser Asp Ala Tyr Leu Leu Phe Tyr Glu Leu Ala
            380                 385                 390

Ser Pro Pro Ser Arg Met
            395

<210> SEQ ID NO 9
<211> LENGTH: 250
<212> TYPE: PRT
<213> ORGANISM: Homo sapiens
<220> FEATURE:
<221> NAME/KEY: misc_feature
<223> OTHER INFORMATION: Incyte ID No: 7482145CD1

<400> SEQUENCE: 9

Met Ala Ser Arg Tyr Asp Arg Ala Ile Thr Val Phe Ser Pro Asp
1               5                   10                  15

Gly His Leu Phe Gln Val Glu Tyr Ala Gln Glu Ala Val Lys Lys
                20                  25                  30

Gly Ser Thr Ala Val Gly Ile Arg Gly Thr Asn Ile Val Val Leu
```

-continued

```
                 35                  40                  45
Gly Val Glu Lys Lys Ser Val Ala Lys Leu Gln Asp Glu Arg Thr
             50                  55                  60
Val Arg Lys Ile Cys Ala Leu Asp Asp His Val Cys Met Ala Phe
         65                  70                  75
Ala Gly Leu Thr Ala Asp Ala Arg Val Val Ile Asn Arg Ala Arg
     80                  85                  90
Val Glu Cys Gln Ser His Lys Leu Thr Val Glu Asp Pro Val Thr
 95                 100                 105
Val Glu Tyr Ile Thr Arg Phe Ile Ala Thr Leu Lys Gln Lys Tyr
            110                 115                 120
Thr Gln Ser Asn Gly Arg Arg Pro Phe Gly Ile Ser Ala Leu Ile
        125                 130                 135
Val Gly Phe Asp Asp Gly Ile Ser Arg Leu Tyr Gln Thr Asp
    140                 145                 150
Pro Ser Gly Thr Tyr His Ala Trp Lys Ala Asn Ala Ile Gly Arg
155                 160                 165
Ser Ala Lys Thr Val Arg Glu Phe Leu Glu Lys Asn Tyr Thr Glu
            170                 175                 180
Asp Ala Ile Ala Ser Asp Ser Glu Ala Ile Lys Leu Ala Ile Lys
        185                 190                 195
Ala Leu Leu Glu Val Val Gln Ser Gly Gly Lys Asn Ile Glu Leu
    200                 205                 210
Ala Ile Ile Arg Arg Asn Gln Pro Leu Lys Met Phe Ser Ala Lys
215                 220                 225
Glu Val Glu Leu Tyr Val Thr Glu Ile Glu Lys Glu Lys Glu Glu
            230                 235                 240
Ala Glu Lys Lys Lys Ser Lys Lys Ser Val
        245                 250

<210> SEQ ID NO 10
<211> LENGTH: 1045
<212> TYPE: PRT
<213> ORGANISM: Homo sapiens
<220> FEATURE:
<221> NAME/KEY: misc_feature
<223> OTHER INFORMATION: Incyte ID No: 55022586CD1

<400> SEQUENCE: 10

Met Thr Ala Glu Leu Gln Gln Asp Asp Ala Ala Gly Ala Ala Asp
1                5                  10                  15
Gly His Gly Ser Ser Cys Gln Met Leu Leu Asn Gln Leu Arg Glu
             20                  25                  30
Ile Thr Gly Ile Gln Asp Pro Ser Phe Leu His Glu Ala Leu Lys
         35                  40                  45
Ala Ser Asn Gly Asp Ile Thr Gln Ala Val Ser Leu Leu Thr Asp
     50                  55                  60
Glu Arg Val Lys Glu Pro Ser Gln Asp Thr Val Ala Thr Glu Pro
 65                  70                  75
Ser Glu Val Glu Gly Ser Ala Ala Asn Lys Glu Val Leu Ala Lys
             80                  85                  90
Val Ile Asp Leu Thr His Asp Asn Lys Asp Asp Leu Gln Ala Ala
         95                 100                 105
Ile Ala Leu Ser Leu Leu Glu Ser Pro Lys Ile Gln Ala Asp Gly
    110                 115                 120
```

-continued

```
Arg Asp Leu Asn Arg Met His Glu Ala Thr Ser Ala Glu Thr Lys
            125                 130                 135

Arg Ser Lys Arg Lys Arg Cys Glu Val Trp Gly Glu Asn Pro Asn
            140                 145                 150

Pro Asn Asp Trp Arg Arg Val Asp Gly Trp Pro Val Gly Leu Lys
            155                 160                 165

Asn Val Gly Asn Thr Cys Trp Phe Ser Ala Val Ile Gln Ser Leu
            170                 175                 180

Phe Gln Leu Pro Glu Phe Arg Arg Leu Val Leu Ser Tyr Ser Leu
            185                 190                 195

Pro Gln Asn Val Leu Glu Asn Cys Arg Ser His Thr Glu Lys Arg
            200                 205                 210

Asn Ile Met Phe Met Gln Glu Leu Gln Tyr Leu Phe Ala Leu Met
            215                 220                 225

Met Gly Ser Asn Arg Lys Phe Val Asp Pro Ser Ala Ala Leu Asp
            230                 235                 240

Leu Leu Lys Gly Ala Phe Arg Ser Ser Glu Glu Gln Gln Gln Asp
            245                 250                 255

Val Ser Glu Phe Thr His Lys Leu Leu Asp Trp Leu Glu Asp Ala
            260                 265                 270

Phe Gln Leu Ala Val Asn Val Asn Ser Pro Arg Asn Lys Ser Glu
            275                 280                 285

Asn Pro Met Val Gln Leu Phe Tyr Gly Thr Phe Leu Thr Glu Gly
            290                 295                 300

Val Arg Glu Gly Lys Pro Phe Cys Asn Asn Glu Thr Phe Gly Gln
            305                 310                 315

Tyr Pro Leu Gln Val Asn Gly Tyr Arg Asn Leu Asp Glu Cys Leu
            320                 325                 330

Glu Gly Ala Met Val Glu Gly Asp Val Glu Leu Leu Pro Ser Asp
            335                 340                 345

His Ser Val Lys Tyr Gly Gln Glu Arg Trp Phe Thr Lys Leu Pro
            350                 355                 360

Pro Val Leu Thr Phe Glu Leu Ser Arg Phe Glu Phe Asn Gln Ser
            365                 370                 375

Leu Gly Gln Pro Glu Lys Ile His Asn Lys Leu Glu Phe Pro Gln
            380                 385                 390

Ile Ile Tyr Met Asp Arg Tyr Met Tyr Arg Ser Lys Glu Leu Ile
            395                 400                 405

Arg Asn Lys Arg Glu Cys Ile Arg Lys Leu Lys Glu Glu Ile Lys
            410                 415                 420

Ile Leu Gln Gln Lys Leu Glu Arg Tyr Val Lys Tyr Gly Ser Gly
            425                 430                 435

Pro Ala Arg Phe Pro Leu Pro Asp Met Leu Lys Tyr Val Ile Glu
            440                 445                 450

Phe Ala Ser Thr Lys Pro Ala Ser Glu Ser Cys Pro Pro Glu Ser
            455                 460                 465

Asp Thr His Met Thr Leu Pro Leu Ser Ser Val His Cys Ser Val
            470                 475                 480

Ser Asp Gln Thr Ser Lys Glu Ser Thr Ser Thr Glu Ser Ser Ser
            485                 490                 495

Gln Asp Val Glu Ser Thr Phe Ser Ser Pro Glu Asp Ser Leu Pro
            500                 505                 510

Lys Ser Lys Pro Leu Thr Ser Ser Arg Ser Ser Met Glu Met Pro
```

-continued

```
                515                 520                 525
Ser Gln Pro Ala Pro Arg Thr Val Thr Asp Glu Glu Ile Asn Phe
            530                 535                 540
Val Lys Thr Cys Leu Gln Arg Trp Arg Ser Glu Ile Glu Gln Asp
            545                 550                 555
Ile Gln Asp Leu Lys Thr Cys Ile Ala Ser Thr Thr Gln Thr Ile
            560                 565                 570
Glu Gln Met Tyr Cys Asp Pro Leu Leu Arg Gln Val Pro Tyr Arg
            575                 580                 585
Leu His Ala Val Leu Val His Glu Gly Gln Ala Asn Ala Gly His
            590                 595                 600
Tyr Trp Ala Tyr Ile Tyr Asn Gln Pro Arg Gln Ser Trp Leu Lys
            605                 610                 615
Tyr Asn Asp Ile Ser Val Thr Glu Ser Ser Trp Glu Val Glu
            620                 625                 630
Arg Asp Ser Tyr Gly Gly Leu Arg Asn Val Ser Ala Tyr Cys Leu
            635                 640                 645
Met Tyr Ile Asn Asp Lys Leu Pro Tyr Phe Asn Ala Glu Ala Ala
            650                 655                 660
Pro Thr Glu Ser Asp Gln Met Ser Glu Val Glu Ala Leu Ser Val
            665                 670                 675
Glu Leu Lys His Tyr Ile Gln Glu Asp Asn Trp Arg Phe Glu Gln
            680                 685                 690
Glu Val Glu Glu Trp Glu Glu Gln Ser Cys Lys Ile Pro Gln
            695                 700                 705
Met Glu Ser Ser Thr Asn Ser Ser Ser Gln Asp Tyr Ser Thr Ser
            710                 715                 720
Gln Glu Pro Ser Val Ala Ser Ser His Gly Val Arg Cys Leu Ser
            725                 730                 735
Ser Glu His Ala Val Ile Val Lys Glu Gln Thr Ala Gln Ala Ile
            740                 745                 750
Ala Asn Thr Ala Arg Ala Tyr Glu Lys Ser Gly Val Glu Ala Ala
            755                 760                 765
Leu Ser Glu Ala Phe His Glu Glu Tyr Ser Arg Leu Tyr Gln Leu
            770                 775                 780
Ala Lys Glu Thr Pro Thr Ser His Ser Asp Pro Arg Leu Gln His
            785                 790                 795
Val Leu Val Tyr Phe Phe Gln Asn Glu Ala Pro Lys Arg Val Val
            800                 805                 810
Glu Arg Thr Leu Leu Glu Gln Phe Ala Asp Lys Asn Leu Ser Tyr
            815                 820                 825
Asp Glu Arg Ser Ile Ser Ile Met Lys Val Ala Gln Ala Lys Leu
            830                 835                 840
Lys Glu Ile Gly Pro Asp Asp Met Asn Met Glu Glu Tyr Lys Lys
            845                 850                 855
Trp His Glu Asp Tyr Ser Leu Phe Arg Lys Val Ser Val Tyr Leu
            860                 865                 870
Leu Thr Gly Leu Glu Leu Tyr Gln Lys Gly Lys Tyr Gln Glu Ala
            875                 880                 885
Leu Ser Tyr Leu Val Tyr Ala Tyr Gln Ser Asn Ala Ala Leu Leu
            890                 895                 900
Met Lys Gly Pro Arg Arg Gly Val Lys Glu Ser Val Ile Ala Leu
            905                 910                 915
```

-continued

```
Tyr Arg Arg Lys Cys Leu Leu Glu Leu Asn Ala Lys Ala Ala Ser
            920                 925                 930

Leu Phe Glu Thr Asn Asp Asp His Ser Val Thr Gly Ile Asn
            935                 940                 945

Val Met Asn Glu Leu Ile Ile Pro Cys Ile His Leu Ile Ile Asn
            950                 955                 960

Asn Asp Ile Ser Lys Asp Leu Asp Ala Ile Glu Val Met Arg
            965                 970                 975

Asn His Trp Cys Ser Tyr Leu Gly Gln Asp Ile Ala Glu Asn Leu
            980                 985                 990

Gln Leu Cys Leu Gly Glu Phe Leu Pro Arg Leu Leu Asp Pro Ser
            995                1000                1005

Ala Glu Ile Ile Val Leu Lys Glu Pro Pro Thr Ile Arg Pro Asn
                 1010                1015               1020

Ser Pro Tyr Asp Leu Cys Ser Arg Phe Ala Ala Val Met Glu Ser
                 1025                1030               1035

Ile Gln Gly Val Ser Thr Val Thr Val Lys
                 1040                1045

<210> SEQ ID NO 11
<211> LENGTH: 622
<212> TYPE: PRT
<213> ORGANISM: Homo sapiens
<220> FEATURE:
<221> NAME/KEY: misc_feature
<223> OTHER INFORMATION: Incyte ID No: 3238072CD1

<400> SEQUENCE: 11

Met Glu Val Arg Asp Leu Tyr Val Phe Cys Tyr Leu Cys Lys Asp
1               5                  10                  15

Tyr Val Leu Asn Asp Asn Pro Glu Gly Asp Leu Lys Leu Leu Arg
            20                  25                  30

Ser Ser Leu Leu Ala Val Arg Gly Gln Lys Gln Asp Thr Pro Val
            35                  40                  45

Arg Arg Gly Arg Thr Leu Arg Ser Met Ala Ser Gly Glu Asp Val
            50                  55                  60

Val Leu Pro Gln Arg Ala Pro Gln Gly Gln Pro Gln Met Leu Thr
            65                  70                  75

Ala Leu Trp Tyr Arg Arg Gln Arg Leu Leu Ala Arg Thr Leu Arg
            80                  85                  90

Leu Trp Phe Glu Lys Ser Ser Arg Gly Gln Ala Lys Leu Glu Gln
            95                 100                 105

Arg Arg Gln Glu Glu Ala Leu Glu Arg Lys Lys Glu Glu Ala Arg
           110                 115                 120

Arg Arg Arg Arg Glu Val Lys Arg Arg Leu Leu Glu Glu Leu Ala
           125                 130                 135

Ser Thr Pro Pro Arg Lys Ser Ala Arg Leu Leu Leu His Thr Pro
           140                 145                 150

Arg Asp Ala Gly Pro Ala Ala Ser Arg Pro Ala Ala Leu Pro Thr
           155                 160                 165

Ser Arg Arg Val Pro Ala Ala Thr Leu Lys Leu Arg Arg Gln Pro
           170                 175                 180

Ala Met Ala Pro Gly Val Thr Gly Leu Arg Asn Leu Gly Asn Thr
           185                 190                 195

Cys Tyr Met Asn Ser Ile Leu Gln Val Leu Ser His Leu Gln Lys
```

-continued

```
                200                 205                 210
Phe Arg Glu Cys Phe Leu Asn Leu Asp Pro Ser Lys Thr Glu His
            215                 220                 225
Leu Phe Pro Lys Ala Thr Asn Gly Lys Thr Gln Leu Ser Gly Lys
            230                 235                 240
Pro Thr Asn Ser Ser Ala Thr Glu Leu Ser Leu Arg Asn Asp Arg
            245                 250                 255
Ala Glu Ala Cys Glu Arg Glu Gly Phe Cys Trp Asn Gly Arg Ala
            260                 265                 270
Ser Ile Ser Arg Ser Leu Glu Leu Ile Gln Asn Lys Glu Pro Ser
            275                 280                 285
Ser Lys His Ile Ser Leu Cys Arg Glu Leu His Thr Leu Phe Arg
            290                 295                 300
Val Met Trp Ser Gly Lys Trp Ala Leu Val Ser Pro Phe Ala Met
            305                 310                 315
Leu His Ser Val Trp Ser Leu Ile Pro Ala Phe Arg Gly Tyr Asp
            320                 325                 330
Gln Gln Asp Ala Gln Glu Phe Leu Cys Glu Leu Leu His Lys Val
            335                 340                 345
Gln Gln Glu Leu Glu Ser Glu Gly Thr Thr Arg Arg Ile Leu Ile
            350                 355                 360
Pro Phe Ser Gln Arg Lys Leu Thr Lys Gln Val Leu Lys Val Val
            365                 370                 375
Asn Thr Ile Phe His Gly Gln Leu Leu Ser Gln Val Thr Cys Ile
            380                 385                 390
Ser Cys Asn Tyr Lys Ser Asn Thr Ile Glu Pro Phe Trp Asp Leu
            395                 400                 405
Ser Leu Glu Phe Pro Glu Arg Tyr His Cys Ile Glu Lys Gly Phe
            410                 415                 420
Val Pro Leu Asn Gln Thr Glu Cys Leu Leu Thr Glu Met Leu Ala
            425                 430                 435
Lys Phe Thr Glu Thr Glu Ala Leu Glu Gly Arg Ile Tyr Ala Cys
            440                 445                 450
Asp Gln Cys Asn Ser Lys Arg Arg Lys Ser Asn Pro Lys Pro Leu
            455                 460                 465
Val Leu Ser Glu Ala Arg Lys Gln Leu Met Ile Tyr Arg Leu Pro
            470                 475                 480
Gln Val Leu Arg Leu His Leu Lys Arg Phe Arg Trp Ser Gly Arg
            485                 490                 495
Asn His Arg Glu Lys Ile Gly Val His Val Val Phe Asp Gln Val
            500                 505                 510
Leu Thr Met Glu Pro Tyr Cys Cys Arg Asp Met Leu Ser Ser Leu
            515                 520                 525
Asp Lys Glu Thr Phe Ala Tyr Asp Leu Ser Ala Val Val Met His
            530                 535                 540
His Gly Lys Gly Phe Gly Ser Gly His Tyr Thr Ala Tyr Cys Tyr
            545                 550                 555
Asn Thr Glu Gly Gly Phe Trp Val His Cys Asn Asp Ser Lys Leu
            560                 565                 570
Asn Val Cys Ser Val Glu Glu Val Cys Lys Thr Gln Ala Tyr Ile
            575                 580                 585
Leu Phe Tyr Thr Gln Arg Thr Val Gln Gly Asn Ala Arg Ile Ser
            590                 595                 600
```

-continued

Glu Thr His Leu Gln Ala Gln Val Gln Ser Ser Asn Asn Asp Glu
                605                 610                 615

Gly Arg Pro Gln Thr Phe Ser
                620

<210> SEQ ID NO 12
<211> LENGTH: 345
<212> TYPE: PRT
<213> ORGANISM: Homo sapiens
<220> FEATURE:
<221> NAME/KEY: misc_feature
<223> OTHER INFORMATION: Incyte ID No: 7482034CD1

<400> SEQUENCE: 12

Met Lys Arg Gln Leu Thr His Leu Pro Gly Arg Phe Trp Leu Trp
1               5                   10                  15

Pro Ser Phe Ser Val Ala Ser Leu Leu Ser His Gln Thr Pro Ala
                20                  25                  30

Thr Asn Ser Trp Leu Ala Ser Ser Lys Leu His Ser Ala Pro Gly
                35                  40                  45

Met Ala Leu Gln Asp Val Cys Lys Trp Gln Ser Pro Asp Thr Gln
                50                  55                  60

Gly Pro Ser Pro His Leu Pro Arg Ala Gly Gly Trp Ala Val Pro
                65                  70                  75

Arg Gly Cys Asp Pro Gln Thr Phe Leu Gln Ile His Gly Pro Arg
                80                  85                  90

Leu Ala His Gly Thr Thr Thr Leu Ala Phe Arg Phe Arg His Gly
                95                  100                 105

Val Ile Ala Ala Ala Asp Thr Arg Ser Ser Cys Gly Ser Tyr Val
                110                 115                 120

Ala Cys Pro Ala Ser Cys Lys Val Ile Pro Val His Gln His Leu
                125                 130                 135

Leu Gly Thr Thr Ser Gly Thr Ser Ala Asp Cys Ala Thr Trp Tyr
                140                 145                 150

Arg Val Leu Gln Arg Glu Leu Arg Leu Arg Glu Leu Arg Glu Gly
                155                 160                 165

Gln Leu Pro Ser Val Ala Ser Ala Lys Leu Leu Ser Ala Met
                170                 175                 180

Met Ser Gln Tyr Arg Gly Leu Asp Leu Cys Val Ala Thr Ala Leu
                185                 190                 195

Cys Gly Trp Asp Arg Ser Gly Pro Glu Leu Phe Tyr Val Tyr Ser
                200                 205                 210

Asp Gly Thr Arg Leu Gln Gly Asp Ile Phe Ser Val Gly Ser Gly
                215                 220                 225

Ser Pro Tyr Ala Tyr Gly Val Leu Asp Arg Gly Tyr Arg Tyr Asp
                230                 235                 240

Met Ser Thr Gln Glu Ala Tyr Ala Leu Ala Arg Cys Ala Val Ala
                245                 250                 255

His Ala Thr His Arg Asp Ala Tyr Ser Gly Gly Ser Val Asp Leu
                260                 265                 270

Phe His Val Arg Glu Ser Gly Trp Glu His Val Ser Arg Ser Asp
                275                 280                 285

Ala Cys Val Leu Tyr Val Glu Leu Gln Lys Leu Leu Glu Pro Glu
                290                 295                 300

Pro Glu Glu Asp Ala Ser His Ala His Pro Glu Pro Ala Thr Ala

-continued

```
                    305                 310                 315
His Arg Ala Ala Glu Asp Arg Glu Leu Ser Val Gly Pro Gly Glu
                320                 325                 330
Val Thr Pro Gly Asp Ser Arg Met Pro Ala Gly Thr Glu Thr Val
            335                 340                 345

<210> SEQ ID NO 13
<211> LENGTH: 948
<212> TYPE: PRT
<213> ORGANISM: Homo sapiens
<220> FEATURE:
<221> NAME/KEY: misc_feature
<223> OTHER INFORMATION: Incyte ID No: 7474351CD1

<400> SEQUENCE: 13

Met Val Ser Lys Gly Gly Val Ala Ala Glu Pro Glu Pro His Tyr
1               5                   10                  15
Cys Glu Asp Ser Glu Arg Gly Pro Asn Thr Leu Thr Gly Pro Gly
                20                  25                  30
Ser Leu Pro Arg Gly Gly Ile Glu Val Gly Met Glu Phe Pro
                35                  40                  45
Gly Cys Ser Gly Glu Gly Cys Val Lys Pro His Glu Glu Ala Ala
                50                  55                  60
Arg Glu Gly Ala Gly Arg Gly Lys Arg Ala Val Pro Gly Pro Lys
            65                  70                  75
Arg Arg Gln Gln Gly Ser Ala Glu Gly Pro Ala Ala Gly Trp Thr
                80                  85                  90
Leu Glu Gln Glu Thr Arg Gly Asp Val Leu Glu Asp Lys Asn Glu
                95                  100                 105
Arg Ala Asp Glu Glu Ile Leu Arg Leu Ala Pro Gly Lys Gly Arg
                110                 115                 120
Leu Pro Ile Asp Ser Lys His Leu Lys Pro Val Ile Ser Ser Phe
                125                 130                 135
Pro Val Arg Ser Gln Glu Leu Gly Glu Gly Ala Gly Ala Gly Thr
                140                 145                 150
Leu Arg Gly Lys Met Ala Glu Phe Asn Trp Ser Met Ala Phe Lys
                155                 160                 165
Gly Pro Ala Ala Gly His Glu Glu Arg Leu Asn Ser Val Ser Ser
                170                 175                 180
Arg Ala Lys Lys Gly Ile Gly Trp Asp Val Ala Ala Ala Ser Leu
                185                 190                 195
Arg Gly Val Asp His Phe Ser Asp Leu Pro Pro Pro Leu Gln Val
                200                 205                 210
Arg Glu Glu Leu Glu Ala Cys Ala Phe Arg Val Gln Val Gly Gln
                215                 220                 225
Leu Arg Leu Tyr Glu Asp Asp Gln Arg Thr Lys Val Val Glu Ile
                230                 235                 240
Val Arg His Pro Gln Tyr Asn Glu Ser Leu Ser Ala Gln Gly Gly
                245                 250                 255
Ala Asp Ile Ala Leu Leu Lys Leu Glu Ala Pro Val Pro Leu Ser
                260                 265                 270
Glu Leu Ile His Pro Val Ser Leu Pro Ser Ala Ser Leu Asp Val
                275                 280                 285
Pro Ser Gly Lys Thr Cys Trp Val Thr Gly Trp Gly Val Ile Gly
                290                 295                 300
```

```
Arg Gly Glu Leu Leu Pro Trp Pro Leu Ser Leu Trp Glu Ala Thr
            305                 310                 315
Val Lys Val Arg Ser Asn Val Leu Cys Asn Gln Thr Cys Arg Arg
            320                 325                 330
Arg Phe Pro Ser Asn His Thr Glu Arg Phe Glu Arg Leu Ile Lys
            335                 340                 345
Asp Asp Met Leu Cys Ala Gly Asp Gly Asn His Gly Ser Trp Pro
            350                 355                 360
Gly Asp Asn Gly Gly Pro Leu Leu Cys Arg Arg Asn Cys Thr Trp
            365                 370                 375
Val Gln Val Glu Val Ser Trp Gly Lys Leu Cys Gly Leu Arg
            380                 385                 390
Gly Tyr Pro Gly Met Tyr Thr Arg Val Thr Ser Tyr Val Ser Trp
            395                 400                 405
Ile Arg Gln Pro Cys Pro Ser Ala Gln Thr Pro Ala Val Val Arg
            410                 415                 420
Arg Phe Val Leu Pro Pro Asn Pro Asp Val Glu Ala Leu Thr Pro
            425                 430                 435
Ser Val Met Gly Ser Gly Ala Pro Leu Pro Ala Pro Asp Leu
            440                 445                 450
Gln Glu Ala Glu Val Pro Ile Met Arg Thr Arg Ala Cys Glu Arg
            455                 460                 465
Met Tyr His Lys Gly Pro Thr Ala His Gly Gln Val Thr Ile Ile
            470                 475                 480
Lys Ala Ala Met Pro Cys Ala Gly Arg Lys Gly Gln Gly Ser Cys
            485                 490                 495
Gln Ala Ala Leu Arg Thr Glu Asp Leu Thr Pro Thr Thr Pro Asn
            500                 505                 510
Thr Glu Val Ser Pro Arg Ala Asp Pro Arg Leu Ser Gln Pro Glu
            515                 520                 525
Asp Ile Trp Pro Glu Trp Ala Trp Pro Val Val Gly Thr Thr
            530                 535                 540
Met Leu Leu Leu Leu Phe Leu Ala Val Ser Ser Leu Gly Ser
            545                 550                 555
Cys Ser Thr Gly Ser Pro Ala Pro Val Pro Glu Asn Asp Leu Val
            560                 565                 570
Gly Ile Val Gly Gly His Asn Thr Pro Gly Glu Val Val Ala
            575                 580                 585
Val Gly Ala Asp Arg Arg Ser Leu His Phe Pro Glu Gly His Arg
            590                 595                 600
Pro Val His Leu Pro Asp Ser His Gln Gly Cys Val Ser Val Arg
            605                 610                 615
Gly Pro Gly Ala Ala Glu Cys Gln Pro Asp Arg Arg Pro Asn
            620                 625                 630
Tyr Ser Val Phe Phe Leu Gly Ala Asp Ile Ala Leu Leu Lys Leu
            635                 640                 645
Ala Thr Ser Ser Leu Glu Phe Thr Asp Ser Asp Asn Cys Trp Asn
            650                 655                 660
Thr Gly Trp Gly Met Val Gly Leu Leu Asp Met Leu Pro Pro
            665                 670                 675
Tyr Arg Pro Gln Gln Val Lys Val Leu Thr Leu Ser Asn Ala Asp
            680                 685                 690
Cys Glu Arg Gln Thr Tyr Asp Ala Phe Pro Gly Ala Gly Asp Arg
```

```
                    695                 700                 705

Lys Phe Ile Gln Asp Asp Met Ile Cys Ala Gly Arg Thr Gly Arg
                710                 715                 720

Arg Thr Trp Lys Gly Asp Ser Gly Gly Pro Leu Val Cys Lys Lys
                725                 730                 735

Lys Gly Thr Trp Leu Gln Ala Gly Val Val Ser Trp Gly Phe Tyr
                740                 745                 750

Ser Asp Arg Pro Ser Ile Gly Val Tyr Thr Arg Pro Glu Thr Ser
                755                 760                 765

Trp Gln Gly Ala Asn His Ala Asp Ala Gln Arg Pro Ala Gly Arg
                770                 775                 780

Val Pro Thr Met Gln Arg Pro Arg Asp Met Gly Gln Gly Gln Glu
                785                 790                 795

Trp Val Cys Arg Pro Phe Thr His Val Thr Cys Tyr Pro Thr Ala
                800                 805                 810

Ile Pro Arg Pro Phe Thr His Val Thr Cys Tyr Leu Met Ala Val
                815                 820                 825

Pro Ser Thr Leu Thr His Val Thr Cys Tyr Pro Thr Ala Val Pro
                830                 835                 840

Arg Pro Phe Thr His Val Thr Cys Tyr Leu Met Ala Val Pro Ser
                845                 850                 855

Thr Leu Thr His Ile Thr Cys Tyr Met Met Ala Val Pro Arg Pro
                860                 865                 870

Phe Thr His Ile Thr Cys Tyr Pro Met Ala Val Pro Ser Thr Leu
                875                 880                 885

Thr His Val Thr Cys His Pro Thr Ala Ile Pro Arg Pro Phe Thr
                890                 895                 900

His Ile Thr Cys Tyr Thr Met Ala Ile Pro Arg Pro Ser Thr Thr
                905                 910                 915

Pro Pro Ala Thr Arg Arg Pro Ser Pro Ala Pro Ser Pro Thr Ser
                920                 925                 930

Pro Ala Thr Arg Trp Pro Ser Pro Gly Pro Ser Pro Met Ser Pro
                935                 940                 945

Ala Thr Arg

<210> SEQ ID NO 14
<211> LENGTH: 444
<212> TYPE: PRT
<213> ORGANISM: Homo sapiens
<220> FEATURE:
<221> NAME/KEY: misc_feature
<223> OTHER INFORMATION: Incyte ID No: 2232483CD1

<400> SEQUENCE: 14

Met Gly Ser Ala Pro Trp Ala Pro Val Leu Leu Ala Leu Gly
1               5                   10                  15

Leu Arg Gly Leu Gln Ala Gly Ala Arg Arg Ala Pro Asp Pro Gly
                20                  25                  30

Phe Gln Glu Arg Phe Phe Gln Gln Arg Leu Asp His Phe Asn Phe
                35                  40                  45

Glu Arg Phe Gly Asn Arg Thr Phe Pro Gln Arg Phe Leu Val Ser
                50                  55                  60

Asp Arg Phe Trp Val Arg Gly Glu Gly Pro Ile Phe Phe Tyr Thr
                65                  70                  75

Gly Asn Glu Gly Asp Val Trp Ala Phe Ala Asn Asn Ser Ala Phe
```

-continued

```
                80                   85                   90
Val Ala Glu Leu Ala Ala Glu Arg Gly Ala Leu Leu Val Phe Ala
                95                  100                  105
Glu His Arg Tyr Tyr Gly Lys Ser Leu Pro Phe Gly Ala Gln Ser
               110                  115                  120
Thr Gln Arg Gly His Thr Glu Leu Leu Thr Val Glu Gln Ala Leu
               125                  130                  135
Ala Asp Phe Ala Glu Leu Leu Arg Ala Leu Arg Arg Asp Leu Gly
               140                  145                  150
Ala Gln Asp Ala Pro Ala Ile Ala Phe Gly Gly Ser Tyr Gly Gly
               155                  160                  165
Met Leu Ser Ala Tyr Leu Arg Met Lys Tyr Pro His Leu Val Ala
               170                  175                  180
Gly Ala Leu Ala Ala Ser Ala Pro Val Leu Ala Val Ala Gly Leu
               185                  190                  195
Gly Asp Ser Asn Gln Phe Phe Arg Asp Val Thr Ala Gly Ala Tyr
               200                  205                  210
Asp Thr Val Arg Trp Glu Phe Gly Thr Cys Gln Pro Leu Ser Asp
               215                  220                  225
Glu Lys Asp Leu Thr Gln Leu Phe Met Phe Ala Arg Asn Ala Phe
               230                  235                  240
Thr Val Leu Ala Met Met Asp Tyr Pro Tyr Pro Thr Asp Phe Leu
               245                  250                  255
Gly Pro Leu Pro Ala Asn Pro Val Lys Val Gly Cys Asp Arg Leu
               260                  265                  270
Leu Ser Glu Ala Gln Arg Ile Thr Gly Leu Arg Ala Leu Ala Gly
               275                  280                  285
Leu Val Tyr Asn Ala Ser Gly Ser Glu His Cys Tyr Asp Ile Tyr
               290                  295                  300
Arg Leu Tyr His Ser Cys Ala Asp Pro Thr Gly Cys Gly Thr Gly
               305                  310                  315
Pro Asp Ala Arg Ala Trp Asp Tyr Gln Ala Cys Thr Glu Ile Asn
               320                  325                  330
Leu Thr Phe Ala Ser Asn Asn Val Thr Asp Met Phe Pro Asp Leu
               335                  340                  345
Pro Phe Thr Asp Glu Leu Arg Pro Ser Asp Leu Arg Ala Ala Ser
               350                  355                  360
Asn Ile Ile Phe Ser Asn Gly Asn Leu Asp Pro Cys Gly Arg Gly
               365                  370                  375
Gly Ile Arg Arg Asn Leu Ser Ala Ser Val Ile Ala Val Thr Ile
               380                  385                  390
Gln Gly Gly Ala His His Leu Asp Leu Arg Ala Ser His Pro Glu
               395                  400                  405
Asp Pro Ala Ser Val Val Glu Ala Arg Lys Leu Glu Ala Thr Ile
               410                  415                  420
Ile Gly Glu Cys Val Lys Ala Ala Arg Arg Glu Gln Gln Pro Ala
               425                  430                  435
Leu Arg Trp Gly Ala Gln Ile Ser Leu
               440

<210> SEQ ID NO 15
<211> LENGTH: 514
<212> TYPE: PRT
<213> ORGANISM: Homo sapiens
```

```
<220> FEATURE:
<221> NAME/KEY: misc_feature
<223> OTHER INFORMATION: Incyte ID No: 7481712CD1

<400> SEQUENCE: 15

Met Arg Val Pro Phe Ser Glu Leu Lys Asp Ile Lys Ala Tyr Leu
1               5                   10                  15

Glu Ser His Gly Leu Ala Tyr Ser Ile Met Ile Lys Asp Ile Gln
                20                  25                  30

Val Lys Pro Cys Pro Ser Trp Asp Pro Ala Phe Arg Leu Pro Phe
                35                  40                  45

Trp Leu Gly Pro Asn Met Glu Glu Met Phe Ser Gly Leu Lys Val
                50                  55                  60

Asp Met Trp Phe Leu Gly Leu His Gln Arg Val Cys Glu His Ala
                65                  70                  75

Val Glu Gly Thr Gly Cys Pro Pro His Phe Thr Lys Ala Ser
                80                  85                  90

Leu Asp Asn Val Thr Arg Asn Phe Gln Ile Gln Pro Asp Gly Arg
                95                  100                 105

Leu Ser Met Phe Leu Phe Gln Gln His Asn Trp Ser Leu Ser Pro
                110                 115                 120

Ser Trp Ser Leu Ser Leu Pro Leu Ala Ser Arg Thr Ser Val Phe
                125                 130                 135

Cys Leu Gln Pro Ala Pro Pro Leu Leu Asp Pro Thr Ala Tyr Ser
                140                 145                 150

Val Phe Pro Pro Gly Gly Ala Met Gly Ile Ser Asn Phe Pro Ala
                155                 160                 165

Pro Gly Met Glu Gln Thr Leu Val His Phe Pro Gly Gln Gly Arg
                170                 175                 180

Phe Leu Phe Leu Glu Val Gly Pro Ala Val Leu Leu Asp Glu Glu
                185                 190                 195

Arg Gln Ala Met Ala Lys Ser Arg Arg Leu Glu Arg Ser Thr Asn
                200                 205                 210

Ser Phe Ser Tyr Ser Ser Tyr His Thr Leu Glu Glu Ile Tyr Ser
                215                 220                 225

Trp Ile Asp Asn Phe Val Met Glu His Ser Asp Ile Val Ser Lys
                230                 235                 240

Ile Gln Ile Gly Asn Ser Phe Glu Asn Gln Ser Ile Leu Val Leu
                245                 250                 255

Lys Phe Ser Thr Gly Gly Ser Arg His Pro Ala Ile Trp Ile Asp
                260                 265                 270

Thr Gly Ile His Ser Arg Glu Trp Ile Thr His Ala Thr Gly Ile
                275                 280                 285

Trp Thr Ala Asn Lys Ile Val Ser Asp Tyr Gly Lys Asp Arg Val
                290                 295                 300

Leu Thr Asp Ile Leu Asn Ala Met Asp Ile Phe Ile Glu Leu Val
                305                 310                 315

Thr Asn Pro Asp Gly Phe Ala Phe Thr His Ser Met Asn Arg Leu
                320                 325                 330

Trp Arg Lys Asn Lys Ser Ile Arg Pro Gly Ile Phe Cys Ile Gly
                335                 340                 345

Val Asp Leu Asn Arg Asn Trp Lys Ser Gly Phe Gly Gly Asn Gly
                350                 355                 360

Ser Asn Ser Asn Pro Cys Ser Glu Thr Tyr His Gly Pro Ser Pro
```

-continued

```
                365                 370                 375
Gln Ser Glu Pro Glu Val Ala Ala Ile Val Asn Phe Ile Thr Ala
            380                 385                 390
His Gly Asn Phe Lys Ala Leu Ile Ser Ile His Ser Tyr Ser Gln
        395                 400                 405
Met Leu Met Tyr Pro Tyr Gly Arg Leu Leu Glu Pro Val Ser Asn
    410                 415                 420
Gln Arg Glu Leu Tyr Asp Leu Ala Lys Asp Ala Val Glu Ala Leu
425                 430                 435
Tyr Lys Val His Gly Ile Glu Tyr Ile Phe Gly Ser Ile Ser Thr
            440                 445                 450
Thr Leu Tyr Val Ala Ser Gly Ile Thr Val Asp Trp Ala Tyr Asp
        455                 460                 465
Ser Gly Ile Lys Tyr Ala Phe Ser Phe Glu Leu Arg Asp Thr Gly
    470                 475                 480
Gln Tyr Gly Phe Leu Leu Pro Ala Thr Gln Ile Ile Pro Thr Ala
485                 490                 495
Gln Glu Thr Trp Met Ala Leu Arg Thr Ile Met Glu His Thr Leu
            500                 505                 510
Asn His Pro Tyr

<210> SEQ ID NO 16
<211> LENGTH: 787
<212> TYPE: PRT
<213> ORGANISM: Homo sapiens
<220> FEATURE:
<221> NAME/KEY: misc_feature
<223> OTHER INFORMATION: Incyte ID No: 8213480CD1

<400> SEQUENCE: 16

Met Gly Trp Arg Pro Arg Ala Arg Gly Thr Pro Leu Leu Leu
1               5                   10                  15
Leu Leu Leu Leu Leu Leu Trp Pro Val Pro Gly Ala Gly Val
            20                  25                  30
Leu Gln Gly His Ile Pro Gly Gln Pro Val Thr Pro His Trp Val
        35                  40                  45
Leu Asp Gly Gln Pro Trp Arg Thr Val Ser Leu Glu Glu Pro Val
    50                  55                  60
Ser Lys Pro Asp Met Gly Leu Val Ala Leu Glu Ala Glu Gly Gln
65                  70                  75
Glu Leu Leu Leu Glu Leu Glu Lys Asn His Arg Leu Leu Ala Pro
            80                  85                  90
Gly Tyr Ile Glu Thr His Tyr Gly Pro Asp Gly Gln Pro Val Val
        95                  100                 105
Leu Ala Pro Asn His Thr Asp His Cys His Tyr Gln Gly Arg Val
    110                 115                 120
Arg Gly Phe Pro Asp Ser Trp Val Val Leu Cys Thr Cys Ser Gly
125                 130                 135
Met Ser Gly Leu Ile Thr Leu Ser Arg Asn Ala Ser Tyr Tyr Leu
            140                 145                 150
Arg Pro Trp Pro Pro Arg Gly Ser Lys Asp Phe Ser Thr His Glu
        155                 160                 165
Ile Phe Arg Met Glu Gln Leu Leu Thr Trp Lys Gly Thr Cys Gly
    170                 175                 180
His Arg Asp Pro Gly Asn Lys Ala Gly Met Thr Ser Leu Pro Gly
```

```
                185                 190                 195
Gly Pro Gln Ser Arg Gly Arg Arg Glu Ala Arg Arg Thr Arg Lys
                200                 205                 210
Tyr Leu Glu Leu Tyr Ile Val Ala Asp His Thr Leu Phe Leu Thr
                215                 220                 225
Arg His Arg Asn Leu Asn His Thr Lys Gln Arg Leu Leu Glu Val
                230                 235                 240
Ala Asn Tyr Val Asp Gln Leu Leu Arg Thr Leu Asp Ile Gln Val
                245                 250                 255
Ala Leu Thr Gly Leu Glu Val Trp Thr Glu Arg Asp Arg Ser Arg
                260                 265                 270
Val Thr Gln Asp Ala Asn Ala Thr Leu Trp Ala Phe Leu Gln Trp
                275                 280                 285
Arg Arg Gly Leu Trp Ala Gln Arg Pro His Asp Ser Ala Gln Leu
                290                 295                 300
Leu Thr Gly Arg Ala Phe Gln Gly Ala Thr Val Gly Leu Ala Pro
                305                 310                 315
Val Glu Gly Met Cys Arg Ala Glu Ser Ser Gly Gly Val Ser Thr
                320                 325                 330
Asp His Ser Glu Leu Pro Ile Gly Ala Ala Thr Met Ala His
                335                 340                 345
Glu Ile Gly His Ser Leu Gly Leu Ser His Asp Pro Asp Gly Cys
                350                 355                 360
Cys Val Glu Ala Ala Glu Ser Gly Gly Cys Val Met Ala Ala
                365                 370                 375
Ala Thr Gly His Pro Phe Pro Arg Val Phe Ser Ala Cys Ser Arg
                380                 385                 390
Arg Gln Leu Arg Ala Phe Phe Arg Lys Gly Gly Gly Ala Cys Leu
                395                 400                 405
Ser Asn Ala Pro Asp Pro Gly Leu Pro Val Pro Pro Ala Leu Cys
                410                 415                 420
Gly Asn Gly Phe Val Glu Ala Gly Glu Glu Cys Asp Cys Gly Pro
                425                 430                 435
Gly Gln Glu Cys Arg Asp Leu Cys Cys Phe Ala His Asn Cys Ser
                440                 445                 450
Leu Arg Pro Gly Ala Gln Cys Ala His Gly Asp Cys Cys Val Arg
                455                 460                 465
Cys Leu Leu Lys Pro Ala Gly Ala Leu Cys Arg Gln Ala Met Gly
                470                 475                 480
Asp Cys Asp Leu Pro Glu Phe Cys Thr Gly Thr Ser Ser His Cys
                485                 490                 495
Pro Pro Asp Val Tyr Leu Leu Asp Gly Ser Pro Cys Ala Arg Gly
                500                 505                 510
Ser Gly Tyr Cys Trp Asp Gly Ala Cys Pro Thr Leu Glu Gln Gln
                515                 520                 525
Cys Gln Gln Leu Trp Gly Pro Gly Ser His Pro Ala Pro Glu Ala
                530                 535                 540
Cys Phe Gln Val Val Asn Ser Ala Gly Asp Ala His Gly Asn Cys
                545                 550                 555
Gly Gln Asp Ser Glu Gly His Phe Leu Pro Cys Ala Gly Arg Asp
                560                 565                 570
Ala Leu Cys Gly Lys Leu Gln Cys Gln Gly Gly Lys Pro Ser Leu
                575                 580                 585
```

-continued

```
Leu Ala Pro His Met Val Pro Val Asp Ser Thr Val His Leu Asp
            590                 595                 600

Gly Gln Glu Val Thr Cys Arg Gly Ala Leu Ala Leu Pro Ser Ala
            605                 610                 615

Gln Leu Asp Leu Leu Gly Leu Gly Leu Val Glu Pro Gly Thr Gln
            620                 625                 630

Cys Gly Pro Arg Met Val Cys Asn Ser Asn His Asn Cys His Cys
            635                 640                 645

Ala Pro Gly Trp Ala Pro Pro Phe Cys Asp Lys Pro Gly Phe Gly
            650                 655                 660

Gly Ser Met Asp Ser Gly Pro Val Gln Ala Glu Asn His Asp Thr
            665                 670                 675

Phe Leu Leu Ala Met Leu Leu Ser Val Leu Leu Pro Leu Leu Pro
            680                 685                 690

Gly Ala Gly Leu Ala Trp Cys Cys Tyr Arg Leu Pro Gly Ala His
            695                 700                 705

Leu Gln Arg Cys Ser Trp Gly Cys Arg Arg Asp Pro Ala Cys Ser
            710                 715                 720

Gly Pro Lys Asp Gly Pro His Arg Asp His Pro Leu Gly Gly Val
            725                 730                 735

His Pro Thr Glu Leu Gly Pro Thr Ala Thr Gly Gln Ser Trp Pro
            740                 745                 750

Leu Asp Pro Glu Asn Ser His Glu Pro Ser Ser His Pro Glu Lys
            755                 760                 765

Pro Leu Pro Ala Val Ser Pro Asp Pro Gln Ala Asp Gln Val Gln
            770                 775                 780

Met Pro Arg Ser Cys Leu Trp
            785

<210> SEQ ID NO 17
<211> LENGTH: 1082
<212> TYPE: PRT
<213> ORGANISM: Homo sapiens
<220> FEATURE:
<221> NAME/KEY: misc_feature
<223> OTHER INFORMATION: Incyte ID No: 7478405CD1

<400> SEQUENCE: 17

Met Glu Cys Ala Leu Leu Leu Ala Cys Ala Phe Pro Ala Ala Gly
1               5                   10                  15

Ser Gly Pro Pro Arg Gly Leu Ala Gly Leu Gly Arg Val Ala Lys
                20                  25                  30

Ala Leu Gln Leu Cys Cys Leu Cys Ala Ser Val Ala Ala
                35                  40                  45

Leu Ala Ser Asp Ser Ser Ser Gly Ala Ser Gly Leu Asn Asp Asp
                50                  55                  60

Tyr Val Phe Val Thr Pro Val Glu Val Asp Ser Ala Gly Ser Tyr
                65                  70                  75

Ile Ser His Asp Ile Leu His Asn Gly Arg Lys Lys Arg Ser Ala
                80                  85                  90

Gln Asn Ala Arg Ser Ser Leu His Tyr Arg Phe Ser Ala Phe Gly
                95                  100                 105

Gln Glu Leu His Leu Glu Leu Lys Pro Ser Ala Ile Leu Ser Ser
                110                 115                 120

His Phe Ile Val Gln Val Leu Gly Lys Asp Gly Ala Ser Glu Thr
```

```
                    125                 130                 135
Gln Lys Pro Glu Val Gln Gln Cys Phe Tyr Gln Gly Phe Ile Arg
                140                 145                 150
Asn Asp Ser Ser Ser Val Ala Val Ser Thr Cys Ala Gly Leu
                155                 160                 165
Ser Gly Leu Ile Arg Thr Arg Lys Asn Glu Phe Leu Ile Ser Pro
                170                 175                 180
Leu Pro Gln Leu Leu Ala Gln Glu His Asn Tyr Ser Pro Ala
                185                 190                 195
Gly His His Pro His Val Leu Tyr Lys Arg Thr Ala Glu Glu Lys
                200                 205                 210
Ile Gln Arg Tyr Arg Gly Tyr Pro Gly Ser Gly Arg Asn Tyr Pro
                215                 220                 225
Gly Tyr Ser Pro Ser His Ile Pro His Ala Ser Gln Ser Arg Glu
                230                 235                 240
Thr Glu Tyr His His Arg Arg Leu Gln Lys Gln His Phe Cys Gly
                245                 250                 255
Arg Arg Lys Lys Tyr Ala Pro Lys Pro Thr Glu Asp Thr Tyr
                260                 265                 270
Leu Arg Phe Asp Glu Tyr Gly Ser Ser Gly Arg Pro Arg Ser
                275                 280                 285
Ala Gly Lys Ser Gln Lys Gly Leu Asn Val Glu Thr Leu Val Val
                290                 295                 300
Ala Asp Lys Lys Met Val Glu Lys His Gly Lys Gly Asn Val Thr
                305                 310                 315
Thr Tyr Ile Leu Thr Val Met Asn Met Val Ser Gly Leu Phe Lys
                320                 325                 330
Asp Gly Thr Ile Gly Ser Asp Ile Asn Val Val Val Ser Leu
                335                 340                 345
Ile Leu Leu Glu Gln Glu Pro Gly Gly Leu Leu Ile Asn His His
                350                 355                 360
Ala Asp Gln Ser Leu Asn Ser Phe Cys Gln Trp Gln Ser Ala Leu
                365                 370                 375
Ile Gly Lys Asn Gly Lys Arg His Asp His Ala Ile Leu Leu Thr
                380                 385                 390
Gly Phe Asp Ile Cys Ser Trp Lys Asn Glu Pro Cys Asp Thr Leu
                395                 400                 405
Gly Phe Ala Pro Ile Ser Gly Met Cys Ser Lys Tyr Arg Ser Cys
                410                 415                 420
Thr Ile Asn Glu Asp Thr Gly Leu Gly Leu Ala Phe Thr Ile Ala
                425                 430                 435
His Glu Ser Gly His Asn Phe Gly Met Ile His Asp Gly Glu Gly
                440                 445                 450
Asn Pro Cys Arg Lys Ala Glu Gly Asn Ile Met Ser Pro Thr Leu
                455                 460                 465
Thr Gly Asn Asn Gly Val Phe Ser Trp Ser Ser Cys Ser Arg Gln
                470                 475                 480
Tyr Leu Lys Lys Phe Leu Ser Thr Pro Gln Ala Gly Cys Leu Val
                485                 490                 495
Asp Glu Pro Lys Gln Ala Gly Gln Tyr Lys Tyr Pro Asp Lys Leu
                500                 505                 510
Pro Gly Gln Ile Tyr Asp Ala Asp Thr Gln Cys Lys Trp Gln Phe
                515                 520                 525
```

-continued

```
Gly Ala Lys Ala Lys Leu Cys Ser Leu Gly Phe Val Lys Asp Ile
            530                 535                 540
Cys Lys Ser Leu Trp Cys His Arg Val Gly His Arg Cys Glu Thr
            545                 550                 555
Lys Phe Met Pro Ala Ala Glu Gly Thr Val Cys Gly Leu Ser Met
            560                 565                 570
Trp Cys Arg Gln Gly Gln Cys Val Lys Phe Gly Glu Leu Gly Pro
            575                 580                 585
Arg Pro Ile His Gly Gln Trp Ser Ala Trp Ser Lys Trp Ser Glu
            590                 595                 600
Cys Ser Arg Thr Cys Gly Gly Val Lys Phe Gln Glu Arg His
            605                 610                 615
Cys Asn Asn Pro Lys Pro Gln Tyr Gly Gly Ile Phe Cys Pro Gly
            620                 625                 630
Ser Ser Arg Ile Tyr Gln Leu Cys Asn Ile Asn Pro Cys Asn Glu
            635                 640                 645
Asn Ser Leu Asp Phe Arg Ala Gln Gln Cys Ala Glu Tyr Asn Ser
            650                 655                 660
Lys Pro Phe Arg Gly Trp Phe Tyr Gln Trp Lys Pro Tyr Thr Lys
            665                 670                 675
Val Glu Glu Glu Asp Arg Cys Lys Leu Tyr Cys Lys Ala Glu Asn
            680                 685                 690
Phe Glu Phe Phe Phe Ala Met Ser Gly Lys Val Lys Asp Gly Thr
            695                 700                 705
Pro Cys Ser Pro Asn Lys Asn Asp Val Cys Ile Asp Gly Val Cys
            710                 715                 720
Glu Leu Val Gly Cys Asp His Glu Leu Gly Ser Lys Ala Val Ser
            725                 730                 735
Asp Ala Cys Gly Val Cys Lys Gly Asp Asn Ser Thr Cys Lys Phe
            740                 745                 750
Tyr Lys Gly Leu Tyr Leu Asn Gln His Lys Ala Asn Glu Tyr Tyr
            755                 760                 765
Pro Val Val Ile Ile Pro Ala Gly Ala Arg Ser Ile Glu Ile Gln
            770                 775                 780
Glu Leu Gln Val Ser Ser Ser Tyr Leu Ala Val Arg Ser Leu Ser
            785                 790                 795
Gln Lys Tyr Tyr Leu Thr Gly Gly Trp Ser Ile Asp Trp Pro Gly
            800                 805                 810
Glu Phe Pro Phe Ala Gly Thr Thr Phe Glu Tyr Gln Arg Ser Phe
            815                 820                 825
Asn Arg Pro Glu Arg Leu Tyr Ala Pro Gly Pro Thr Asn Glu Thr
            830                 835                 840
Leu Val Phe Glu Ile Leu Met Gln Gly Lys Asn Pro Gly Ile Ala
            845                 850                 855
Trp Lys Tyr Ala Leu Pro Lys Val Met Asn Gly Thr Pro Ala
            860                 865                 870
Thr Lys Arg Pro Ala Tyr Thr Trp Ser Ile Val Gln Ser Glu Cys
            875                 880                 885
Ser Val Ser Cys Gly Gly Tyr Ile Asn Val Lys Ala Ile Cys
            890                 895                 900
Leu Arg Asp Gln Asn Thr Gln Val Asn Ser Ser Phe Cys Ser Ala
            905                 910                 915
```

-continued

```
Lys Thr Lys Pro Val Thr Glu Pro Lys Ile Cys Asn Ala Phe Ser
            920                 925                 930
Cys Pro Ala Tyr Trp Met Pro Gly Glu Trp Ser Thr Cys Ser Lys
            935                 940                 945
Ala Cys Ala Gly Gly Gln Gln Ser Arg Lys Ile Gln Cys Val Gln
            950                 955                 960
Lys Lys Pro Phe Gln Lys Glu Glu Ala Val Leu His Ser Leu Cys
            965                 970                 975
Pro Val Ser Thr Pro Thr Gln Val Gln Ala Cys Asn Ser His Ala
            980                 985                 990
Cys Pro Pro Gln Trp Ser Leu Gly Pro Trp Ser Gln Cys Ser Lys
            995                 1000                1005
Thr Cys Gly Arg Gly Val Arg Lys Arg Glu Leu Leu Cys Lys Gly
            1010                1015                1020
Ser Ala Ala Glu Thr Leu Pro Glu Ser Gln Cys Thr Ser Leu Pro
            1025                1030                1035
Arg Pro Glu Leu Gln Glu Gly Cys Val Leu Gly Arg Cys Pro Lys
            1040                1045                1050
Asn Ser Arg Leu Gln Trp Val Ala Ser Ser Trp Ser Glu Val Leu
            1055                1060                1065
Ile Arg Ser His Cys Trp Val Arg Arg Leu Arg Pro Ser Trp Leu
            1070                1075                1080
Thr Gln
```

<210> SEQ ID NO 18
<211> LENGTH: 1187
<212> TYPE: DNA
<213> ORGANISM: Homo sapiens
<220> FEATURE:
<221> NAME/KEY: misc_feature
<223> OTHER INFORMATION: Incyte ID No: 6930294CB1

<400> SEQUENCE: 18

| | | | | | |
|---|---|---|---|---|---|
| ccgcaacctt | gaagcggcat | ccgtggagtg | cgcctgcgca | gctacgaccg | cagcaggaaa | 60 |
| gcgccgccgg | ccaggcccag | ctgtggccgg | acagggactg | gaagagagga | cgcggtcgag | 120 |
| taggtgtgca | ccagccctgg | caacgagagc | gtctaccccg | aactctgctg | gccttgaggt | 180 |
| tttaaaacat | gaatcctaca | ctcatccttg | ctgcctttg | cctgggaatt | gcctcagcta | 240 |
| ctctaacatt | tgatcacagt | ttagaggcac | agtggaccaa | gtggaaggcg | atgcacaaca | 300 |
| gattatacgg | catgaatgaa | gaaggatgga | ggagagcagt | gtgggagaag | aacatgaaga | 360 |
| tgattgaact | gcacaatcag | gaatacaggg | aagggaaaca | cagcttcaca | atggccatga | 420 |
| acgcctttgg | agacatgacc | agtgaagaat | tcaggcaggt | gatgaatggc | tttcaaaacc | 480 |
| gtaagcccag | gaaggggaaa | gtgttccagg | aacctctgtt | ttatgaggcc | cccagatctg | 540 |
| tggattggag | agagaaaggc | tacgtgactc | tgtgaagaa | tcagggtcag | tgtggttctt | 600 |
| gttgggcttt | tagtgctact | ggtgctcttg | aaggacagat | gttccggaaa | actgggaggc | 660 |
| ttatctcact | gagtgagcag | aatctggtag | actgctctgg | gcctcaaggc | aatgaaggct | 720 |
| gcaatggtgg | cctaatggat | tatgcttttcc | agtatgttca | ggatactgga | ggcctggact | 780 |
| ctgaggaatc | ctatccatat | gaggcaacag | aagaatcctg | taggtacaat | cccaagtatt | 840 |
| ctgctgctaa | tgacactggc | tttgtggaca | tcccttcaca | ggagaaggac | ctggcgaagg | 900 |
| cagtggcaac | tgtggggccc | atctctgttg | ctgctggtgc | aagccatgtc | tccttccagt | 960 |
| tctataaaaa | aggtatttat | tttgagccac | gctgtgaccc | cgaaggtctg | gatcatgcta | 1020 |

-continued

| | |
|---|---|
| tgctgctggt tggctacagc tatgaaggag cagactcaga taacaataaa tattggctgg | 1080 |
| tgaagaacag gtatggtaaa actgggggca tggatggcta cataaagatg gccaaagacc | 1140 |
| agaggaacaa ctgtggaatt gccacagcag ccagctaccc cactgtg | 1187 |

<210> SEQ ID NO 19
<211> LENGTH: 461
<212> TYPE: DNA
<213> ORGANISM: Homo sapiens
<220> FEATURE:
<221> NAME/KEY: misc_feature
<223> OTHER INFORMATION: Incyte ID No: 7473018CB1

<400> SEQUENCE: 19

| | |
|---|---|
| aagaattcgg cacgagggcc atggctgacc aactcttgcg taaaaagaga agaatttta | 60 |
| tccattcagt gggtgcaggc acaataaatg ccttgctgga ttgcctatta gaggatgaag | 120 |
| ttattagcca ggaagacatg aacaaagtga gagatgaaaa tgacactgtc atggataagg | 180 |
| ctcgagtctt gattgacctt gttactggaa aaggacccaa gtcttgctgc aaatttatca | 240 |
| agcatctctg tgaagaagac cctcaacttg cctcaaagat gggtttgcac taagagagaa | 300 |
| gatggaactc tggagcactt cagagacttc ccagagcttc ttccaaggga aagatattc | 360 |
| tcgtgaaaga aaaaaacaaa acaaaacaac agtgcttttt tcaaacctga ttaatttcat | 420 |
| caatttccaa taaatctttc attctctcaa aaaaaaaaaa a | 461 |

<210> SEQ ID NO 20
<211> LENGTH: 1884
<212> TYPE: DNA
<213> ORGANISM: Homo sapiens
<220> FEATURE:
<221> NAME/KEY: misc_feature
<223> OTHER INFORMATION: Incyte ID No: 7479221CB1

<400> SEQUENCE: 20

| | |
|---|---|
| atgtcccagc tctcctccac cctgaagcgc tacacagaat cggcccgcta cacagatgcc | 60 |
| cactatgcca gtcgggcta tggtgcctac accccatcct cctatggggc caatctggct | 120 |
| gcctccttac tggagaagga gaaacttggt ttcaagccgg tccccaccag cagcttcctc | 180 |
| acccgtcccc gtacctatgg cccctcctcc ctcctggact atgaccgggg ccgcccctg | 240 |
| ctgagacccg acatcactgg gggtggtaag cgggcagaga gccagacccg ggtactgag | 300 |
| cggcctttag gcagtggcct cagcgggggc agcggattcc cttatggagt gaccaacaac | 360 |
| tgcctcagct acctgcccat caatgcctat gaccaggggg tgaccctaac ccagaagctg | 420 |
| gacagccaat cagacctggc ccgggatttc tccagcctcc ggacctcaga tagctaccgg | 480 |
| atagacccca ggaacctggg ccgcagcccc atgctggccc ggacgcgcaa ggagctctgc | 540 |
| accctgcagg ggctctacca gacagccagc tgccctgaat acctggtcga ctacctggag | 600 |
| aactatggtc gcaagggcag tgcatctcag gtgccctccc aggcccctcc ctcacgagtc | 660 |
| cctgaaatca tcagcccaac ctaccgaccc attggccgct acacgctgtg ggagacggga | 720 |
| aagggtcagg ccccctgggcc cagccgctcc agctcccgg gaagagacgg catgaattct | 780 |
| aagagtgccc aggtctggc tggtcttcga aaccttggga acacgtgctt catgaactca | 840 |
| attctgcagt gcctgagcaa cactcgggag ttgagagatt actgcctcca gaggctctac | 900 |
| atgcgggacc tgcaccacgg cagcaatgca cacacagccc tcgtggaaga gtttgcaaaa | 960 |
| ctaattcaga ccatatggac ttcatccccc aatgatgtgg tgagcccatc tgagttcaag | 1020 |

-continued

| | |
|---|---|
| acccagatcc agagatatgc accgcgcttt gttggctata atcagcagga tgctcaggag | 1080 |
| ttccttcgct ttcttctgga tgggctccat aacgagtgtga accgagtgac actgagacct | 1140 |
| aagtccaacc ctgagaacct cgatcatctt cctgatgacg agaaaggccg acagatgtgg | 1200 |
| agaaaatatc tagaacggga agacagtagg atcgggatc tctttgttgg gcagctaaag | 1260 |
| agctcgctga cgtgtacaga ttgtggttac tgttctacgg tcttcgaccc cttctgggac | 1320 |
| ctctcactgc ccattgctaa gcgaggttat cctgaggtga cattaatgga ctgcatgagg | 1380 |
| ctcttcacca agaggatgt gcttgatgga gatgaaaagc caacatgctg tcgctgccga | 1440 |
| ggcagaaaac ggtgtataaa gaagttctcc atccagaggt tcccaaagat cttggtgctc | 1500 |
| catctgaagc ggttctcaga atccaggatc cgaaccagca agctcacaac atttgtgaac | 1560 |
| ttcccccctaa gagacctgga cttaagaaa tttgcctcag aaaacaccaa ccatgctgtt | 1620 |
| tacaacctgt acgctgtgtc caatcactcc ggaaccacca tgggtggcca ctatacagcc | 1680 |
| tactgtcgca gtccagggac aggagaatgg cacactttca acgactccag cgtcactccc | 1740 |
| atgtcctcca gccaagtgcg caccagcgac gcctacctgc tcttctacga actggccagc | 1800 |
| ccgcccctccc gaatgtagcg ccaggagcca cgtcccttct cccttccccg tggtggcccc | 1860 |
| gctccctaaa ttttttaaaa aaac | 1884 |

<210> SEQ ID NO 21
<211> LENGTH: 2576
<212> TYPE: DNA
<213> ORGANISM: Homo sapiens
<220> FEATURE:
<221> NAME/KEY: misc_feature
<223> OTHER INFORMATION: Incyte ID No: 2923874CB1

<400> SEQUENCE: 21

| | |
|---|---|
| tagacaaaag aaaaatccaa agggaaaatg ctgatctctg gaatactttg gacattcatg | 60 |
| catcaaaagc caactgcaag ccactatttg caagtcaagt ctcaagatgg tatactatct | 120 |
| ccaggaaaag gcttggaaga tacagatgtg gtgtataaaa gcgagaatgg acatgtcatt | 180 |
| aaactgaata tagaaacaaa tgctaccaca ttattattgg aaaacacaac ttttgtaacc | 240 |
| ttcaaagcat caagacattc agtttcacca gatttaaaat atgtccttct ggcatatgat | 300 |
| gtcaaacaga ttttttcatta ttcgtatact gcttcatatg tgatttacaa catacacact | 360 |
| agggaagttt gggagttaaa tcctccagaa gtagaggact ccgtcttgca gtacgcggcc | 420 |
| tggggtgtcc aagggcagca gctgatttat attttttgaaa ataatatcta ctatcaacct | 480 |
| gatataaaga gcagttcatt gcgactgaca tcttctggaa aagaagaaat aatttttaat | 540 |
| gggattgctg actggttata tgaagaggaa ctcctgcatt ctcacatcgc ccactggtgg | 600 |
| tcaccagatg gagaaagact tgccttcctg atgataaatg actctttggt acccaccatg | 660 |
| gttatccctc ggtttactgg agcgttgtat cccaaaggaa agcagtatcc gtatcctaag | 720 |
| gcaggtcaag tgaacccaac aataaaatta tatgttgtaa acctgtatgg accaactcac | 780 |
| actttggagc tcatgccacc tgacagcttt aaatcaagag aatactatat cactatggtt | 840 |
| aaatgggtaa gcaataccaa gactgtggta agatggttaa accgacctca gaacatctcc | 900 |
| atcctcacag tctgtgagac cactacaggt gcttgtagta aaaatatga gatgacatca | 960 |
| gatacgtggc tctctcagca gaatgaggag cccgtgtttt ctagagacgg cagcaaattc | 1020 |
| tttatgacga tgcctgttaa gcaaggggga cgtggagaat tcaccacat agctatgttc | 1080 |
| ctcatccaga gtaaaagtga gcaaattacc gtgcggcatc tgcatcagg aaactgggaa | 1140 |

-continued

```
gtgataaaga tcttggcata cgatgaaact actcaaaaaa tttactttct gagcactgaa     1200
tcttctccca gaggaaggca gctgtacagt gcttctactg aaggattatt gaatcgccaa     1260
tgcatttcat gtaatttcat gaaagaacaa tgtacatatt ttgatgccag ttttagtccc     1320
atgaatcaac atttcttatt attctgtgaa ggtccaaggg tcccagtggt cagcctacat     1380
agtacggaca acccagcaaa atattttata ttggaaagca attctatgct gaaggaagct     1440
atcctgaaga agaagatagg aaagccagaa attaaaatcc ttcatattga cgactatgaa     1500
cttcctttac agttgtccct tcccaaagat tttatggacc gaaaccagta tgctcttctg     1560
ttaataatgg atgaagaacc aggaggccag ctggttacag ataagttcca tattgactgg     1620
gattccgtac tcattgacat ggataatgtc attgtagcaa gatttgatgg cagaggaagt     1680
ggattccagg gtctgaaaat tttgcaggag attcatcgaa gattaggttc agtagaagta     1740
aaggaccaaa taacagctgt gaaattttg ctgaaactgc cttacattga ctccaaaaga     1800
ttaagcattt ttggaaaggg ttatggtggc tatattgcat caatgatctt aaaatcagat     1860
gaaaagcttt ttaaatgtgg atccgtggtt gcacctatca cagacttgaa attgtatgcc     1920
tcagctttct ctgaaagata ccttgggatg ccatctaagg aagaaagcac ttaccaggca     1980
gccagtgtgc tacataatgt tcatggcttg aaagaagaaa atatattaat aattcatgga     2040
actgctgaca caaagttca tttccaacac tcagcagaat taatcaagca cctaataaaa     2100
gctggagtga attatactat gcaggtctac ccagatgaag gtcataacgt atctgagaag     2160
agcaagtatc atctctacag cacaatcctc aaattcttca gtgattgttt gaaggaagaa     2220
atatctgtgc taccacagga accagaagaa gatgaataat ggaccgtatt tatacagaac     2280
tgaagggaat attgaggctc aatgaaacct gacaagagac tgtaatattg tagttgctcc     2340
agaatgtcaa gggcagctta cggagatgtc actggagcag cacgctcaga gacagtgaac     2400
tagcatttga atacacaagt ccaagtctac tgtgttgcta ggggtgcaga acccgttct     2460 ttgtatgaga gaggtcaagg gttggtttcc tgggagaaat tagttttgca ttaaagtagg     2520
agtagtgcat gtttttcttct gttatccccc tgtttgttct gtaactagtt ctctca        2576
```

<210> SEQ ID NO 22
<211> LENGTH: 2000
<212> TYPE: DNA
<213> ORGANISM: Homo sapiens
<220> FEATURE:
<221> NAME/KEY: misc_feature
<223> OTHER INFORMATION: Incyte ID No: 55122335CB1

<400> SEQUENCE: 22

```
gctctgcggc catggcgagc ggcgagcatt cccccggcag cggcgcggcc cggcggccgc       60
tgcactccgc gcaggctgtg gacgtggcct cggcctccaa cttccgggcc tttgagctgc      120
tgcacttgca cctggacctg cgggctgagt tcgggcctcc agggcccggc gcagggagcc      180
gggggctgag cggcaccgcg gtcctggacc tgcgctgcct ggagcccgag ggcgccgccg      240
agctgcggct ggactcgcac ccgtgcctgg aggtgacggc ggcggcgctg cggcgggagc      300
ggcccggctc ggaggagccg cctgcggagc ccgtgagctt ctacacgcag cccttctcgc      360
actatgccca ggccctgtgc gtgtccttcc cgcagccctg ccgcgccgcc gagcgcctcc      420
aggtgctgct cacctaccgc gtcggggagg gacccggggt tgctggttg gctcccgagc      480 agacagcagg aaagaagaag cccttcgtgt acacccaggg ccaggctgtc ctaaaccggg      540
ccttcttccc ttgcttcgac acgcctgctg ttaaatacaa gtattcagct cttattgagg      600
```

-continued

```
tcccagatgg cttcacagct gtgatgagtg ctagcacctg ggagaagaga ggtccaaata      660
agttcttctt ccagatgtgt cagcccatcc cctcctatct gatagctttg gccatcggag      720
atctggtttc ggctgaagtt ggacccagga gccgggtgtg ggctgagccc tgcctgattg      780
atgctgccaa ggaggagtac aacggggtga tagaagaatt tttggcaaca ggagagaagc      840 ttttggacc ttatgtttgg ggaaggtatg acttgctctt catgccaccg tcctttccat       900
ttggaggaat ggagaaccct tgtctgacct ttgtcacccc ctgcctgcta gctgggacc       960 gctccttggc agatgtcatc atccatgaga tctcccacag ttggtttggg aacctggtca     1020
ccaacgccaa ctgggtgaa ttctggctca atgaaggttt caccatgtac gcccagagga     1080
ggatctccac catcctcttt ggcgctgcgt acacctgctt ggaggctgca acggggcggg     1140
ctctgctgcg tcagcacatg gacatcactg gagaggaaaa cccactcaac aagctccgcg     1200
tgaagattga accaggcgtt gacccggacg acacctataa tgagaccccc tacgagaaag     1260
gtttctgctt tgtctcatac ctggcccact tggtgggtga tcaggatcag tttgacagtt     1320
ttctcaaggc ctatgtgcat gaattcaaat tccgaagcat cttagccgat gactttctgg     1380
acttctactt ggaatatttc cctgagctta agaaaaagag agtggatatc attccaggtt     1440
ttgagtttga tcgatggctg aataccccg gctggccccc gtacctccct gatctctccc       1500
ctggggactc actcatgaag cctgctgaag agctagccca actgtgggca gccgaggagc     1560
tggacatgaa ggccattgaa gccgtggcca tctctccctg gaagacctac cagctggtct     1620
acttcctgga taagatcctc cagaaatccc ctctccctcc tgggaatgtg aaaaaacttg     1680
gagacacata cccaagtatc tcaaatgccc ggaatgcaga gctccggctg cgatggggcc     1740
aaatcatcct taagaacgac caccaggaag atttctggaa agtgaaggag ttcctgcata     1800
accaggggaa gcagaagtat acacttccgc tgtaccacgc aatgatgggt ggcagtgagg     1860
tggcccagac cctcgccaag gagacttttg catccaccgc ctcccagctc acagcaatg      1920 ttgtcaacta tgtccagcag atcgtggcac ccaagggcag ttagaggctc gtgtgcatgg     1980
cccctgcctc ttcaggctct                                                 2000
```

<210> SEQ ID NO 23
<211> LENGTH: 3522
<212> TYPE: DNA
<213> ORGANISM: Homo sapiens
<220> FEATURE:
<221> NAME/KEY: misc_feature
<223> OTHER INFORMATION: Incyte ID No: 7473550CB1

<400> SEQUENCE: 23

```
ggagggagga cgtgcgaggc cggtgcgtgg aggctatggg cctgctggcc agtgctggtt       60
tgttgctgtt gctggtcatc ggccaccca gaagcctagg actgaagtgt ggaattcgca      120
tggtcaacat gaaaagtaag gaacctgccg tgggatctag attcttctct agaattagta      180
gttggagaaa ttcaacagtg actggacatc catggcaggt ctacctaaaa tcagatgagc      240
accacttctg tggaggaagc ttgattcaag aagatcgggt tgttacagca gcacactgcc      300
tgcacagcct cagtgagaag cagctgaaga atataactgt gacttctggg gagtacagcc      360
tctttcagaa ggataagcaa gaacagaata ttcctgtctc aaaaattatt acccatcctg      420
aatacaacag ccgtgaatat atgagtcctg atattgcact gctgtatcta aaacacaaag      480
tcaagtttgg aaatgctgtt cagccaatct gtcttcctga cagcgatgat aaagttgaac      540
caggaattct ttgcttatcc agtggatggg gcaagatttc caaacatca gaatattcaa       600
```

```
atgtcctaca agaaatggaa cttcccatca tggatgacag agcgtgtaat actgtgctca    660
agagcatgaa cctccctccc ctgggaagga ccatgctgtg tgctggcttc cctgattggg    720
gaatggacgc ctgccagggg gactctggag gaccactggt ttgtagaaga ggtggtggaa    780
tctggattct tgctgggata acttcctggg tagctggttg tgctggaggt tcagttcccg    840
taagaaacaa ccatgtgaag gcatcacttg gcattttctc caaagtgtct gagttgatgg    900
attttatcac tcaaaacctg ttcacaggtt tggatcgggg ccaacccctc tcaaaagtgg    960
gctcaaggta tataacaaag gccctgagtt ctgtccaaga agtgaatgga agccagagag   1020
ataaaataat cctgataaaa tttacaagtt tagacatgga aaagcaagtt ggatgtgatc   1080
atgactatgt atctttacga tcaagcagtg gagtgctttt tagtaaggtc tgtggaaaaa   1140
tattgccttc accattgctg gcagagacca gtgaggccat ggttccattt gtttctgata   1200
cagaagacag tggcagtggc tttgagctta ccgttactgc tgtacagaag tcagaagcag   1260
ggtcaggttg tgggagtctg gctatattgg tagaagaagg gacaaatcac tctgccaagt   1320
atcctgattt gtatcccagt aacacaaggt gtcattggtt catttgtgct ccagagaagc   1380
acattataaa gttgacattt gaggactttg ctgtcaaatt tagtccaaac tgtatttatg   1440
atgctgttgt gatttacggt gattctgaag aaaagcacaa gttagctaaa ctttgtggaa   1500
tgttgaccat cacttcaata ttcagttcta gtaacatgac ggtgatatac tttaaaagtg   1560
atggtaaaaa tcgtttacaa ggcttcaagg ccagatttac cattttgccc tcagagtctt   1620
taaacaaatt tgaaccaaag ttacctcccc aaaacaatcc tgtatctacc gtaaaagcta   1680
ttctgcatga tgtctgtggc atccctccat ttagtcccca gtggctttcc agaagaatcg   1740
caggagggga agaagcctgc ccccactgtt ggccatggca ggtgggtctg aggtttctag   1800
gcgattacca atgtggaggt gccatcatca acccagtgtg gattctgacc gcagcccact   1860
gtgtgcaatt gaagaataat ccactctcct ggactattat tgctggggac catgacagaa   1920
acctgaagga atcaacagag caggtgagaa gggccaaaca cataatagtg catgaagact   1980
ttaacacact aagttatgac tctgacattg ccctaataca actaagctct cctctggagt   2040
acaactcggt ggtgaggcca gtatgtctcc cacacagcgc agagcctcta ttttcctcgg   2100
agatctgtgc tgtgaccgga tggggaagca tcagtgcaga gctctctctg aatgtttctt   2160
cattagatgg tggcctagca agtcgcctac agcagattca agtgcatgtg ttagaaagag   2220
aggtctgtga acacacttac tattctgccc atccaggagg gatcacagag aagatgatct   2280
gtgctggctt tgcagcatct ggagagaaag atttctgcca gggagactct ggtgggccac   2340
tagtatgtag acatgaaaat ggtccctttg tcctctatgg cattgtcagc tggggagctg   2400
gctgtgtcca gccatggaag ccgggtgtat tgccagagt gatgatcttc ttggactgga   2460
tccaatcaaa aatcaatggt aaattgtttt caaatgttat taaaacaata acctctttct   2520
ttagagtggg tttgggaaca gtgagttgtt gctctgaagc agagctagaa aagcctagag   2580
gcttttttcc cacaccacgg tatctactgg attatagagg aagactggaa tgttcttggg   2640
tgctcagagt ttcagcaagc agtatggcaa aatttaccat tgagtatctg tcactcctgg   2700
ggtctcctgt gtgtcaagac tcagttctaa ttatttatga agaaagacac agtaagagaa   2760
agacggcagg taatccttcc tggcatttgc caatggagat tagtagcccc tttaaatcac   2820
atcattcagc ttaatattat taacttcccg atgaagccaa caacttttgt ctgtcatggt   2880
catctgcgtg tttacgaagg atttggacca ggaaaaaaat taataggttt ctcaaggatg   2940
tccagtattg gatttgattc cagtgacttc tgttgagatc acatctcttg attatcctaa   3000
```

| | |
|---|---|
| cagttaactc aacatgctga attacacttg gactttttat tccacaacag taaataaaat | 3060 |
| gaaggccatg attaaagact ttataacaga agaatctttg aactgtgatt gggattatat | 3120 |
| aatatttatg atagaccata tcagcaatca attctacttt ttatgtcatt gcacagaaaa | 3180 |
| agtactttaa ttatcgaata tgtctttcat tgcagctcat ttacatggct ccaagaaaga | 3240 |
| gtttatcttg atatccagtg ctgcttacct gactgtgcat tttaagactg atgagtctaa | 3300 |
| ggttggttgg tagctgtgct gcatctgcaa tgtcatggcc ctggctagtt agtctgcagc | 3360 |
| acgggagatt ctggaagacc accgcaatgt gcccggcatg ggaagtacaa gcttgttgac | 3420 |
| attgtgagct gaggcagcag tcactgccat cccactgcac caccttcaca agaatttctg | 3480 |
| cctgcaggga ttggatcaca tctgccacta gaggagaagt ga | 3522 |

<210> SEQ ID NO 24
<211> LENGTH: 3277
<212> TYPE: DNA
<213> ORGANISM: Homo sapiens
<220> FEATURE:
<221> NAME/KEY: misc_feature
<223> OTHER INFORMATION: Incyte ID No: 7478108CB1

<400> SEQUENCE: 24

| | |
|---|---|
| ccggtccctg ccatggggcc cccttccagc tcaggcttct atgtgagccg cgcagtggcc | 60 |
| ctgctgctgg ctgggttggt agccgccctc ctgctggcgc tggccgtact cgccgccttg | 120 |
| tacggccact gcgagcgcgt cccaccgtcg gagctgcctg gactcaggga ctcggaagcc | 180 |
| gagtcttccc ctcccctcag gcagaagccg acgccgaccc cgaaacccag cagtgcacgc | 240 |
| gagctagcgg tgacgaccac cccgagcaac tggcgacccc cggggccctg ggaccagcta | 300 |
| cgcctgccgc cctggctcgt gccgctgcac tacgatctgg agctgtggcc gcagctgagg | 360 |
| cccgacgagc ttccggccgg gtcttttgccc ttcactggcc gcgtgaacat cacggtgcgc | 420 |
| tgcacggtgg ccacctctcg actgctgctg catagcctct tccaggactg cgagcgcgcc | 480 |
| gaggtgcggg gaccccttc cccgggcact gggaacgcca cagtgggccg cgtgcccgtg | 540 |
| gacgacgtgt ggttcgcgct ggacacggaa tacatggtgc tggagctcag tgagcccctg | 600 |
| aaacctggta gcagctacga gctgcagctt agcttctcgg gcctggtgaa ggaagacctc | 660 |
| agggagggac tcttcctcaa cgtctacacc gaccagggcg agcgcagggc cctgttagcg | 720 |
| tcccagctgg aaccaacatt tgccaggtat gttttcccctt gttttgatga gccagctctg | 780 |
| aaggcaactt ttaatattac aatgattcat catccaagtt atgtggccct ttccaacatg | 840 |
| ccaaagctag gtcagtctga aaagaagat gtgaatggaa gcaaatggac tgttacaacc | 900 |
| ttttccacta cgccccacat gccaacttac ttagtcgcat ttgttatatg tgactatgac | 960 |
| cacgtcaaca gaacagaaag gggcaaggag atacgcatct gggcccggaa agatgcaatt | 1020 |
| gcaaatggaa gtgcagactt tgctttgaac atcacaggtc ccatcttctc tttttctggag | 1080 |
| gatttgttta atatcagtta ctctcttcca aaaacagata taattgcctt gcctagtttt | 1140 |
| gacaaccatg caatgcaaaaa ctggggacta atgatatttg atgaatcagg attgttgttg | 1200 |
| gaaccaaaag atcaactgac agaaaaaaag actctgatct cctatgttgt ctcccacgag | 1260 |
| attgacacc agtggtttgg aaacttggtt accatgaatt ggtggaacaa tatctggctc | 1320 |
| aacgagggtt ttgcatctta ttttgagttt gaagtaatta actactttaa tcctaaactc | 1380 |
| ccaagaaatg agatcttttt ttctaacatt ttacataata tcctcagaga agatcacgcc | 1440 |
| ctggtgacta gagctgtggc catgaaggtg gaaaatttca aaacaagtga aatacaggaa | 1500 |

-continued

| | |
|---|---|
| ctctttgaca tatttactta cagcaaggga gcgtctatgg cccggatgct ttcttgtttc | 1560 |
| ttgaatgagc atttatttgt cagtgcactc aagtcatatt tgaagacatt ttcctactca | 1620 |
| aacgctgagc aagatgatct atggaggcat tttcaaatgg ccatagatga ccagagtaca | 1680 |
| gttattttgc cagcaacaat aaaaaacata atggacagtt ggacacacca gagtggtttt | 1740 |
| ccagtgatca ctttaaacgt gtctactggc gtcatgaaac aggagccatt ttatcttgaa | 1800 |
| aacattaaaa atcggactct tctaaccagc aatgacacat ggattgtccc tattctttgg | 1860 |
| ataaaaaatg gaactacaca acctttagtc tggctagatc aaagcagcaa agtattccca | 1920 |
| gaaatgcaag tttcagattc tgaccatgac tgggtgattt tgaatttgaa tatgactgga | 1980 |
| tattatagag ttaattatga taaattaggt tggaagaaac taaatcaaca acttgaaaag | 2040 |
| gatcctaagg ctattcctgt tattcacaga ctgcagttca ttgatgatgc cttttccttg | 2100 |
| tctaaaaaca attatattga gattgaaaca gcacttgagt taaccaagta ccttgctgaa | 2160 |
| gaagatgaaa ttatagtatg gcatacagtc ttggtaaact tggtaaccag ggatcttgtt | 2220 |
| tctgaggtga acatctatga tatatactca ttattaaaga ggtacctatt aaagagactt | 2280 |
| aatttaatat ggaatatttta ttcaactata attcgtgaaa atgtgttggc attacaagat | 2340 |
| gactacttag ctctaatatc actggaaaaa ctttttgtaa ctgcgtgttg gttgggcctt | 2400 |
| gaagactgcc ttcagctgtc aaaagaactt ttcgcaaaat gggtggatca tccagaaaat | 2460 |
| gaaataccctt atccaattaa agatgtggtt ttatgttatg gcattgcctt gggaagtgat | 2520 |
| aaagagtggg acatcttgtt aaatacttac actaatacaa caaacaaaga agaaaagatt | 2580 |
| caacttgctt atgcaatgag ctgcagcaaa gacccatgga tacttaacag atatatggag | 2640 |
| tatgccatca gcacatctcc attcacttct aatgaaacaa atataattga ggttgtggct | 2700 |
| tcatctgaag ttggccggta tgtcgcaaaa gacttcttag tcaacaactg gcaagctgtg | 2760 |
| agtaaaaggt atggaacaca atcattgatt aatctaatat atacaatagg gagaaccgta | 2820 |
| actacagatt tacagattgt ggagctgcag cagttttttca gtaacatgtt ggaggaacac | 2880 |
| cagaggatca gagttcatgc caacttacag acaataaaga atgaaaatct gaaaacaag | 2940 |
| aagctaagtg ccaggatagc tgcgtggcta aggagaaaca catagcttgt ggctatcttt | 3000 |
| cagcactcct cttgcatatt ataatgtagt ttgttcacag ttttgtcttc caatactttg | 3060 |
| tgagtctgga aaaccacaca ttttatttgt atttcagtca catttattac tcagagtgcc | 3120 |
| attcttctca tattgtcatg tttggccctg agggtgggtg attgctgaca attttgccaa | 3180 |
| tgctgctgta tttctgggaa agatgtcact tcatgttggg ttataatccc acagaattta | 3240 |
| ctttaaatgt cacgtaaaaa caaattcaaa aaaaaa | 3277 |

<210> SEQ ID NO 25
<211> LENGTH: 1254
<212> TYPE: DNA
<213> ORGANISM: Homo sapiens
<220> FEATURE:
<221> NAME/KEY: misc_feature
<223> OTHER INFORMATION: Incyte ID No: 7482021CB1

<400> SEQUENCE: 25

| | |
|---|---|
| atgcgcacct cgtacaccgt gaccctgccc gaggaccccc ccgccgcccc ctttcccgcc | 60 |
| ctcgccaagg agctgcggcc gcgctcccct ctctccccgt ccctgctgct ctccaccttc | 120 |
| gtggggctcc tgctcaacaa agccaagaat tctaagagtg cccagggtct ggctggtctt | 180 |
| cgaaaccttg ggaacacgtg cttcatgaac tcaattctgc agtgcctgag caacactcgg | 240 |

```
gagttgagag attactgcct ccagaggctc tacatgcggg acctgcacca cggcagcaat     300
gcacacacag ccctcgtgga agagtttgca aaactaattc agaccatatg gacttcatcc     360
cccaatgatg tggtgagccc atctgagttc aagacccaga tccagagata tgcaccgcgc     420
tttgttggct ataatcagca ggatgctcag gagttccttc gctttcttct ggatgggctc     480
cataacgagg tgaaccgagt gacactgaga cctaagtcca cccctgagaa cctcgatcat     540
cttcctgatg acgagaaagg ccgacagatg tggagaaaat atctagaacg ggaagacagt     600
aggatcgggt atctctttgt tgggcagcta aagagctcgc tgacgtgtac agattgtggt     660
tactgttcta cggtcttcga ccccttctgg gacctctcac tgcccattgc taagcgaggt     720
tatcctgagg tgacattaat ggactgcatg aggctcttca ccaaagagga tgtgcttgat     780
ggagatgaaa agccaacatg ctgtcgctgc cgaggcagaa acggtgtat aaagaagttc      840 tccatccaga ggttcccaaa gatcttggtg ctccatctga gcggttctc agaatccagg      900 atccgaacca gcaagctcac aacatttgtg aacttccccc taagagacct ggacttaaga    960
gaatttgcct cagaaaacac caaccatgct gtttacaacc tgtacgctgt gtccaatcac   1020
tccggaacca ccatgggtgg ccactataca gcctactgtc gcagtccagg gacaggagaa   1080
tggcacactt tcaacgactc cagcgtcact cccatgtcct ccagccaagt gcgcaccagc   1140
gacgcctacc tgctcttcta cgaactggcc agcccgccct cccgaatgta gcgccaggag   1200
ccacgtccct tctcccttcc ccgtggtggc cccgctccct aaatttttta aaaa          1254

<210> SEQ ID NO 26
<211> LENGTH: 1120
<212> TYPE: DNA
<213> ORGANISM: Homo sapiens
<220> FEATURE:
<221> NAME/KEY: misc_feature
<223> OTHER INFORMATION: Incyte ID No: 7482145CB1

<400> SEQUENCE: 26
cgcgtgtgga agcgcttccg ggcggtagca cgctgtgttg gcggcggctc cccgcttgcc      60
tcagctgcag cagcgggaag ctcggtggca agcccttgta gtcctgtgcg atggcgtctc    120
gatatgacag ggcgatcact gtcttctccc cagacggaca ccttttttcaa gttgaatatg   180 cccaggaagc ggtgaagaaa ggatccaccg cggtcggaat tcgaggtacc aatatagttg    240 ttcttgggggt agaaaaaaaa tctgttgcca agcttcaaga tgaaagaact gtgaggaaaa   300
tttgtgccct tgatgaccat gtctgcatgg cttttgcagg acttactgct gatgctagag    360
tagtaataaa cagagcccgt gtggagtgcc agagccataa gcttacggtt gaggacccag    420
tcactgtaga atacataact cgcttcatag caactttaaa gcagaaatat acccaaagca    480
atggacgaag acctttttggt atttctgcct taattgtagg ttttgatgat gatggtatct    540
caagattgta tcagacagat ccttctggta cttatcatgc ttggaaggca aatgcaatag    600
gccgaagtgc taaaactgtt cgagaatttc tagaaaagaa ttacacagaa gatgccatag    660 caagtgcacag tgaagctatc aagttagcaa taaaagcttt gctagaagtt gtccagtctg   720
gtggaaaaaa cattgaactt gctataataa gaagaaatca acctttgaag atgtttagtg    780
caaaagaagt tgaattatat gtaactgaaa tagaaaagga aaaggaagaa gcagagaaga    840
aaaaatcaaa gaaatctgtc taattcttag gatgaccact gggaggtctt aatgttttgt    900
tttattgtac tgcctgaggt tgtttagtga aattttagag gaaaacagtt attttgcagc    960
attacatgca gtacttgtgt gatgtttttga gaatgccaga tctgtggctg tcttcattct   1020
```

-continued

| | |
|---|---|
| attacatagt caaacatagg tttatgtgaa gattttcttt gaaagggat ttcagtaatt | 1080 |
| gttgagagca gtcataattc cacataagcc tgagactcta | 1120 |

<210> SEQ ID NO 27
<211> LENGTH: 4577
<212> TYPE: DNA
<213> ORGANISM: Homo sapiens
<220> FEATURE:
<221> NAME/KEY: misc_feature
<223> OTHER INFORMATION: Incyte ID No: 55022586CB1

<400> SEQUENCE: 27

| | |
|---|---|
| agtgatcact ataggcctg gttatctaat gctgctcgag cgcgcgcagt gtgctggaaa | 60 |
| gcgcggctgg gcgcctcggc catgactgcg gagctgcagc aggacgacgc ggccggcgcg | 120 |
| gcagacggcc acggctcgag ctgccaaatg ctgttaaatc aactgagaga atcacaggc | 180 |
| attcaggacc cttcctttct ccatgaagct ctgaaggcca gtaatggtga cattactcag | 240 |
| gcagtcagcc ttctcactga tgagagagtt aaggagccca gtcaagacac tgttgctaca | 300 |
| gaaccatctg aagtagaggg gagtgctgcc aacaaggaag tattagcaaa agttatagac | 360 |
| cttactcatg ataacaaaga tgatcttcag gctgccattg ctttgagtct actggagtct | 420 |
| cccaaaattc aagctgatgg aagagatctt aacaggatgc atgaagcaac ctctgcagaa | 480 |
| actaaacgct caaagagaaa acgctgtgaa gtctggggag aaaacccaa tcccaatgac | 540 |
| tggaggagag ttgatggttg gccagttggg ctgaaaaatg ttggcaatac atgttggttt | 600 |
| agtgctgtta ttcagtctct ctttcaattg cctgaatttc gaagacttgt tctcagttat | 660 |
| agtctgccac aaaatgtact tgaaaattgt cgaagtcata cagaaaagag aaatatcatg | 720 |
| tttatgcaag agcttcagta tttgtttgct ctaatgatgg gatcaaatag aaaatttgta | 780 |
| gacccgtctg cagccctgga tctattaaag ggagcattcc gatcatctga ggaacagcag | 840 |
| caagatgtga gtgaattcac acacaagctc ctggattggc tagaggacgc attccagcta | 900 |
| gctgttaatg ttaacagtcc caggaacaaa tctgaaaatc caatggtgca gctgttctat | 960 |
| ggtactttcc tgactgaagg ggttcgtgaa ggaaaaccct tttgtaacaa tgagaccttc | 1020 |
| ggccagtatc ctcttcaggt aaacggttat cgcaacttag acgagtgttt ggaaggggcc | 1080 |
| atggtggagg gtgatgttga gcttcttccc tccgatcact cggtgaagta tggacaagag | 1140 |
| cgttggttta caaagctacc tccagtgttg acctttgaac tctcaagatt tgagtttaat | 1200 |
| cagtcccttg ggcagccaga gaaaattcac aataagctgg aatttcctca gattatttat | 1260 |
| atggacaggt acatgtacag gagcaaggag cttattcgaa ataagagaga gtgtattcga | 1320 |
| aagttgaagg aggaaataaa aattctgcag caaaaattgg aaaggtatgt gaaatatggc | 1380 |
| tcaggcccag ctcggttccc gctcccggac atgctgaaat atgttattga atttgctagt | 1440 |
| acaaaacctg cctcagaaag ctgtccacct gaaagtgaca cacatatgac attaccactt | 1500 |
| tcttcagtgc actgctcggt ttctgaccag acatccaagg aaagtacaag tacagaaagc | 1560 |
| tcttctcagg atgttgaaag tacctttct tctcctgaag attctttacc caagtctaaa | 1620 |
| ccactgacat cttctcggtc ttccatggaa atgccttcac agccagctcc acgaacagtc | 1680 |
| acagatgagg agataaattt tgttaagacc tgtcttcaga gatggaggag tgagattgaa | 1740 |
| caagatatac aagatttaaa gacttgtatt gcaagtacta ctcagactat tgaacagatg | 1800 |
| tactgcgatc ctctccttcg tcaggtgcct tatcgcttgc atgcagttct tgttcatgaa | 1860 |
| ggacaagcaa atgctggaca ctattgggcc tatatctata atcaaccccg acagagctgg | 1920 |

```
ctcaagtaca atgacatctc tgttactgaa tcttcctggg aagaagttga aagagattcc   1980
tatggaggcc tgagaaatgt tagtgcttac tgtctgatgt acattaatga caaactaccc   2040
tacttcaatg cagaggcagc cccaactgaa tcagatcaaa tgtcagaagt ggaagcccta   2100
tctgtggaac tcaagcatta cattcaggag gataactggc ggtttgagca ggaagtagag   2160
gagtgggaag aagagcagtc ttgcaaaatc cctcaaatgg agtcctccac caactcctca   2220
tcacaggact actctacatc acaagagcct tcagtagcct cttctcatgg ggttcgctgc   2280
ttgtcatctg agcatgctgt gattgtaaag gagcaaactg cccaggctat tgcaaacaca   2340
gcccgtgcct atgagaagag cggtgtagaa gcggcactga gtgaggcatt ccatgaagaa   2400
tactccaggc tctatcagct tgccaaagag acccccacct ctcacagtga tcctcgactt   2460
cagcatgtcc ttgtctactt tttccaaaat gaagcaccca aagggtagt agaacgaacc    2520 cttctggaac agtttgcaga taaaaatctt agctatgatg aaagatcaat cagcattatg   2580
aaggtggctc aagcgaaact gaaggaaatt ggtccagatg acatgaatat ggaagagtac   2640
aagaagtggc atgaagatta tagttttgttc cgaaaagtgt ctgtgtatct cctaacaggc   2700
ctagaactct atcaaaaagg aaagtaccaa gaggcacttt cctacctggt atatgcctac   2760
cagagcaatg ctgccctgct gatgaagggg ccccgccggg gggtcaaaga atccgtgatt   2820
gctttatacc gaagaaaatg ccttctggag ctgaatgcca agcagcttc tctttttgaa    2880 acaaatgatg atcactccgt aactgagggc attaatgtga tgaatgaact gatcatcccc   2940
tgcattcacc ttatcattaa taatgacatt tccaaggatg atctggatgc cattgaggtc   3000
atgagaaacc attggtgctc ttaccttggg caagatattg cagaaaatct gcagctgtgc   3060
ctaggggagt ttctacccag acttctagat ccttctgcag aaatcatcgt cttgaaagag   3120
cctccaacta ttcgacccaa ttctccctat gacctatgta gccgatttgc agctgtcatg   3180
gagtcaattc agggagtttc aactgtgaca gtgaaataag ctcccacatg ttcaggcccc   3240
attctggttc ctggctgcct gcctcttgca cagaagttcg ttgtcatagt gctcaccttg   3300
ggaaaaggat taggtgggca cataagattc cgatcagacc ccaaccatgc tgcatgtgta   3360
aagaaggatt gaaaataaaa ttgcactttt taggtacaaa atcataaaag ctgtttcact   3420
agaaaaggca gaaagcagtg tattaaggtg ttgaattacg ccagaagacc tgaaatgcct   3480
tgtacctaca acaatgctta ggcttttcta agcctcttgc cacttttaaa attatccttc   3540
aggcataaat attttttgaca gcagaataga agaatgattc atgagaacct gaaccagatg   3600
aacagctact agttatttta tcaaatacag atgacattta aaaattctta actacaagag   3660
attagaaata taaaccttgc ctggctcttg ccaggagata acaaaatggg ttgctgatga   3720
actgcaccct tttacatgtg ggtagaatat aagctcacat ggcagtgaga tgttgaaaag   3780
tcaaaagaga cctgtctctc tcctttcttt tctatcttta aaccagaaaa cctcatactc   3840
agtcctcagt gaaagaaagt aaagtattaa ggactttaga cagaagagca ttgtgtaact   3900
tgactgaaga tcatccatta atagttatta ggcatttagg taaaattttc taatacctaa   3960
aaattgtcaa aaacagtcaa tagggctact gctggcccaa agaccattta ggtccacctc   4020 ctctttttttg ctcttttttt ttttctgtga cagtttcact gtgtcgccca ggctggcgtt   4080
cagtggtgca atctcagctc actgcaaact ctgtctcctg ggtcaagtg attctcgtgc    4140 ctcagcctcc cgaatagctg gaattacggg catgcaccac cacacctggc taattttttgt   4200 attttttaata gagatggggt ttcaccatat tggccaggct gatctctaac tcctggcctc   4260
```

| | |
|---|---|
| aagtgatcta tctgcctccc tcagcctccc aaagtctggg attgcagaca agtcatcgta | 4320 |
| cccggccttc ttttttgccc ttaaaagtaa gggatgtggg tttgtacaaa aaaaaaacaa | 4380 |
| aaaaaaaaag aggggcggcc gcgcgattat tgagtctctt gcaacccgcg aatttatttc | 4440 |
| cgaaccggtt acctgagggc gttcccagtt tcctaatggt gagtcgtttt acagcttgta | 4500 |
| gtaatcatga acaagctgtc ctgtgtgaat tgtttcgttc catccacata tcacacacac | 4560 |
| aacacggacg gaagacg | 4577 |

<210> SEQ ID NO 28
<211> LENGTH: 1952
<212> TYPE: DNA
<213> ORGANISM: Homo sapiens
<220> FEATURE:
<221> NAME/KEY: misc_feature
<223> OTHER INFORMATION: Incyte ID No: 3238072CB1

<400> SEQUENCE: 28

| | |
|---|---|
| aagtgctccc acgtggcctg cggccgctat attgaggacc acgccctgaa acactttgag | 60 |
| gagacgggac acccgctagc catggaagtc cgggatctct acgtgttctg ttacctgtgc | 120 |
| aaggactacg tgctcaatga taacccagag ggggacctga agctgctaag aagctccctc | 180 |
| ctggcggtcc ggggccagaa acaggacacg ccggtgagac gtgggcggac gctgcggtcc | 240 |
| atggcttcgg gtgaggacgt ggtcctgccg cagcgcgctc ctcagggaca gccgcagatg | 300 |
| ctcacggctc tgtggtaccg gcgtcagcgc ctgctggcca ggacgctgcg gctgtggttc | 360 |
| gagaagagct cccggggcca ggcgaagctg agcagcggc ggcaggagga ggccctggag | 420 |
| cgcaagaagg aggaggcgcg gaggcggcgg cgcgaggtga acggcggct gctggaggag | 480 |
| ctggccagca cccctccgcg caagagtgca cggctgctcc tgcacacgcc ccgcgacgcg | 540 |
| ggcccggctg cctcgcgccc cgccgccctc cctacctcac gcagagtgcc cgccgccaca | 600 |
| ctcaagctgc gtcgccagcc ggccatggcc caggcgtca cgggcctgcg caacctgggc | 660 |
| aacacctgct acatgaactc catcctccag gtgctcagcc acctccagaa gttccgagaa | 720 |
| tgtttcctca accttgaccc ttccaaaacg gaacatctgt ttcccaaagc caccaacggg | 780 |
| aagactcagc tttctggcaa gccaaccaac agctcggcca cggagctgtc cttgagaaat | 840 |
| gacagggccg aggcatgcga gcgggagggc ttctgctgga acggcagggc ctccattagt | 900 |
| cggagtctgg agctcatcca gaacaaggag ccgagttcaa agcacatttc cctctgccgt | 960 |
| gaactgcaca ccctcttccg agtcatgtgg tccgggaagt gggccctagt gtcgcccttc | 1020 |
| gccatgctgc actcagtgtg gagcctgatc cctgccttcc gcggctacga ccaacaggac | 1080 |
| gcgcaggaat ttctctgcga gctgctgcac aaggtgcagc aggaactcga gtctgagggc | 1140 |
| accacacgcc ggatcctcat ccccttctcc cagaggaagc tcaccaaaca ggtcttaaag | 1200 |
| gtggtgaata ccatatttca tgggcagctg ctcagtcagg tcacatgtat atcatgcaat | 1260 |
| tacaaatcca ataccattga gccctttggg gacctatccc tggaattccc tgaacgctat | 1320 |
| cactgcatag aaaaggggtt tgtcccttg aatcaaacag agtgcttgct cactgagatg | 1380 |
| ctggccaaat tcacagagac agaggccctg gaagggagaa tctacgcttg tgaccagtgt | 1440 |
| aacagcaaac gacgaaaatc caatcccaaa ccccttgttc tgagtgaagc tagaaagcag | 1500 |
| ttaatgatct acagactacc tcaggttctc cggctgcacc ttaaaagatt caggtggtct | 1560 |
| ggccgtaatc atcgagagaa gattggggtc catgtcgtct tgaccaggt attaaccatg | 1620 |
| gaaccttact gctgcaggga catgctctcc tctcttgaca aagagacctt tgcctatgat | 1680 |

-continued

| | |
|---|---|
| ctctccgcag tggtcatgca tcacgggaaa gggtttggct caggacacta cacagcctat | 1740 |
| tgctacaaca cagagggagg tttttgggtc cactgcaatg actcaaagct gaatgtatgc | 1800 |
| agtgtcgagg aagtgtgcaa aacccaggcc tacatccttt tttacactca aagaacagtg | 1860 |
| cagggcaatg caagaatctc agaaacccat ctccaagctc aggtgcagtc cagcaacaat | 1920 |
| gatgaaggca gaccacagac attttcctga at | 1952 |

<210> SEQ ID NO 29
<211> LENGTH: 1092
<212> TYPE: DNA
<213> ORGANISM: Homo sapiens
<220> FEATURE:
<221> NAME/KEY: misc_feature
<223> OTHER INFORMATION: Incyte ID No: 7482034CB1

<400> SEQUENCE: 29

| | |
|---|---|
| aaggggggctg ctccatcagc caatcccaaa gcctgaattg ggggttgagg agaaatgaag | 60 |
| cgtcagctca cacaccttcc tggccggttc tggctgtggc ccagcttctc tgtagcgtcc | 120 |
| ctcctatccc accagacccc agccacaaat tcctggcttg cttcttccaa acttcattca | 180 |
| gccccaggga tggctctgca ggatgtgtgc aagtggcagt cccctgacac ccagggacca | 240 |
| tcacctcacc tgcctcgggc tggcggctgg gctgtgcccc ggggttgtga ccctcaaacc | 300 |
| ttcctgcaga tccatggccc cagactggcc acggcacca ccactctggc cttccgcttc | 360 |
| cgtcatggag tcattgctgc agctgacacg cgttcctcct gtggcagcta tgtggcgtgt | 420 |
| ccagcctcat gcaaggtcat ccctgtgcac cagcacctcc tgggtaccac ctctggcacc | 480 |
| tctgccgact gtgctacctg gtatcgggta ttacagcggg agctgcggct tcgggaactg | 540 |
| agggagggtc agctgcccag tgtggccagt gctgccaagc tcttgtcagc catgatgtct | 600 |
| caataccggg gactggatct ctgtgtggcc actgccctct gcggctggga ccgctctggc | 660 |
| cctgagctct tctacgtcta tagcgacgg acccgcctgc aggggacat cttctctgtg | 720 |
| ggctctggat ctccctatgc ctacggcgtg ctagaccgtg gctatcgcta cgacatgagc | 780 |
| acccaggaag cctacgccct ggctcgctgc gccgtggccc acgccaccca ccgtgatgcc | 840 |
| tattcagggg gctctgtaga cctttttccac gtgcgggaga gtggatggga gcatgtgtca | 900 |
| cgcagtgatg cctgtgtgct gtacgtggag ttacagaagc tcctggagcc ggagccagag | 960 |
| gaggatgcca gccatgccca tcctgagcct gccactgccc acagagctgc agaagataga | 1020 |
| gagctctctg tggggccagg ggaggtgaca ccaggagact ccaggatgcc agcagggact | 1080 |
| gagacggtgt ga | 1092 |

<210> SEQ ID NO 30
<211> LENGTH: 2847
<212> TYPE: DNA
<213> ORGANISM: Homo sapiens
<220> FEATURE:
<221> NAME/KEY: misc_feature
<223> OTHER INFORMATION: Incyte ID No: 7474351CB1

<400> SEQUENCE: 30

| | |
|---|---|
| atggtcagca aggggggagt tgctgcagag ccagagccac actattgtga ggacagtgaa | 60 |
| agaggcccca acaccctcac aggtccgggc agccttccta gggaggtgg cattgaggtg | 120 |
| ggcatggagt ttccgggatg cagcggtgaa gggtgcgtga agccccatga ggaggcggcc | 180 |
| cgggaggggg cgggcagagg caagagggct gtgccgggac ccaagcgacg gcagcagggg | 240 |
| tcagcagagg ggcctgcggc ggggtggacg ctggagcagg agaccagggg agatgtctta | 300 |

-continued

```
gaggataaaa atgagcgggc agatgaagag atactcaggc tggcaccagg gaaaggcagg      360
ctcccaatag acagcaaaca cctgaaaccg gtgatcagca gcttcccggt aagatctcag      420
gagctgggcg aggggggctgg agcaggcaca ctaagaggca aaatggcaga gtttaactgg     480
tctatggcct tcaagggacc tgcggctggt catgaagagc gcctcaactc tgtgtccagc     540
agggccaaga aggggcattgg ctgggatgtc gctgctgctt ctcttcgtgg tgttgaccat   600
ttctcagacc tcccccccgcc cctgcaggtc agggaggagt tggaggcttg cgcgtttaga   660
gtgcaggtgg ggcagctgag gctctatgag gacgaccagc ggacgaaggt ggttgagatc    720
gtccgtcacc cccagtacaa cgagagcctg tctgcccagg gcggtgcgga catcgccctg   780
ctgaagctgg aggccccggt gccgctgtct gagctcatcc acccggtctc gctcccgtct    840
gcctccctgg acgtgccctc ggggaagacc tgctgggtga ccggctgggg tgtcattgga   900
cgtggagaac tactgccctg gcccctcagc ttgtgggagg cgacggtgaa ggtcaggagc    960
aacgtcctct gtaaccagac ctgtcgccgc cgctttcctt ccaaccacac tgagcggttt    1020
gagcggctca tcaaggacga catgctgtgt gccggggacg ggaaccacgg ctcctggcca     1080
ggcgacaacg ggggccccct cctgtgcagg cggaattgca cctgggtcca ggtggaggtg   1140
gtgagctggg gcaaactctg cggccttcgc ggctatcccg gcatgtacac ccgcgtgacg    1200
agctacgtgt cctggatccg ccagccatgc ccctcagctc agaccctgc tgtggtccga    1260 agatttgtgc tccccccaaa tccagatgtt gaagccctaa ctcccagtgt gatgggatca    1320
ggagcgccgc tgccccggc ccccgacctg caagaggccg aggtccccat catgaggacc    1380
cgagcttgcg agaggatgta tcacaaaggc cccactgccc acggccaggt caccatcatc    1440
aaggctgcca tgcgtgtgc agggaggaag gggcagggtt cctgccaggc cgctctgagg     1500
acggaggacc tcacccccaac cacacccaac acggaggtgt ctccacgtgc agaccccagg   1560
ctgagccagc cggaggacat ctggccagag tgggcttggc cagttgtggt gggcaccacc    1620
atgctgctgc tgctgctgtt cctggctgtc tcctccctgg ggagctgtag cactgggagt   1680
ccagctcccg tccccgagaa tgacctggtg ggcattgtgg ggggccacaa cacccccaggg   1740 gaagtggtcg tggcagtggg tgctgaccgc cgctcactgc attttccgga aggacaccga   1800
cccgtccacc taccggattc acaccaggga tgtgtatctg tacggggggcc gggggctgct   1860 gaatgtcagc cagatcgtcg tccacccaac tactctgtct tcttcctggg ggcagacatc   1920
gccctgctga agctggccac cagttccctg gagttcactg acagtgacaa ctgctggaac    1980
acaggctggg gcatggtcgg cttgttggat atgctgccgc ctccttaccg cccgcagcag    2040
gtgaaggtcc tcacactgag caatgcagac tgtgagcggc agacctacga tgctttttcct    2100 ggtgctggag acagaaagtt catccaggat gacatgatct gtgccggccg cacgggccgc    2160
cgcacctgga agggtgactc aggcggccccc ctggtctgca agaagaaggg tacctggctc    2220
caggcgggag tagtgagctg gggattttac agtgatcggc ccagcattgg cgtctacaca    2280
cgcccagaga ccagctggca gggtgccaac catgcagacg cccagagacc agctggcagg    2340
gtgccaacca tgcagaggcc cagagacatg ggccagggcc aggagtgggt ctgcaggccc     2400
ttcacccacg tcacctgcta cccgacggcc atccccaggc ccttcaccca tgtcacctgc    2460
tacctgatgg ctgtccccag cacctcacc cacgtcacct gctacccgac ggccgtcccc    2520 aggccccttca cccatgtcac ctgctacctg atggctgtcc ccagcacccct cacccacatc   2580 acctgctaca tgatggccgt ccccaggccc tttacccaca tcacctgcta cccaatggct    2640
```

```
gtccccagca cccttaccca cgtcacctgc cacccgacgg ccatcccag gcccttcacc    2700 cacatcacct gctacacgat ggccatcccc aggccttcaa ccacgccacc tgctacacga    2760
cggccatccc cagcaccctc acccacgtca cctgctacac gatggccgtc cccaggccca    2820
tcacccatgt cacctgctac acgatag                                       2847

<210> SEQ ID NO 31
<211> LENGTH: 1396
<212> TYPE: DNA
<213> ORGANISM: Homo sapiens
<220> FEATURE:
<221> NAME/KEY: misc_feature
<223> OTHER INFORMATION: Incyte ID No: 2232483CB1

<400> SEQUENCE: 31
gcccacgtga cgggcgcccg cggaaggcga catgggctcc gctccctggg ccccggtcct      60
gctgctggcg ctcgggctgc gcggcctcca ggcggggggcc cgcagggccc cggaccccgg    120
cttccaggag cgcttcttcc agcagcgtct ggaccacttc aacttcgagc gcttcggcaa    180
caggaccttc cctcagcgct tcctggtgtc ggacaggttc tgggtccggg gcgaggggcc    240
catcttcttc tacactggga acgagggcga cgtgtgggcc ttcgccaaca actcggcctt    300
cgtcgcggag ctggcggccg agcgggggc tctactggtc ttcgcggagc accgctacta    360
cgggaagtcg ctgccgttcg gtgcgcagtc cacgcagcgc gggcacacgg agctgctgac    420
ggtggagcag gccctggccg acttcgcaga gctgctccgc gcgctacgac gcgaccccgg    480
ggcccaggat gcccccgcca tcgccttcgg tggaagttat gggggggatgc tcagtgccta    540 cctgaggatg aagtatcccc acctggtggc ggggcgctg gcggccagcg cgcccgttct    600
agctgtggca ggcctcggcg actccaacca gttcttccgg gacgtcacgg cgggagccta    660
cgacacggtc cgctgggagt tcggcacctg ccagccgctg tcagacgaga aggacctgac    720
ccagctcttc atgttcgccc ggaatgcctt caccgtgctg gccatgatgg actaccccta    780
ccccactgac ttcctgggtc ccctccctgc caaccccgtc aaggtgggct gtgatcggct    840
gctgagtgag gcccagagga tcacgggcct gcgagcactg gcagggctgg tctacaacgc    900
ctcgggctcc gagcactgct acgacatcta ccggctctac cacagctgtg ctgaccccac    960
tggctgcggc accggccccg acgccagggc ctgggactac caggcctgca ccgagatcaa    1020
cctgaccttc gccagcaaca atgtgaccga tatgttcccc gacctgccct tcactgacga    1080
gctccggcca agcgatctca gagccgccag caacatcatc ttctccaacg ggaacctgga    1140
ccccctgtgg caggggcggga ttcggaggaa cctgagtgcc tcagtcatcg ccgtcaccat    1200
ccagggggga gcgcaccacc tcgacctcag agcctccac ccagaagatc ctgcttccgt    1260
ggttgaggcg cggaagctgg aggccaccat catcggcgag tgcgtaaagg cagccaggcg    1320
tgagcagcag ccagctctgc gttgggggc ccagatcagc ctctgagcac aggactggag    1380
gggtctcagg gctcta                                                    1396

<210> SEQ ID NO 32
<211> LENGTH: 1853
<212> TYPE: DNA
<213> ORGANISM: Homo sapiens
<220> FEATURE:
<221> NAME/KEY: misc_feature
<223> OTHER INFORMATION: Incyte ID No: 7481712CB1

<400> SEQUENCE: 32
tcagagctgc ctgcgagtcc tgcctgctca gggctccttc agcctccact catgcggtgc      60
```

-continued

| | |
|---|---|
| ctcctggcct ccccgcctgg ccctcagctg ggcctctgct ccactctgcc ccttccaagt | 120 |
| gacacagcct tccagggatc cttctccgca gcttcctccg cccctccctg tgtttttcta | 180 |
| gggaccaggt tcttcgagtc ctggccaaag atgagaagca gctttcactt ctcggggatc | 240 |
| tggagggcct gaaacccag aaggtggact tctggcgtgg cccagccagg cccagcctcc | 300 |
| ctgtggatat gagagttcct ttctccgaac tgaaagacat caaagcttat ctggagtctc | 360 |
| atggacttgc ttacagcatc atgataaagg acatccaggt gaagccctgc cccagctggg | 420 |
| accctgcctt ccgccttcct ttctggttgg gcccaacat ggaggagatg ttctcggggc | 480 |
| taaaagtgga catgtggttt ctgggtctcc atcagcgtgt ttgtgaacat gctgtggaag | 540 |
| gaacaggctg cccacccct cacttccacca aagcttccct cgacaatgtc acacgcaact | 600 |
| tccagatcca acccgatggc cgactctcaa tgttcctctt ccaacagcac aactggtcac | 660 |
| tctctccttc ctggagcctg tctcttcccc tggcatccag gacttctgtg ttctgtctcc | 720 |
| agccagcacc tcctctcctg gatccaaccg cctactcagt gtttccacct gggggtgcaa | 780 |
| tgggcatctc caactttcca gccccaggaa tggagcaaac gctggtgcat tttccaggcc | 840 |
| aaggcagatt cctgttcctg gaagtggggc cagctgtgct gctggatgag aaagacagg | 900 |
| ccatggcgaa atcccgccgg ctggagcgca gcaccaacag cttcagttac tcatcatacc | 960 |
| acaccctgga ggagatatat agctggattg acaactttgt aatggagcat tccgatattg | 1020 |
| tctcaaaaat tcagattggc aacagctttg aaaaccagtc cattcttgtc ctgaagttca | 1080 |
| gcactggagg ttctcggcac ccagccatct ggattgacac tggaattcac tcccgggagt | 1140 |
| ggatcaccca tgccaccggc atctggactg ccaataagat tgtcagtgat tatggcaaag | 1200 |
| accgtgtcct gacagacata ctgaatgcca tggacatctt catagagctc gtcacaaacc | 1260 |
| ctgatgggtt tgcttttacc cacagcatga accgcttatg gcggaagaac aagtccatca | 1320 |
| gacctggaat cttctgcatc ggcgtggatc tcaacaggaa ctggaagtcg ggttttggag | 1380 |
| gaaatggttc taacagcaac ccctgctcag aaacttatca cgggccctcc cctcagtcgg | 1440 |
| agccggaggt ggctgccata gtgaacttca tcacagccca tggcaacttc aaggctctga | 1500 |
| tctccatcca cagctactct cagatgctta tgtacccta cggccgattg ctggagcccg | 1560 |
| tttcaaatca gagggagttg tacgatcttg ccaaggatgc ggtggaggcc ttgtataagg | 1620 |
| tccatgggat cgagtacatt tttggcagca tcagcaccac cctctatgtg ccagtggga | 1680 |
| tcaccgtcga ctgggcctat gacagtggca tcaagtacgc cttcagcttt gagctccggg | 1740 |
| acactgggca gtatggcttc ctgctgccgg ccacacagat catccccacg gcccaggaga | 1800 |
| cgtggatggc gcttcggacc atcatggagc acaccctgaa tcacccctac tag | 1853 |

<210> SEQ ID NO 33
<211> LENGTH: 3344
<212> TYPE: DNA
<213> ORGANISM: Homo sapiens
<220> FEATURE:
<221> NAME/KEY: misc_feature
<223> OTHER INFORMATION: Incyte ID No: 8213480CB1

<400> SEQUENCE: 33

| | |
|---|---|
| atgggctgga ggccccggag agctcggggg acccgttgc tgctgctgct actactgctg | 60 |
| ctgctctggc cagtgccagg cgccggggtg cttcaaggac atatccctgg gcagccagtc | 120 |
| accccgcact gggtcctgga tgacaaccc tggcgcaccg tcagcctgga ggagccggtc | 180 |
| tcgaagccag acatggggct ggtggccctg gaggctgaag gccaggagct cctgcttgag | 240 |

-continued

```
ctggagaaga accacaggct gctggcccca ggatacatag aaacccacta cggcccagat      300
gggcagccag tggtgctggc ccccaaccac acggatcatt gccactacca agggcgagta      360
aggggcttcc ccgactcctg ggtagtcctc tgcacctgct ctgggatgag tggcctgatc      420
accctcagca ggaatgccag ctattatctg cgtccctggc caccccgggg ctccaaggac      480
ttctcaaccc acgagatctt tcggatggag cagctgctca cctggaaagg aacctgtggc      540
cacagggatc ctgggaacaa agcgggcatg accagccttc ctggtggtcc ccagagcagg      600
ggcaggcgag aagcgcgcag acccggaag tacctggaac tgtacattgt ggcagaccac      660
accctgttct tgactcggca ccgaaacttg aaccacacca acagcgtctc cctggaagtc      720
gccaactacg tggaccagct tctcaggact ctggacattc aggtggcgct gaccggcctg      780
gaggtgtgga ccgagcggga ccgcagccgc gtcacgcagg acgccaacgc cacgctctgg      840
gccttcctgc agtggcgccg gggactgtgg gcgcagcggc ccacgactc cgcgcagctg       900 ctcacgggcc gcgccttcca gggcgccaca gtgggcctgg cgcccgtcga gggcatgtgc      960
cgcgccgaga gctcgggagg cgtgagcacg gaccactcgg agctccccat cggcgccgca     1020
gccaccatgg cccatgagat cggccacagc ctcggcctca gccacgaccc cgacggctgc     1080
tgcgtggagg ctgcggccga gtccggaggc tgcgtcatgg ctgcggccac cgggcacccg     1140
tttccgcgcg tgttcagcgc ctgcagccgc gccagctgc gcgccttctt ccgcaagggg       1200
ggcggcgctt gcctctccaa tgccccggac cccggactcc cggtgccgcc ggcgctctgc     1260
gggaacggct tcgtggaagc gggcgaggag tgtgactgcg gccctggcca ggagtgccgc     1320
gacctctgct gctttgctca caactgctcg ctgcgcccgg gggcccagtg cgcccacggg     1380
gactgctgcg tgcgctgcct gctgaagccg gctggagcgc tgtgccgcca ggccatgggt     1440
gactgtgacc tcctgagtt ttgcacgggc acctcctccc actgtccccc agacgtttac      1500
ctactggacg gctcaccctg tgccagggc agtggctact gctgggatgg cgcatgtccc       1560
acgctggagc agcagtgcca gcagctctgg gggcctggct cccacccagc tcccgaggcc     1620
tgtttccagg tggtgaactc tgcgggagat gctcatggaa actgcggcca ggacagcgag     1680
ggccacttcc tgccctgtgc agggagggat gccctgtgtg ggaagctgca gtgccagggt     1740
ggaaagccca gcctgctcgc accgcacatg gtgccagtgg actctaccgt tcacctagat     1800
ggccaggaag tgacttgtcg gggagccttg gcactcccca gtgcccagct ggacctgctt     1860
ggcctgggcc tggtagagcc aggcacccag tgtggaccta aatggttg caatagcaac       1920 cataactgcc actgtgctcc aggctgggct ccaccttct gtgacaagcc aggctttggt      1980
ggcagcatgg acagtggccc tgtgcaggct gaaaaccatg acaccttcct gctggccatg     2040
ctcctcagcg tcctgctgcc tctgctccca ggcgccggcc tggcctggtg ttgctaccga     2100
ctcccaggag cccatctgca gcgatgcagc tggggctgca gaagggaccc tgcgtgcagt     2160 gccccaaag atggcccaca cagggaccac ccctgggcg gcgttcaccc cacggagttg       2220
ggccccacag ccactggaca gtcctggccc ctggaccctg agaactctca tgagcccagc     2280 agccacctg agaagcctct gccagcagtc tcgcctgacc cccaagcaga tcaagtccag      2340
atgccaagat cctgcctctg gtgagaggta gctcctaaaa tgaacagatt taaagacagg     2400
tggccactga cagccactcc aggaacttga actgcagggg cagagccagt gaatcaccgg     2460
acctccagca cctgcaggca gcttggaagt ttcttccccg agtggagctt cgacccaccc     2520
actccaggaa cccagagcca cattagaagt tcctgagggc tggagaacac tgctgggcac     2580
```

```
actctccagc tcaataaacc atcagtccca gaagcaaagg tcacacagcc cctgacctcc    2640
ctcaccagtg gaggctgggt agtgctggcc atcccaaaag ggctctgtcc tgggagtctg    2700
gtgtgtctcc tacatgcaat ttccacggac ccagctctgt ggagggcatg actgctggcc    2760
agaagctagt ggtcctgggg ccctatggtt cgactgagtc cacactcccc tgcagcctgg    2820
ctggcctctg caaacaaaca taattttggg gaccttcctt cctgtttctt cccaccctgt    2880
cttctcccct aggtggttcc tgagccccca ccccaatcc cagtgctaca cctgaggttc     2940
tggagctcag aatctgacag cctctccccc attctgtgtg tgtcgggggg acagagggaa    3000
ccatttaaga aaagatacca aagtagaagt caaaagaaag acatgttggc tataggcgtg    3060
gtggctcatg cctataatcc cagcactttg ggaagccggg gtaggaggat caccagaggc    3120
cagcaggtcc acaccagcct gggcaacaca gcaagacacc gcatctacag aaaaatttta    3180
aaattagctg ggcgtggtgg tgtgtacctg taggcctagc tgctcaggag gctgaagcag    3240
gaggatcact tgagcctgag ttcaacactg cagtgagcta tggtggcacc actgcactcc    3300
agcctgggtg acagagcaag accatgtctc taaataaat ttta                     3344
```

<210> SEQ ID NO 34
<211> LENGTH: 3389
<212> TYPE: DNA
<213> ORGANISM: Homo sapiens
<220> FEATURE:
<221> NAME/KEY: misc_feature
<223> OTHER INFORMATION: Incyte ID No: 7478405CB1

<400> SEQUENCE: 34

```
cggccgcgga aagaatgcgc gccgcccgtg cgctccgcct gccgcgtctg gccaccgca     60 gccgccgcgt ccgcacctga ccatggagtg cgccctcctg ctcgcgtgtg ccttcccggc    120
tgcgggttcg ggcccgccga ggggcctggc gggactgggg cgcgtggcca aggcgctcca    180
gctgtgctgc ctctgctgtg cgtcggtcgc gcggccttta gccagtgaca gcagcagcgg    240
cgccagcgga ttaaatgatg attacgtctt tgtcacgcca gtagaagtag actcagccgg    300
gtcatatatt tcacacgaca ttttgcacaa cggcaggaaa aagcgatcgg cgcagaatgc    360
cagaagctcc ctgcactacc gattttcagc atttggacag gaactgcact tagaacttaa    420
gccctcggcg attttgagca gtcactttat tgtccaggta cttggaaaag atggtgcttc    480
agagactcag aaacccgagg tgcagcaatg cttctatcag ggatttatca gaaatgacag    540
ctcctcctct gtcgctgtgt ctacgtgtgc tggcttgtca ggtttaataa ggacacgaaa    600
aaatgaattc ctcatctcgc cattacctca gcttctggcc caggaacaca actacagctc    660
ccctgcgggt caccatcctc acgtactgta caaaaggaca gcagaggaga agatccagcg    720
gtaccgtggc taccccggct ctggccggaa ttatcctggt tactccccaa gtcacattcc    780
ccatgcatct cagagtcgag agacagagta tcaccatcga aggttgcaaa agcagcattt    840
ttgtggacga cgcaagaaat atgctcccaa gcctcccaca gaggacacct atctaaggtt    900
tgatgaatat gggagctctg ggcgacccag aagatcagct ggaaaatcac aaaagggcct    960
caatgtggaa accctcgtgg tggcagacaa gaaaatggtg gaaaagcatg gcaagggaaa    1020
tgtcaccaca tacattctca cagtaatgaa catggtttct ggcctatttg aagatgggac    1080
tattggaagt gacataaacg tggttgtggt gagcctaatt cttctggaac aagaacctgg    1140
aggattattg atcaaccatc atgcagacca gtctctgaat agttttttgtc aatggcagtc    1200 tgccctcatt ggaaagaatg gcaagagaca tgatcatgcc atcttactaa caggattga    1260
```

```
tatttgttct tggaagaatg aaccatgtga cactctaggg tttgccccca tcagtggaat   1320
gtgctctaag taccgaagtt gtaccatcaa tgaggacaca ggacttggcc ttgccttcac   1380
catcgctcat gagtcagggc acaactttgg tatgattcac gacggagaag ggaatccctg   1440
cagaaaggct gaaggcaata tcatgtctcc cacactgacc ggaaacaatg gagtgttttc   1500
atggtcttcc tgcagccgcc agtatctcaa gaaattcctc agcacacctc aggcggggtg   1560
tctagtggat gagcccaagc aagcaggaca gtataaatat ccggacaaac taccaggaca   1620
gatttatgat gctgacacac agtgtaaatg caatttggaa gcaaaagcca agttatgcag   1680
ccttggtttt gtgaaggata tttgcaaatc actttggtgc caccgagtag ccacaggtg   1740 tgagaccaag tttatgcccg cagcagaagg accgtttgt ggcttgagta tgtggtgtcg   1800
gcaaggccag tgcgtaaagt ttggggagct cgggccccgg cccatccacg ccagtggtc   1860 cgcctggtcg aagtggtcag aatgttcccg gacatgtggt ggaggagtca agttccagga   1920
gagacactgc ataaccccca agcctcagta tggtggcata ttctgtccag gttctagccg   1980
tatttatcag ctgtgcaata ttaacccttg caatgaaaat agcttggatt ttcgggctca   2040
acagtgtgca gaatataaca gcaaaccttt ccgtggatgg ttctaccagt ggaaacccta   2100
tacaaaagtg gaagaggaag atcgatgcaa actgtactgc aaggctgaga ctttgaattt   2160
tttttttgca atgtccggca aagtgaaaga tggaactccc tgctccccaa acaaaaatga   2220
tgtttgtatt gacggggttt gtgaactagt gggatgtgat catgaactag ctctaaagc   2280 agtttcagat gcttgtggcg tttgcaaagg tgataattca acttgcaagt tttataaagg   2340
cctgtacctc aaccagcata aagcaaatga atattatccg gtggtcatca ttccagctgg   2400
cgcccgaagc atcgaaatcc aggagctgca ggtttcctcc agttacctcg cagttcgaag   2460
cctcagtcaa aagtattacc tcaccggggg ctggagcatc gactggcctg gggagttccc   2520
cttcgctggg accacgtttg aataccagcc ctctttcaac cgcccggaac gtctgtacgc   2580
gccagggccc acaaatgaga cgctggtctt tgaaattctg atgcaaggca aaaatccagg   2640
gatagcttgg aagtatgcac ttcccaaggt catgaatgga actccaccag ccacaaaaag   2700
acctgcctat acctggagta tcgtgcagtc agagtgctcc gtctcctgtg gtggaggtta   2760
cataaatgta aaggccattt gcttgcgaga tcaaaatact caagtcaatt cctcattctg   2820
cagtgcaaaa accaagccag taactgagcc caaaatctgc aacgctttct cctgcccggc   2880
ttactggatg ccaggtgaat ggagtacatg cagcaaggcc tgtgctggag ccagcagag   2940 ccgaaagatc cagtgtgtgc aaaagaagcc cttccaaaag gaggaagcag tgttgcattc   3000
tctctgtcca gtgagcacac ccactcaggt ccaagcctgc aacagccatg cctgccctcc   3060
acaatggagc cttggaccct ggtctcagtg ttccaagacc tgtggacgag gggtgaggaa   3120
gcgtgaactc ctctgcaagg gctctgccgc agaaaccctc cccgagagcc agtgtaccag   3180
tctccccaga cctgagctgc aggagggctg tgtgcttgga cgatgcccca agaacagccg   3240
gctacagtgg gtcgcttctt cgtggagcga ggtattgatt agaagtcact gctgggtcag   3300
gagattgaga ccatcctggc taacacagtg aaaccctgtc tctactaaaa atacaaaaaa   3360
ttagccaggc aaggtggcag gcgcctgta                                     3389
```

PROTEASES

TECHNICAL FIELD

This invention relates to nucleic acid and amino acid sequences of proteases and to the use of these sequences in the diagnosis, treatment, and prevention of gastrointestinal, cardiovascular, autoimmune/inflammatory, cell proliferative, developmental, epithelial, neurological, and reproductive disorders, and in the assessment of the effects of exogenous compounds on the expression of nucleic acid and amino acid sequences of proteases.

BACKGROUND OF THE INVENTION

Proteases cleave proteins and peptides at the peptide bond that forms the backbone of the protein or peptide chain. Proteolysis is one of the most important and frequent enzymatic reactions that occurs both within and outside of cells. Proteolysis is responsible for the activation and maturation of nascent polypeptides, the degradation of misfolded and damaged proteins, and the controlled turnover of peptides within the cell. Proteases participate in digestion, endocrine function, and tissue remodeling during embryonic development, wound healing, and normal growth. Proteases can play a role in regulatory processes by affecting the half life of regulatory proteins. Proteases are involved in the etiology or progression of disease states such as inflammation, angiogenesis, tumor dispersion and metastasis, cardiovascular disease, neurological disease, and bacterial, parasitic, and viral infections.

Proteases can be categorized on the basis of where they cleave their substrates. Exopeptidases, which include aminopeptidases, dipeptidyl peptidases, tripeptidases, carboxypeptidases, peptidyl-di-peptidases, dipeptidases, and omega peptidases, cleave residues at the termini of their substrates. Endopeptidases, including serine proteases, cysteine proteases, and metalloproteases, cleave at residues within the peptide. Four principal categories of mammalian proteases have been identified based on active site structure, mechanaism of action, and overall three-dimensional structure. (See Beynon, R. J. and J. S. Bond (1994) *Proteolytic Enzymes: A Practical Approach*, Oxford University Press, New York N.Y., pp. 1–5.)

Serin Proteases

The serine proteases (SPs) are a large, widespread family of proteolytic enzyes that include the digestive enzymes trysin and chymotrypsin, components of the complement and blood-clotting cascades, and enzymes that control the degradation and turnover of macromolecules within the cell and in the extracellular matrix Most of the more than 20 subfamilies can be grouped into six clans, each with a common ancestor. These six clans are hypothesized to have descended from at least four evolutionarily distinct ancestors. SPs are named for the presence of a serine residue found in the active catalytic site of most families. The active site is defined by the catalytic triad, a set of conserved asparagine, histidine, and serine residues critical for catalysis. These residues form a charge relay network that facilitates substrate binding. Other residues outside the active site form an oxyanion hole that stabilizes the tetrahedral transition intermediate formed during catalysis. SPs have a wide range of substrates and can be subdivided into subfamilies on the basis of their substrate specificity. The main subfamilies are named for the residue(s) after which they cleave: trypases (after arginine or lysine), aspases (after aspartate), chymases (after phenylalanine or leucine), metases (methionine), and serases (after serine) (Rawlings, N. D. and A. J. Barrett (1994) Methods Enzymol. 244:19–61).

Most mammalian serine proteases are synthesized as zymogens, inactive precursors that are activated by proteolysis. For example, trypsinogen is converted to its active form, trypsin, by enteropeptidase. Enteropeptidase is an intestinal protease that removes an N-terminal fragment from trypsinogen. The remaining active fragment is trypsin, which in turn activates the precursors of the other pancreatic enzymes. Likewise, proteolysis of prothrombin, the precursor of thrombin, generates three separate polypeptide fragments. The N-ternninal fragment is released while the other two fragments, which comprise active thrombin, remain associated throug disulfide bonds.

The two largest SP subfamilies are the chymotrypsin (S1) and subtilisin (S8) families. Some members of the chymotrypsin family contain two structural domains unique to this family. Kringle domains are triple-looped, disulfide cross-linked domains found in varying copy number. Kringles are thought to play a role in binding mediators such as membranes, other proteins or phospholipids, and in the regulation of proteolytic activity (PROSITE PDOC00020). Apple domains are 90 amino-acid repeated domains, each containing six conserved cysteines. Three disulfide bonds link the first and sixth, second and fifth, and third and fourth cysteines (PROSITE PDOC00376). Apple domains are involved in protein-protein interactions. S1 family members include trypsin, chymotrypsin, coagulation factors IX–XII, complement factors B, C, and D, granzymes, kallikrein, and tissue- and urokinase-plasminogen activators. The subtilisin family has members found in the eubacteria, archaebacteria, eukaryotes, and viruses. Subtilisins include the proprotein-processing endopeptidases kexin and furin and the pituitary prohormone convertases PC1, PC2, PC3, PC6, and PACE4 (Rawlings and Barrett, supra).

SPs have functions in many normal processes and some have been implicated in the etiology or treatment of disease. Enterokinase, the initiator of intestinal digestion, is found in the intestinal brush border, where it cleaves the acidic propeptide from trypsinogen to yield active trypsin (Kitamoto, Y. et al. (1994) Proc. Natl. Acad. Sci. USA 91:7588–7592). Prolylcarboxypeptidase, a lysosomal serine peptidase that cleaves peptides such as angiotensin II and III and [des-Arg9] bradykinin, shares sequence homology with members of both the serine carboxypeptidase and prolylendopeptidase families (Tan, F. et al. (1993) J. Biol. Chem. 268:16631–16638). The protease neuropsin may influence synapse formation and neuronal connectivity in the hippocampus in response to neural signaling (Chen, Z.-L. et al. (1995) J. Neurosci. 15:5088–5097). Tissue plasminogen activator is useful for acute management of stroke (Zivin, J. A. (1999) Neurology 53:14–19) and myocardial infarction Ross, A. M. (1999) Clin. Cardiol. 22:165–171). Some receptors (PAR, for proteinase-activated receptor), highly expressed throughout the digestive tract, are activated by proteolytic cleavage of an extracellular domain. The major agonists for PARs, thrombin, trypsin, and mast cell tryptase, are released in allergy and inflammatory conditions. Control of PAR activation by proteases has been suggested as a promising therapeutic target (Vergnolle, N. (2000) Aliment. Pharmacol. Ther. 14:257–266; Rice, K. D. et al. (1998) Curr. Pharm. Des. 4:381–396). Prostate-specific antigen (PSA) is a kallikrein-like serine protease synthesized and secreted exclusively by epithelial cells in the prostate gland. Serum PSA is elevated in prostate cancer and is the most sensitive physiological marker for monitoring cancer progression and response to therapy. PSA can also identify the prostate as the origin of a metastatic tumor (Brawer, M. K. and P. H. Lange (1989) Urology 33:11–16).

The signal peptidase is a specialized class of SP found in all prokaryotic and eukaryotic cell types that serves in the processing of signal peptides from certain proteins. Signal peptides are amino-terminal domains of a protein which direct the protein from its ribosomal assembly site to a particular cellular or extracellular location. Once the protein has been exported, removal of the signal sequence by a signal peptidase and posttranslational processing, e.g., glycosylation or phosphorylation, activate the protein. Signal peptidases exist as multi-subunit complexes in both yeast and mammals. The canine signal peptidase complex is composed of five subunits, all associated with the microsomal membrane and containing hydrophobic regions that span the membrane one or more times (Shelness, G. S. and G. Blobel (1990) J. Biol. Chem. 265:9512–9519). Some of these subunits serve to fix the complex in its proper position on the membrane while others contain the actual catalytic activity.

Another family of proteases which have a serine in their active site are dependent on the hydrolysis of ATP for their activity. These proteases contain proteolytic core domains and regulatory ATPase domains which can be identified by the presence of the P-loop, an ATP/GTP-binding motif (PROSITE POC00803). Members of this family include the eukaryotic mitochondrial matrix proteases, Clp protease and the proteasome. Clp protease was originally found in plant chloroplasts but is believed to be widespread in both prokaryotic and eukaryotic cells. The gene for early-onset torsion dystonia encodes a protein related to Clp protease (Ozelius, L. J. et al. (1998) Adv. Neurol. 78:93–105).

The proteasome is an intracellular protease complex found in some bacteria and in all eukaryotic cells, and plays an important role in cellular physiology. Proteasomes are associated with the ubiquitin conjugation system (UCS), a major pathway for the degradation of cellular proteins of all types, including proteins that function to activate or repress cellular processes such as transcription and cell cycle progression (Ciechanover, A. (1994) Cell 79:13–21). In the UCS pathway, proteins targeted for degradation are conjugated to ubiquitin, a small heat stable piotein. The ubiquitinated protein is then recognized and degraded by the proteasome. The resultant ubiquitin-peptide complex is hydrolyzed by a ubiquitin carboxyl terminal hydrolase, and free ubiquitin is released for reutilization by the UCS. Ubiquitin-proteasome systems are implicated in the degradation of mitotic cyclic kinases, oncoproteins, tumor suppressor genes (p53), cell surface receptors associated with signal transduction, transcriptional regulators, and mutated or damaged proteins (Ciechanover, supra). This pathway has been implicated in a number of diseases, including cystic fibrosis, Angelman's syndrome, and Liddle syndrome (reviewed in Schwartz, A. L. and A. Ciechanover (1999) Annu. Rev. Med. 50:57–74). A murine proto-oncogene, Unp, encodes a nuclear ubiquitin protease whose overexpression leads to oncogenic transformation of NIH3T3 cells. The human homologue of this gene is consistently elevated in small cell tumors and adenocarcinomas of the lung (Gray, D. A. (1995) Oncogene 10:2179–2183). Ubiquitin carboxyl terminal hydrolase is involved in the differentiation of a lymphoblastic leukemia cell line to a non-dividing mature state (Maki, A. et al. (1996) Differentiation 60:59–66). In neurons, ubiquitin carboxyl terminal hydrolase (PGP 9.5) expression is strong in the abnormal structures that occur inhuman neurodegenerative diseases (Lowe, J. et al. (1990) J. Pathol. 161:153–160). The proteasome is a large (~2000 kDa) multisubunit complex composed of a central catalytic core containing a variety of proteases arranged in four seven-membered rings with the active sites facing inwards into the central cavity, and terminal ATPase subunits covering the outer port of the cavity and regulating substrate entry (for review, see Schmidt, M. et al. (1999) Curr. Opin. Chem. Biol. 3:584–591).

Cysteine Proteases

Cysteine proteases (CPs) are involved in diverse cellular processes ranging from the processing of precursor proteins to intracellular degradation Nearly half of the CPs known are present only in viruses. CPs have a cysteine as the major catalytic residue at the active site where catalysis proceeds via a thioester intermediate and is facilitated by nearby histidine and asparagine residues. A glutamine residue is also important, as it helps to form an oxyanion hole. Two important CP families include the papain-like enzymes (C1) and the calpains (C2). Papain-like family members are generally lysosomal or secreted and therefore are synthesized with signal peptides as well as propeptides. Most members bear a conserved motif in the propeptide that may have structural significance (Karrer, K. M. et al. (1993) Proc. Natl. Acad. Sci. USA 90:3063–3067). Three-dimensional structures of papain family members show a bilobed molecule with the catalytic site located between the two lobes. Papains include cathepsins B, C, H, L, and S, certain plant allergens and dipeptidyl peptidase (for a review, see Rawlings, N. D. and A. J. Barrett (1994) Methods Enzymol. 244:461–486).

Some CPs are expressed ubiquitously, while others are produced only by cells of the immune system. Of particular note, CPs are produced by monocytes, macrophages and other cells which migrate to sites of inflammation and secrete molecules involved in tissue repair. Overabundance of these repair molecules plays a role in certain disorders. In autoimmune diseases such as rheumatoid arthritis, secretion of the cysteine peptidase cathepsin C degrades collagen, laminin, elastin and other structural proteins found in the extracellular matrix of bones. Bone weakened by such degradation is also more susceptible to tumor invasion and metastasis. Cathepsin L expression may also contribute to the influx of mononuclear cells which exacerbates the destruction of the rheumatoid synovium (Keyszer, G. M. (1995) Arthritis Rheum. 38:976–984).

Calpains are calcium-dependent cytosolic endopeptidases which contain both an N-terminal catalytic domain and a C-terminal calcium-binding domain. Calpain is expressed as a proenzyme heterodimer consisting of a catalytic subunit unique to each isoform and a regulatory subunit common to different isoforms. Each subunit bears a calcium-binding EF-hand domain. The regulatory subunit also contains a hydrophobic glycine-rich domain that allows the enzyme to associate with cell membranes. Calpains are activated by increased intracellular calcium concentration, which induces a change in conformation and limited autolysis. The resultant active molecule requires a lower calcium concentration for its activity (Chan, S. L. and M. P. Mattson (1999) J. Neurosci. Res. 58:167–190). Calpain expression is predominantly neuronal, although it is present in other tissues. Several chronic neurodegenerative disorders, including ALS, Parkinson's disease and Alzheimer's disease are associated with increased calpain expression (Chan and Mattson, supra). Calpain-mediated breakdown of the cytoskeleton has been proposed to contribute to brain damage resulting from head injury (McCracken, E. et al. (1999) J. Neurotrauma 16:749–761). Calpain-3 is predominantly expressed in skeletal muscle, and is responsible for limb-girdle muscular dystrophy type 2A (Minami, N. et al. (1999) J. Neurol. Sci. 171:31–37).

Another family of thiol proteases is the caspases, which are involved in the initiation and execution phases of apoptosis. A pro-apoptotic signal can activate initiator caspases that trigger a proteolytic caspase cascade, leading to the hydrolysis of target proteins and the classic apoptotic death of the cell. Two active site residues, a cysteine and a histidine, have been implicated in the catalytic mechanism. Caspases are among the most specific endopeptidases, cleaving after aspartate residues. Caspases are synthesized as inactive zymogens consisting of one large (p20) and one small (p10) subunit separated by a small spacer region, and a variable N-terminal prodomain. This prodomain interacts with cofactors that can positively or negatively affect apoptosis. An activating signal causes autoproteolytic cleavage of a specific aspartate residue (D297 in the caspase-1 numbering convention) and removal of the spacer and prodomain, leaving a p10/p20 heterodimer. Two of these heterodimers interact via their small subunits to form the catalytically active tetramer. The long prodomains of some caspase family members have been shown to promote dimerization and auto-processing of procaspases. Some caspases contain a "death effector domain" in their prodomain by which they can be recruited into self-activating complexes with other caspases and FADD protein associated death receptors or the TNF receptor complex. In addition, two dimers from different caspase family members can associate, changing the substrate specificity of the resultant tetramer. Endogenous caspase inhibitors (inhibitor of apoptosis proteins, or IAPs) also exist. All these interactions have clear effects on the control of apoptosis (reviewed in Chan and Mattson, supra; Salveson, G. S. and V. M. Dixit (1999) Proc. Natl. Acad. Sci. USA 96:10964–10967).

Caspases have been implicated in a number of diseases. Mice lacking some caspases have severe nervous system defects due to failed apoptosis in the neuroepithelium and suffer early lethality. Others show severe defects in the inflammatory response, as caspases are responsible for processing IL-1b and possibly other inflammatory cytoldnes (Chan and Mattson, supra). Cowpox virus and baculoviruses target caspases to avoid the death of their host cell and promote successful infection. In addition, increases in inappropriate apoptosis have been reported in AIDS, neurodegenerative diseases and ischemic injury, while a decrease in cell death is associated with cancer (Salveson and Dixit, supra; Thompson, C. B. (1995) Science 267:1456–1462).

Aspartyl Proteases

Aspartyl proteases (APs) include the lysosomal proteases cathepsins D and E, as well as chymosin, renin, and the gastric pepsins. Most retroviruses encode an AP, usually as part of the pol polyprotein. APs, also called acid proteases, are monomeric enzymes consisting of two domains, each domain containing one half of the active site with its own catalytic aspartic acid residue. APs are most active in the range of pH 2–3, at which one of the aspartate residues is ionized and the other neutral. The pepsin family of APs contains many secreted enzymes, and all are likely to be synthesized with signal peptides and propeptides. Most family members have three disulfide loops, the first ~5 residue loop following the first aspartate, the second 5–6 residue loop preceding the second aspartate, and the third and largest loop occuring toward the C terminus. Retropepsins, on the other hand, are analogous to a single domain of pepsin, and become active as homodimers with each retropepsin monomer contributing one half of the active site. Retropepsins are required for processing the viral polyproteins.

APs have roles in various tissues, and some have been associated with disease. Renin mediates the first step in processing the hormone angiotensin, which is responsible for regulating electrolyte balance and blood pressure (reviewed in Crews, D. E. and S. R. Williams (1999) Hum. Biol. 71:475–503). Abnormal regulation and expression of cathepsins are evident in various inflanmatory disease states. Expression of cathepsin D is elevated in synovial tissues from patients with rheumatoid arthritis and osteoarthritis. The increased expression and differential regulation of the cathepsins are linked to the metastatic potential of a variety of cancers (Chambers, A. F. et al. (1993) Crit. Rev. Oncol. 4:95–114).

Metalloproteases

Metalloproteases require a metal ion for activity, usually manganese or zinc. Examples of manganese metalloenzymes include aminopeptidase P and human proline dipeptidase (PEPD). Aminopeptidase P can degrade bradykinin, a nonapeptide activated in a variety of inflammatory responses. Aminopeptidase P has been implicated in coronary ischemia/reperfasion injury. Administration of aminopeptidase P inhibitors has been shown to have a cardioprotective effect in rats (Ersahin, C. et al. (1999) J. Cardiovasc. Pharmacol 34:604–611).

Most zinc-dependent metalloproteases share a common sequence in the zinc-binding domain. The active site is made up of two histidines which act as zinc ligands and a catalytic glutamic acid C-terminal to the first histidine. Proteins containing this signature sequence are known as the metzincins and include aminopeptidase N, angiotensin-converting enzyme, neurolysin, the matrix metalloproteases and the adamalysins (ADAMS). An alternate sequence is found in the zinc carboxypeptidases, in which all three conserved residues—two histidines and a glutamic acid—are involved in zinc binding.

A number of the neutral metalloendopeptidases, including angiotensin converting enzyme and the aminopeptidases, are involved in the metabolism of peptide hormones. High atninopeptidase B activity, for example, is found in the adrenal glands and neurohypophyses of hypertensive rats (Prieto, I. et al. (1998) Horm. Metab. Res. 30:246–248). Oligopeptidase M/neurolysin can hydrolyze bradykin as well as neurotensin (Serizawa, A. et al. (1995) J. Biol. Chem. 270:2092–2098). Neurotensin is a varoactive peptide that can act as a neurotransmitter in the brain, where it has been implicated in limiting food intake (Tritos, N. A. et al. (1999) Neuropeptides 33:339–349).

The matrix metalloproteases (MMPs) are a family of at least 23 enzymes that can degrade components of the extracellular matrix (ECM). They are $Zn^{+2}$ endopeptidases with an N-terminal catalytic domain. Nearly all members of the family have a hinge peptide and C-terminal domain which can bind to substrate molecules in the ECM or to inhibitors produced by the tissue (TIMPs, for tissue inhibitor of metalloprotease; Campbell, I. L. et al. (1999) Trends Neurosci. 22.285). The presence of fibronectin-like repeats, transmembrane domains, or C-terminal hemopexinase-like domains can be used to separate MMPs into collagenase, gelatinase, stromelysin and membrane-type MMP subfamilies. In the inactive form, the $Zn^{+2}$ ion in the active site interacts with a cysteine in the pro-sequence. Activating factors disrupt the $Zn^{+2}$-cysteine interaction, or "cysteine switch," exposing the active site. This partially activates the enzyme, which then cleaves off its propeptide and becomes fully active. MMPs are often activated by the serine proteases plasmin and furin. MMPs are often regulated by stoichiometric, noncovalent interactions with inhibitors; the balance of protease to inhibitor, then, is very important in tissue homeostasis (reviewed in Yong, V. W. et al. (1998) Trends Neurosci. 21:75).

MMPs are implicated in a number of diseases including osteoarthritis (Mitchell, P. et al. (1996) J. Clin. Invest. 97:761), atherosclerotic plaque rupture (Sukhova, G. K. et al. (1999) Circulation 99:2503), aortic aneurysm (Schneiderman, J. et al. (1998) Am. J. Path. 152:703), non-healing wounds (Saarialho-Kere, U. K. et al. (1994) J. Clin. Invest. 94:79), bone resorption (Blavier, L. and J. M. Delaisse (1995) J. Cell Sci. 108:3649), age-related macular degeneration (Steen, B. et al. (1998) Invest. Ophthalmol. Vis. Sci. 39:2194), emphysema Finlay, G. A. et al. (1997) Thorax 52:502), myocardial infarction (Rohde, L. E. et al. (1999) Circulation 99:3063) and dilated cardiomyopathy (Thomas, C. V. et al. (1998) Circulation 97:1708). MMP inibitors prevent metastasis of mammary carcinoma and experimental tumors in rat, and Lewis lung carcinoma, hemangioma, and human ovarian carcinoma xenografts in mice (Eccles, S. A. et al. (1996) Cancer Res. 56:2815; Anderson et al. (1996) Cancer Res. 56:715–718; Volpert, O. V. et al. (1996) J. Clin. Invest. 98:671; Taraboletti, G. et al. (1995) J. NCI 87:293; Davies, B. et al. (1993) Cancer Res. 53:2087). MMPs may be active in Alzheimer's disease. A number of MMPs are implicated in multiple sclerosis, and administration of MMP inhbitors can relieve some of its symptoms (reviewed in Yong, supra).

Another family of metalloproteases is the ADAMs, for A Disintegrin and Metalloprotease Domain, which they share with their close relatives the adamalysins, snake venom metalloproteases (SVMPs). ADAMs combine features of both cell surface adhesion molecules and proteases, containing a prodomain, a protease domain, a disintegrin domain, a cysteine rich domain, an epidermal growth factor repeat, a transmembrane domain, and a cytoplasmic tail. The first three domains listed above are also found in the SVPs. The ADAMs possess four potential functions: proteolysis, adhesion, signaling and fusion. The ADAMs share the metzincin zinc binding sequence and are inhibited by some MMP antagonists such as TIMP-1.

ADAMs are implicated in such processes as sperm-egg binding and fusion, myoblast fusion, and protein-ectodomain processing or shedding of cytokines, cytokine receptors, adhesion proteins and other extracellular protein domains (Schlöndorff, J. and C. P. Blobel (1999) J. Cell. Sci. 112:3603–3617). The Kuzbanian protein cleaves a substrate in the NOTCH pathway (possibly NOTCH itself), activating the program for lateral inhibition in *Drosophila* neural development. Two ADAMs, TACE (ADAM 17) and ADAM 10, are proposed to have analogous roles in the processing of amyloid precursor protein in the brain (Schlöndorff and Blobel, supra). TACE has also been identified as the TNF activating enzyme (Black, R. A. et al. (1997) Nature 385:729). TNF is a pleiotropic cytokine that is important in mobilizing host defenses in response to infection or trauma, but can cause severe damage in excess and is often over-produced in autoimmune disease. TACE cleaves membrane-bound pro-TNF to release a soluble form. Other ADAMs may be involved in a similar type of processing of other membrane-bound molecules.

The ADAMTS sub-family has all of the features of ADAM family metalloproteases and contain an additional thrombospondin domain (TS). The prototypic ADAMTS was identified in mouse, found to be expressed in heart and kidney and upregulated by proinflammatory stimuli (Kuno, K et al. (1997) J. Biol. Chem. 272:556–562). To date eleven members are recognized by the Human Genome Organization (HUGO; http://www.gene.ucl.ac.uk/users/hester/adamts.html#Approved). Members of this family have the ability to degrade aggrecan, a high molecular weight proteoglycan which provides cartilage with important mechanical properties including compressibility, and which is lost during the development of arthritis. Enzymes which degrade aggrecan are thus considered attractive targets to prevent and slow the degradation of articular cartilage (See, e.g., Tortorella, M. D. (1999) Science 284:1664; Abbaszade, I. (1999) J. Biol. Chem. 274:23443). Other members are reported to have antiangiogenic potential (Kuno et al., supra) and/or procollagen processing (Colige, A. et al. (1997) Proc. Natl. Acad. Sci. USA 94:2374).

The discovery of new proteases, and the polynucleotides encoding them, satisfies a need in the art by providing new compositions which are useful in the diagnosis, prevention, and treatment of gastrointestinal, cardiovascular, autoimmune/inflammatory, cell proliferative, developmental, epithelial, neurological, and reproductive disorders, and in the assessment of the effects of exogenous compounds on the expression of nucleic acid and amino acid sequences of proteases.

SUMMARY OF THE INVENTION

The invention features purified polypeptides, proteases, referred to collectively as "PRTS" and individually as "PRTS-1," "PRTS-2,""PRTS-3," "PRTS-4," "PRTS-5," "PRTS-6," "PRTS-7,""PRTS-8," "PRTS-9," "PRTS-10," "PRTS-11," "PRTS-12," "PRTS-13," "PRTS-14," "PRTS-15," "PRTS-16," and "PRTS-17." In one aspect, the invention provides an isolated polypeptide selected from the group consisting of a) a polypeptide comprising an amino acid sequence selected from the group consisting of SEQ ID NO:1–17, b) a polypeptide comprising a naturally occurring amino acid sequence at least 90% identical to an amino acid sequence selected from the group consisting of SEQ ID NO:1–17, c) a biologically active fragment of a polypeptide having an amino acid sequence selected from the group consisting of SEQ ID NO:1–17, and d) an immunogenic fragment of a polypeptide having an amino acid sequence selected from the group consisting of SEQ ID NO:1–17. In one alternative, the invention provides an isolated polypeptide comprising the amino acid sequence of SEQ ID NO:1–17.

The invention further provides an isolated polynucleotide encoding a polypeptide selected from the group consisting of a) a polypeptide comprising an amino acid sequence selected from the group consisting of SEQ ID NO:1–17, b) a polypeptide comprising a naturally occurring amino acid sequence at least 90% identical to an amino acid sequence selected from the group consisting of SEQ ID NO:1–17, c) a biologically active fragment of a polypeptide having an amino acid sequence selected from the group consisting of SEQ ID NO:1–17, and d) an immunogenic fragment of a polypeptide having an amino acid sequence selected from the group consisting of SEQ ID NO:1–17. In one alternative, the polynucleotide encodes a polypeptide selected from the group consisting of SEQ ID NO:1–17. In another alternative, the polynucleotide is selected from the group consisting of SEQ ID NO:18–34.

Additionally, the invention provides a recombinant polynucleotide comprising a promoter sequence operably linked to a polynucleotide encoding a polypeptide selected from the group consisting of a) a polypeptide comprising an amino acid sequence selected from the group consisting of SEQ ID NO:1–17, b) a polypeptide comprising a naturally occurring amino acid sequence at least 90% identical to an amino acid sequence selected from the group consisting of SEQ ID NO:1–17, c) a biologically active fragment of a polypeptide having an amino acid sequence selected from the group consisting of SEQ ID NO:1–17, and d) an immunogenic fragment of a polypeptide having an amino acid sequence selected from the group consisting of SEQ ID NO:1–17. In one alternative, the invention provides a cell transformed with the recombinant polynucleotide. In another alternative, the invention provides a transgenic organism comprising the recombinant polynucleotide.

The invention also provides a method for producing a polypeptide selected from the group consisting of a) a polypeptide comprising an amino acid sequence selected from the group consisting of SEQ ID NO:1–17, b) a polypeptide comprising a naturally occurring amino acid sequence at least 90% identical to an amino acid sequence selected from the group consisting of SEQ ID NO:1–17, c) a biologically active fragment of a polypeptide having an amino acid sequence selected from the group consisting of SEQ ID NO:1–17, and d) an immunogenic fragment of a polypeptide having an amino acid sequence selected from the group consisting of SEQ ID NO:1–17. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Additionally, the invention provides an isolated antibody which specifically binds to a polypeptide selected from the group consisting of a) a polypeptide comprising an amino acid sequence selected from the group consisting of SEQ ID NO:1–17, b) a polypeptide comprising a naturally occurring amino acid sequence at least 90% identical to an amino acid sequence selected from the group consisting of SEQ ID NO:1–17, c) a biologically active fragment of a polypeptide having an amino acid sequence selected from the group consisting of SEQ ID NO:1–17, and d) an immunogenic fragment of a polypeptide having an amino acid sequence selected from the group consisting of SEQ ID NO:1–17.

The invention further provides an isolated polynucleotide selected from the group consisting of a) a polynucleotide comprising a polynucleotide sequence selected from the group consisting of SEQ ID NO:18–34, b) a polynucleotide comprising a naturally occurring polynucleotide sequence at least 90% identical to a polynucleotide sequence selected from the group consisting of SEQ ID NO:18–34, c) a polynucleotide complementary to the polynucleotide of a), d) a polynucleotide complementary to the polynucleotide of b), and e) an RNA equivalent of a)–d). In one alternative, the polynucleotide comprises at least 60 contiguous nucleotides.

Additionally, the invention provides a method for detecting a target polynucleotide in a sample, said target polynucleotide having a sequence of a polynucleotide selected from the group consisting of a) a polynucleotide comprising a polynucleotide sequence selected from the group consisting of SEQ ID NO:18–34, b) a polynucleotide comprising a naturally occurring polynucleotide sequence at least 90% identical to a polynucleotide sequence selected from the group consisting of SEQ ID NO:18–34, c) a polynucleotide complementary to the polynucleotide of a), d) a polynucleotide complementary to the polynucleotide of b), and e) an RNA equivalent of a)–d). The method comprises a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. In one alternative, the probe comprises at least 60 contiguous nucleotides.

The invention further provides a method for detecting a target polynucleotide in a sample, said target polynucleotide having a sequence of a polynucleotide selected from the group consisting of a) a polynucleotide comprising a polynucleotide sequence selected from the group consisting of SEQ ID NO:18–34, b) a polynucleotide comprising a naturally occurring polynucleotide sequence at least 90% identical to a polynucleotide sequence selected from the group consisting of SEQ ID NO:18–34, c) a polynucleotide complementary to the polynucleotide of a), d) a polynucleotide complementary to the polynucleotide of b), and e) an RNA equivalent of a)–d). The method comprises a) amplifying said target polynucleotide or fragment thereof using polymerase chain reaction amplification, and b) detecting the presence or absence of said amplified target polynucleotide or fragment thereof, and, optionally, if present, the amount thereof.

The invention further provides a composition comprising an effective amount of a polypeptide selected from the group consisting of a) a polypeptide comprising an amino acid sequence selected from the group consisting of SEQ ID NO:1–17, b) a polypeptide comprising a naturally occurring amino acid sequence at least 90% identical to an amino acid sequence selected from the group consisting of SEQ ID NO:1–17, c) a biologically active fragment of a polypeptide having an amino acid sequence selected from the group consisting of SEQ ID NO:1–17, and d) an immunogenic fragment of a polypeptide having an amino acid sequence selected from the group consisting of SEQ ID NO:1–17, and a pharmaceutically acceptable excipient. In one embodiment, the composition comprises an amino acid sequence selected from the group consisting of SEQ ID NO:1–17. The invention additionally provides a method of treating a disease or condition associated with decreased expression of functional PRTS, comprising administering to a patient in need of such treatment the composition.

The invention also provides a method for screening a compound for effectiveness as an agonist of a polypeptide selected from the group consisting of a) a polypeptide comprising an amino acid sequence selected from the group consisting of SEQ ID NO:1–17, b) a polypeptide comprising a naturally occurring amino acid sequence at least 90% identical to an amino acid sequence selected from the group consisting of SEQ ID NO:1–17, c) a biologically active fragment of a polypeptide having an amino acid sequence selected from the group consisting of SEQ ID NO:1–17, and d) an immunogenic fragment of a polypeptide having an amino acid sequence selected from the group consisting of SEQ ID NO:1–17. The method comprises a) exposing a sample comprising the polypeptide to a compound, and b) detecting agonist activity in the sample. In one alternative, the invention provides a composition comprising an agonist compound identified by the method and a pharmaceutically acceptable excipient. In another alternative, the invention provides a method of treating a disease or condition associated with decreased expression of functional PRTS, comprising administering to a patient in need of such treatment the composition.

Additionally, the invention provides a method for screening a compound for effectiveness as an antagonist of a polypeptide selected from the group consisting of a) a polypeptide comprising an amino acid sequence selected from the group consisting of SEQ ID NO:1–17, b) a polypeptide comprising a naturally occurring amino acid sequence at least 90% identical to an amino acid sequence selected from the group consisting of SEQ ID NO:1–17, c) a biologically active fragment of a polypeptide having an amino acid sequence selected from the group consisting of SEQ ID NO:1–17, and d) an immunogenic fragment of a polypeptide having an amino acid sequence selected from the group consisting of SEQ ID NO:1–17. The method comprises a) exposing a sample comprising the polypeptide to a compound, and b) detecting antagonist activity in the sample. In one alternative, the invention provides a composition comprising an antagonist compound identified by the method and a pharmaceutically acceptable excipient. In another alternative, the invention provides a method of treating a disease or condition associated with overexpression of functional PRTS, comprising administering to a patient in need of such treatment the composition.

The invention further provides a method of screening for a compound that specifically binds to a polypeptide selected from the group consisting of a) a polypeptide comprising an amino acid sequence selected from the group consisting of SEQ ID NO:1–17, b) a polypeptide comprising a naturally occurring amino acid sequence at least 90% identical to an amino acid sequence selected from the group consisting of SEQ ID NO:1–17, c) a biologically active fragment of a polypeptide having an amino acid sequence selected from the group consisting of SEQ ID NO:1–17, and d) an immunogenic fragment of a polypeptide having an amino acid sequence selected from the group consisting of SEQ ID NO:1–17. The method comprises a) combining the polypeptide with at least one test compound under suitable conditions, and b) detecting binding of the polypeptide to the test compound, thereby identifying a compound that specifically binds to the polypeptide.

The invention further provides a method of screening for a compound that modulates the activity of a polypeptide selected from the group consisting of a) a polypeptide comprising an amino acid sequence selected from the group consisting of SEQ ID NO:1–17, b) a polypeptide comprising a naturally occurring amino acid sequence at least 90% identical to an amino acid sequence selected from the group consisting of SEQ ID NO:1–17, c) a biologically active fragment of a polypeptide having an amino acid sequence selected from the group consisting of SEQ ID NO:1–17, and d) an immunogenic fragment of a polypeptide having an amino acid sequence selected from the group consisting of SEQ ID NO:1–17. The method comprises a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

The invention further provides a method for screening a compound for effectiveness in altering expression of a target polynucleotide, wherein said target polynucleotide comprises a polynucleotide sequence selected from the group consisting of SEQ ID NO:18–34, the method comprising a) exposing a sample comprising the target polynucleotide to a compound, and b) detecting altered expression of the target polynucleotide.

The invention further provides a method for assessing toxicity of a test compound, said method comprising a) treating a biological sample containing nucleic acids with the test compound; b) hybridizing the nucleic acids of the treated biological sample with a probe comprising at least 20 contiguous nucleotides of a polynucleotide selected from the group consisting of i) a polynucleotide comprising a polynucleotide sequence selected from the group consisting of SEQ ID NO:18–34, ii) a polynucleotide comprising a naturally occurring polynucleotide sequence at least 90% identical to a polynucleotide sequence selected from the group consisting of SEQ ID NO:18–34, iii) a polynucleotide having a sequence complementary to i), iv) a polynucleotide complementary to the polynucleotide of ii), and v) an RNA equivalent of i)–iv). Hybridization occurs under conditions whereby a specific hybridization complex is formed between said probe and a target polynucleotide in the biological sample, said target polynucleotide selected from the group consisting of i) a polynucleotide comprising, a polynucleotide sequence selected from the group consisting of SEQ ID NO:18–34, ii) a polynucleotide comprising a naturally occurring polynucleotide sequence at least 90% identical to a polynucleotide sequence selected from the group consisting of SEQ ID NO:18–34, iii) a polynucleotide complementary to the polynucleotide of i), iv) a polynucleotide complementary to the polynucleotide of ii), and v) an RNA equivalent of i)–iv). Alternatively, the target polynucleotide comprises a fragment of a polynucleotide sequence selected from the group consisting of i)–v) above; c) quantifying the amount of hybridization complex; and d) comparing the amount of hybridization complex in the treated biological sample with the amount of hybridization complex in an untreated biological sample, wherein a difference in the amount of hybridization complex in the treated biological sample is indicative of toxicity of the test compound.

BRIEF DESCRIPTION OF THE TABLES

Table 1 summarizes the nomenclature for the full length polynucleotide and polypeptide sequences of the present invention.

Table 2 shows the GenBank identification number and annotation of the nearest GenBank homolog for polypeptides of the invention. The probability score for the match between each polypeptide and its GenBank homolog is also shown.

Table 3 shows structural features of polypeptide sequences of the invention, including predicted motifs and domains, along with the methods, algorithms, and searchable databases used for analysis of the polypeptides.

Table 4 lists the cDNA and/or genomic DNA fragments which were used to assemble polynucleotide sequences of the invention, along with selected fragments of the polynucleotide sequences.

Table 5 shows the representative cDNA library for polynucleotides of the invention.

Table 6 provides an appendix which describes the tissues and vectors used for construction of the cDNA libraries shown in Table 5.

Table 7 shows the tools, programs, and algorithms used to analyze the polynucleotides and polypeptides of the invention, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"PRTS" refers to the amino acid sequences of substantially purified PRTS obtained from any species, particularly a mammalian species, including bovine, ovine, porcine, murine, equine, and human and from any source, whether natural, synthetic, semi-synthetic, or recombinant The term "agonist" refers to a molecule which intensifies or mimics the biological activity of PRTS. Agonists may include proteins, nucleic acids, carbohydrates, small molecules, or any other compound or composition which modulates the activity of PRTS either by directly interacting with PRTS or by acting on components of the biological pathway in which PRTS participates.

An "allelic variant" is an alternative form of the gene encoding PRTS. Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding PRTS include those sequences with deletions, insertions, or substitutions of different nucleotides, resulting in a polypeptide the same as PRTS or a polypeptide with at least one functional characteristic of PRTS. Included within this definition are polymorphisms which may or may not be readily detectable using a particular oligonucleotide probe of the polynucleotide encoding PRTS, and improper or unexpected hybridization to allelic variants, with a locus other than the normal chromosomal locus for the polynucleotide sequence encoding PRTS. The encoded protein may also be "altered," and may contain deletions, insertions, or substitutions of amino acid residues which produce a silent change and result in a functionally equivalent PRTS. Deliberate amino acid substitutions may be made on the basis of similarity in polarity, charge, solubility, hydrophobicity, hydrophilicity, and/or the amphipathic nature of the residues, as long as the biological or immunological activity of PRTS is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which inhibits or attenuates the biological activity of PRTS. Antagonists may include proteins such as antibodies, nucleic acids, carbohydrates, small molecules, or any other compound or composition which modulates the activity of PRTS either by directly interacting with PRTS or by acting on components of the biological pathway in which PRTS participates.

The term "antibody" refers to intact immunoglobulin molecules as well as to fragments thereof, such as Fab, $F(ab')_2$, and Fv fragments, which are capable of binding an epitopic determinant. Antibodies that bind PRTS polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three dimensional structures on the protein). An antigenic determinant may compete with the intact antigen (i.e., the immunogen used to elicit the immune response) for binding to an antibody.

The term "antisense" refers to any composition capable of base-pairing with the "sense" (coding) strand of a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine. Antisense molecules may be produced by any method including chemical synthesis or transcription. Once introduced into a cell, the complementary antisense molecule base-pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" or "immunogenic" refers to the capability of the natural, recombinant, or synthetic PRTS, or of any oligopeptide thereof, to induce a specific immune response in appropriate animals or cells and to bind with specific antibodies.

"Complementary" describes the relationship between two single-stranded nucleic acid sequences that anneal by base-pairing. For example, 5'-AGT-3' pairs with its complement, 3'-TCA-5'.

A "composition comprising a given polynucleotide sequence" and a "composition comprising a given amino acid sequence" refer broadly to any composition containing the given polynucleotide or amino acid sequence. The composition may comprise a dry formulation or an aqueous solution. Compositions comprising polynucleotide sequences encoding PRTS or fragments of PRTS may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been subjected to repeated DNA sequence analysis to resolve uncalled bases, extended using the XL-PCR kit (Applied Biosystems, Foster City, Calif.) in the 5' and/or the 3' direction, and resequenced, or which has been assembled from one or more overlapping cDNA, EST, or genomic DNA fragments using a computer program for fragment assembly, such as the GELVIEW fragment assembly system (GCG, Madison Wis.) or Phrap (University of Washington, Seattle Wash.). Some sequences have been both extended and assembled to produce the consensus sequence.

"Conservative amino acid substitutions" are those substitutions that are predicted to least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |

-continued

| Original Residue | Conservative Substitution |
|---|---|
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides.

The term "derivative" refers to a chemically modified polynucleotide or polypeptide. Chemical modifications of a polynucleotide can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "detectable label" refers to a reporter molecule or enzyme that is capable of generating a measurable signal and is covalently or noncovalently joined to a polynucleotide or polypeptide.

"Differential expression" refers to increased or upregulated; or decreased, downregulated, or absent gene or protein expression, determined by comparing at least two different samples. Such comparisons may be carried out between, for example, a treated and an untreated sample, or a diseased and a normal sample.

"Exon shuffling" refers to the recombination of different coding regions (exons). Since an exon may represent a structural or functional domain of the encoded protein, new proteins may be assembled through the novel reassortment of stable substructures, thus allowing acceleration of the evolution of new protein functions.

A "fragment" is a unique portion of PRTS or the polynucleotide encoding PRTS which is identical in sequence to but shorter in length than the parent sequence. A fragment may comprise up to the entire length of the defined sequence, minus one nucleotide/amino acid residue. For example, a fragment may comprise from 5 to 1000 contiguous nucleotides or amino acid residues. A fragment used as a probe, primer, antigen, therapeutic molecule, or for other purposes, maybe at least 5, 10, 15, 16, 20, 25, 30, 40, 50, 60, 75, 100, 150, 250 or at least 500 contiguous nucleotides or amino acid residues in length Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

A fragment of SEQ ID NO:18–34 comprises a region of unique polynucleotide sequence that specifically identifies SEQ ID NO:18–34, for example, as distinct from any other sequence in the genome from which the fragment was obtained. A fragment of SEQ ID NO:18–34 is useful, for example, in hybridization and amplification technologies and in analogous methods that distinguish SEQ ID NO:18–34 from related polynucleotide sequences. The precise length of a fragment of SEQ ID NO:18–34 and the region of SEQ ID NO:18–34 to which the fragment corresponds are routinely determinable by one of ordinary skill in the art based on the intended purpose for the fragment A fragment of SEQ ID NO:1–17 is encoded by a fragment of SEQ ID NO:18–34. A fragment of SEQ ID NO:1–17 comprises a region of unique amino acid sequence that specifically identifies SEQ ID NO:1–17. For example, a fragment of SEQ ID NO:1–17 is useful as an immunogenic peptide for the development of antibodies that specifically recognize SEQ ID NO:1–17. The precise length of a fragment of SEQ ID NO:1–17 and the region of SEQ ID NO:1–17 to which the fragment corresponds are routinely determinable by one of ordinary skill in the art based on the intended purpose for the fragment.

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using the default parameters of the CLUSTAL V algorithm as incorporated into the NEGAUGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151–153 and in Higgins, D. G. et al. (1992) CABIOS 8:189–191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequences.

Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403–410), which is available from several sources, including the NCBI, Bethesda, Md., and on the Internet at http://www.ncbi.nlm.nih.gov/BLAST/. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at http:/www.ncbi.nlm.nih.gov/gorf/bl2.html. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr. 21, 2000) set at default parameters. Such default parameters may be, for example:

Matrix: BLOSUM62
Reward for match: 1
Penalty for mismatch: −2
Open Gap: 5 and Extension Gap: 2 penalties
Gap x drop-off: 50
Expect: 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table. As with polynucleotide alignments, the percent identity is reported by CLUSTAL V as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example:

Matrix: BLOSUM62
Open Gap: 11 and Extension Gap: 1 penalties
Gap x drop-off: 50
Expect: 10
Word Size: 3
Filter: on Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Human artificial chromosomes" (HACs) are linear microchromosomes which may contain DNA sequences of about 6 kb to 10 Mb in size and which contain all of the elements required for chromosome replication, segregation and maintenance.

The term "humanized antibody" refers to an antibody molecule in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of complementarity. Specific hybridization complexes form under permissive annealing conditions and remain hybridized after the "washing" step (s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml sheared, denatured salmon sperm DNA.

Generally, stringency of hybridization is expressed, in part, with reference to the temperature under which the wash step is carried out. Such wash temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook, J. et al. (1989) *Molecular Cloning: A Laboratory Manual*, $2^{nd}$ ed., vol. 1–3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, sheared and denatured salmon sperm DNA at about 100–200 µg/ml. Organic solvent, such as formamide at a concentration of about 35–50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed in solution (e.g., $C_0 t$ or $R_0 t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of PRTS which is capable of eliciting an immune response when introduced into a living organism, for example, a mammal. The term "immunogenic fragment" also includes any polypeptide or oligopeptide fragment of PRTS which is useful in any of the antibody production methods disclosed herein or known in the art.

The term "microarray" refers to an arrangement of a plurality of polynucleotides, polypeptides, or other chemical compounds on a substrate.

The terms "element" and "array element" refer to a polynucleotide, polypeptide, or other chemical compound having a unique and defined position on a microarray.

The term "modulate" refers to a change in the activity of PRTS. For example, modulation may cause an increase or a decrease in protein activity, binding characteristics, or any other biological, functional, or immunological properties of PRTS.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

"Post-translational modification" of an PRTS may involve lipidation, glycosylation, phosphorylation, acetylation, racemization, proteolytic cleavage, and other modifications known in the art. These processes may occur synthetically or biochemically. Biochemical modifications will vary by cell type depending on the enzymatic milieu of PRTS.

"Probe" refers to nucleic acid sequences encoding PRTS, their complements, or fragments thereof, which are used to detect identical, allelic or related nucleic acid sequences. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Methods for preparing and using probes and primers are described in the references, for example Sambrook, J. et al. (1989) *Molecular Cloning: A Laboratory Manual*, $2^{nd}$ ed, vol. 1–3, Cold Spring Harbor Press, Plainview N.Y.; Ausubel F. M. et al. (1987) *Current Protocols in Molecular Biology*, Greene Publ. Assoc. & Wiley-Intersciences, New York N.Y.; Innis, M. et al. (1990) *PCR Protocols, A Guide to Methods and Applications*, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polymncleotides of up to 5,000 nucleotides from an input polynucleotide sequence of up to 32 kilobases. Similar primer selection programs have incorporated additional features for expanded capabilities. For example, the PrimOU primer selection program (available to the public from the Genoine Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignnents, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a sequence that is not naturally occuring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, supra. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector, e.g., based on a vaccinia virus, that could be use to vaccinate a mammal wherein the recombinant nucleic acid is expressed, inducing a protective immunological response in the mammal.

A "regulatory element" refers to a nucleic acid sequence usually derived from untranslated regions of a gene and includes enhancers, promoters, introns, and 5' and 3' untranslated regions (UTRs). Regulatory elements interact with host or viral proteins which control transcription, translation, or RNA stability.

"Reporter molecules" are chemical or biochemical moieties used for labeling a nucleic acid, amino acid, or antibody. Reporter molecules include radionuclides; enzymes; fluorescent, chemiluminescent, or chromogenic agents; substrates; cofactors; inhibitors; magnetic particles; and other moieties known in the art.

An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose.

The term "sample" is used in its broadest sense. A sample suspected of containing PRTS, nucleic acids encoding PRTS, or fragments thereof may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least 60% free, preferably at least 75% free, and most preferably at least 90% free from other components with which they are naturally associated.

A "substitution" refers to the replacement of one or more amino acid residues or nucleotides by different amino acid residues or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

A "transcript image" refers to the collective pattern of gene expression by a particular cell type or tissue under given conditions at a given time.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989), supra.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides will generally have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides.

The Invention

The invention is based on the discovery of new human proteases (PRTS), the polynucleotides encoding PRTS, and the use of these compositions for the diagnosis, treatment, or prevention of gastrointestinal, cardiovascular, autoimmune/inflammatory, cell proliferative, developmental, epithelial, neurological, and reproductive disorders.

Table 1 summarizes the nomenclature for the full length polynucleotide and polypeptide sequences of the invention. Each polynucleotide and its corresponding polypeptide are correlated to a single Incyte project identification number (Incyte Project ID). Each polypeptide sequence is denoted by both a polypeptide sequence identification number (Polypeptide SEQ ID NO:) and an Incyte polypeptide sequence number (Incyte Polypeptide ID) as shown. Each polynucleotide sequence is denoted by both a polynucleotide sequence identification number (Polynucleotide SEQ ID NO:) and an Incyte polynucleotide consensus sequence number (Incyte Polynucleotide ID) as shown.

Table 2 shows sequences with homology to the polypeptides of the invention as identified by BLAST analysis against the GenBank protein (genpept) database. Columns 1 and 2 show the polypeptide sequence identification number (Polypeptide SEQ ID NO:) and the corresponding Incyte polypeptide sequence number (Incyte Polypeptide ID) for polypeptides of the invention Column 3 shows the GenBank identification number (Genbank ID NO:) of the nearest GenBank homolog. Column 4 shows the probability score for the match between each polypeptide and its GenBank homolog. Column 5 shows the annotation of the GenBank homolog along with relevant citations where applicable, all of which are expressly incorporated by reference herein.

Table 3 shows various structural features of the polypeptides of the invention. Columns 1 and 2 show the polypeptide sequence identification number (SEQ ID NO:) and the corresponding Incyte polypeptide sequence number (Incyte Polypeptide ID) for each polypeptide of the invention. Column 3 shows the number of amino acid residues in each polypeptide. Column 4 shows potential phosphorylation sites, and column 5 shows potential glycosylation sites, as determined by the MOTIFS program of the GCG sequence analysis software package (Genetics Computer Group, Madison Wis.). Column 6 shows amino acid residues comprising signature sequences, domains, and motifs. Column 7 shows analytical methods for protein structure/function analysis and in some cases, searchable databases to which the analytical methods were applied.

Together, Tables 2 and 3 summarize the properties of polypeptides of the invention, and these properties establish that the claimed polypeptides are proteases. For example, SEQ ID NO:1 is 89% identical to a human preprocathepsin L precursor (GenBank ID g190418) as determined by the Basic Local Alignment Search Tool (BLAST). (See Table 2.) The BLAST probability score is 4.5e–169, which indicates the probability of obtaining the observed polypeptide sequence alignment by chance. SEQ ID NO:1 also contains a papain family cysteine protease active site domain as determined by searching for statistically significant matches in the hidden Markov model (HMM)-based PFAM database of conserved protein family domains. (See Table 3.) The presence of this motif is confirmed by BLIMPS, MOTIFS, and PROFILESCAN analyses, providing further corroborative evidence that SEQ ID NO:1 is a cysteine protease of the papain family. In an alternative example, SEQ ID NO:6 has 44% local identity to *Xenopus* ovochymase, a polyprotease of the trypsin family (GenBank ID g2981641), as determined by the Basic Local Alignment Search Tool (BLAST). (See Table 2.) The BLAST probability score is 6.4e–201, which indicates the probability of obtaining the observed polypeptide sequence alignment by chance. SEQ ID NO:6 contains a number of protease active site domains as determined by searching for statistically significant matches in the hidden Markov model (HMM)-based PFAM database of conserved protein family domains. (See Table 3.) The presence of these motifs is confirmed by BLIMPS, MOTIFS, and PROFILESCAN analyses. These analyses also reveal the presence of kringle and CUB domains, as well as a signal peptide. Together, these data provide further corroborative evidence that SEQ ID NO:6 is a serine protease of the trypsin family. In an alternative example, SEQ ID NO:10 is 50% identical to a human ubiquitin-specific processing protease (GenBank ID g6941888) as determined by the Basic Local Alignment Search Tool (BLAST). (See Table 2.) The BLAST probability score is 7.5e–273, which indicates the probability of obtaining the observed polypeptide sequence alignment by chance. SEQ ID NO:10 is also 51% identical to a murine ubiquitin-specific processing protease (GenBank ID g6941890) as determined by the BLAST analysis with a probability score of 4.0e–271. SEQ ID NO:10 also contains ubiquitin carboxyl-terminal hydrolase (i.e., ubiquitin-specific protease) domains as determined by searching for statistically significant matches in the hidden Markov model (HMM)-based PFAM database of conserved protein family domains. (See Table 3.) Data from BLIMPS and MOTIFS analyses provide further corroborative evidence that SEQ ID NO:10 is a ubiquitin-specific protease. In an alternative example, SEQ ID NO:16 has 52% local identity to *Xenopus* ADAM13 (GenBank ID g1916617) as determined by the Basic Local Alignment Search Tool (l3LAST). (See Table 2.) The BLAST probability score is 1.4e–198, which indicates the probability of obtaining the observed polypeptide sequence alignment by chance. SEQ ID NO:16 contains a reprolysin family neutral zinc protease active site domain, a reprolysin family propeptide, and a disintegrin domain signature as determined by searching for statistically significant matches in the hidden Markov model (HMM)-based PFAM database of conserved protein family domains. (See Table 3.) The presence of these domains is confirmed by BLIMPS, MOTIFS, and PROFILESCAN analyses, providing further corroborative evidence that SEQ ID NO:16 is a metalloprotease of the ADAM family. In an alternative example, SEQ ID NO:17 is 30% identical to the human zinc metalloprotease ADAMTS6 (GenBank ID g5923786) as determined by CLUSTAL V analysis, and 44% local identity, as determined by the Basic Local Alignment Search Tool (BLAST). (See Table 2.) The BLAST probability score is 9.1e–164, which indicates the probability of obtaining the observed polypeptide sequence alignment by chance. SEQ ID NO:17 also contains a zinc metalloprotease active site domain, a reprolysin family metalloprotease propeptide, and a type I thrombospondin domain as determined by searching for statistically significant matches in the hidden Markov model (HMM)-based PFAM database of conserved protein family domains. (See Table 3.) Data from BLIMPS analysis provide further corroborative evidence that SEQ ID NO:17 is a metalloprotease of the ADAMTS family. SEQ ID NO:2–5, SEQ ID NO:7–9, and SEQ ID NO: 11–15 were analyzed and annotated in a similar manner. The algorithms and parameters for the analysis of SEQ ID NO:1–17 are described in Table 7.

As shown in Table 4, the full length polynucleotide sequences of the present invention were assembled using cDNA sequences or coding (exon) sequences derived from genomic DNA, or any combination of these two types of sequences. Columns 1 and 2 list the polynucleotide sequence identification number (Polynucleotide SEQ ID NO:) and the corresponding Incyte polynucleotide consensus sequence number (Incyte Polynucleotide ID) for each polynucleotide of the invention. Column 3 shows the length of each polynucleotide sequence in basepairs. Column 4 lists fragments of the polynucleotide sequences which are useful, for example, in hybridization or amplification technologies that identify SEQ ID NO:18–34 or that distinguish between SEQ ID NO:18–34 and related polynucleotide sequences. Column 5 shows identification numbers corresponding to cDNA sequences, coding sequences (exons) predicted from genomic DNA, and/or sequence assemblages comprised of both cDNA and genomic DNA. These sequences were used to assemble the full length polynucleotide sequences of the invention. Columns 6 and 7 of Table 4 show the nucleotide start (5') and stop (3') positions of the cDNA and/or genomic sequences in column 5 relative to their respective full length sequences.

The identification numbers in Column 5 of Table 4 may refer specifically, for example, to Incyte cDNAs along with their corresponding cDNA libraries. For example, 6917460H1 is the identification number of an Incyte cDNA sequence, and PLACFER06 is the cDNA library from which it is derived. Incyte cDNAs for which cDNA libraries are not indicated were derived from pooled cDNA libraries (e.g., 72004319V1). Alternatively, the identification numbers in column 5 may refer to GenBak cDNAs or ESTs (e.g., g1365166) which contributed to the assembly of the fall length polynucleotide sequences. In addition, the identification numbers in column 5 may identify sequences derived from the ENSEMBL (The Sanger Centre, Cambridge, UK) database (i.e., those sequences including the designation "ENST"). Alternatively, the identification numbers in column 5 may be derived from the NCBI RefSeq Nucleotide Sequence Records Database (ie., those sequences including the designation "NM" or "NT") or the NCBI RefSeq Protein Sequence Records (i.e., those sequences including the designation "NP"). Alternatively, the identification numbers in column 5 may refer to assemblages of both cDNA and Genscan-predicted exons brought together by an "exon stitching" algorithm. For example, FL_XXXXXX_$N_1$_$N_2$_YYYYY_$N_3$_$N_4$ represents a "stitched" sequence in which XXXXXX is the identification number of the cluster of sequences to which the algorithm was applied, and YYYYY is the number of the prediction generated by the algorithm, and $N_{1,2,3...}$, if present, represent specific exons that may have been manually edited during analysis (See Example V). Alternatively, the identification numbers in column 5 may refer to assemblages of exons brought together by an "exon-stretching" algorithm. For example, FLXXXXXX_gAAAAA_gBBBBB_1_N is the identification number of a "stretched" sequence, XXXXXX being the Incyte project identification number, gAAAAA being the GenBank identification number of the human genomic sequence to which the "exon-stretching" algorithm was applied, gBBBBB being the GenBank identification number or NCBI RefSeq identification number of the nearest GenBank protein homolog, and N referring to specific exons (See Example V). In instances where a RefSeq sequence was used as a protein homolog for the "exon-stretching" algorithm, a RefSeq identifier (denoted by "NM" "NP," or "NT") may be used in place of the GenBank identifier (i.e., gBBBBB).

Alternatively, a prefix identifies component sequences that were hand-edited, predicted from genomic DNA sequences, or derived from a combination of sequence analysis methods. The following Table lists examples of component sequence prefixes and corresponding sequence analysis methods associated with the prefixes (see Example IV and Example V).

| Prefix | Type of analysis and/or examples of programs |
| --- | --- |
| GNN, GFG, ENST | Exon prediction from genomic sequences using, for example, GENSCAN (Stanford University, CA, USA) or FGENES (Computer Genomics Group, The Sanger Centre, Cambridge, UK). |
| GBI | Hand-edited analysis of genomic sequences. |
| FL | Stitched or stretched genomic sequences (see Example V). |
| INCY | Full length transcript and exon prediction from mapping of EST sequences to the genome. Genomic location and EST composition data are combined to predict the exons and resulting transcript. |

In some cases, Incyte cDNA coverage redundant with the sequence coverage shown in column 5 was obtained to confirm the final consensus polynucleotide sequence, but the relevant Incyte cDNA identification numbers are not shown.

Table 5 shows the representative cDNA libraries for those full length polynucleotide sequences which were assembled using Incyte cDNA sequences. The representative cDNA library is the Incyte cDNA library which is most frequently represented by the Incyte cDNA sequences which were used to assemble and confirm the above polynucleotide sequences. The tissues and vectors which were used to construct the cDNA libraries shown in Table 5 are described in Table 6.

The invention also encompasses PRTS variants. A preferred PRTS variant is one which has at least about 80%, or alternatively at least about 90%, or even at least about 95% amino acid sequence identity to the PRTS amino acid sequence, and which contains at least one functional or structural characteristic of PRTS.

The invention also encompasses polynucleotides which encode PRTS. In a particular embodiment, the invention encompasses a polynucleotide sequence comprising a sequence selected from the group consisting of SEQ ID NO:18–34, which encodes PRTS. The polynucleotide sequences of SEQ ID NO:18–34, as presented in the Sequence Listing, embrace the equivalent RNA sequences, wherein occurrences of the nitrogenous base thymine are replaced with uracil, and the sugar backbone is composed of noose instead of deoxyribose.

The invention also encompasses a variant of a polynucleotide sequence encoding PRTS. In particular, such a variant polynucleotide sequence will have at least about 70%, or alternatively at least about 85%, or even at least about 95% polynucleotide sequence identity to the polynucleotide sequence encoding PRTS. A particular aspect of the invention encompasses a variant of a polynucleotide sequence comprising a sequence selected from the group consisting of SEQ ID NO:18–34 which has at least about 70%, or alternatively at least about 85%, or even at least about 95% polynucleotide sequence identity to a nucleic acid sequence selected from the group consisting of SEQ ID NO:18–34. Any one of the polynucleotide variants described above can encode an amino acid sequence which contains at least one functional or structural characteristic of PRTS.

It will be appreciated by those skilled in the art that as a result of the degeneracy of the genetic code, a multitude of polynucleotide sequences encoding PRTS, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring PRTS, and all such variations are to be considered as being specifically disclosed.

Although nucleotide sequences which encode PRTS and its variants are generally capable of hybridizing to the nucleotide sequence of the naturally occuring PRTS under appropriately selected conditions of stringency, it may be advantageous to produce nucleotide sequences encoding PRTS or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PRTS and its derivatives without altering the encoded amino acid sequences include the production of RNA transcripts having more desirable properties, such as a greater half-life, than transcripts produced from the naturally occurring sequence.

The invention also encompasses production of DNA sequences which encode PRTS and PRTS derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding PRTS or any fragment thereof.

Also encompassed by the invention are polynucleotide sequences that are capable of hybridizing to the claimed polynucleotide sequences, and, in particular, to those shown in SEQ ID NO:18–34 and fragments thereof under various conditions of stringency. (See, e.g., Wahl G. M. and S. L. Berger (1987) Methods Enzymol. 152:399–407; Kimmel, A. R. (1987) Methods Enzymol. 1521:507–511.) Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Applied Biosystems), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 liquid transfer system (Hamilton, Reno Nev.), PTC200 thermal cycler (MJ Research, Watertown Mass.) and ABI CATALYST 800 thermal cycler (Applied Biosystems). Sequencing is then carried out using either the ABI 373 or 377 DNA sequencing system (Applied Biosystems), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856–853.)

The nucleic acid sequences encoding PRTS may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences inhuman and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–3060). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Applied Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode PRTS may be cloned in recombinant DNA molecules that direct expression of PRTS, or fragments or functional equivalents thereof, in appropriate host cells. Due to the inherent degeneracy of the genetic code, other DNA sequences which encode substantially the same or a functionally equivalent amino acid sequence may be produced and used to express PRTS.

The nucleotide sequences of the present invention can be engineered using methods generally known in the art in order to alter PRTS-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULARBREEDING (Maxygen Inc., Santa Clara Calif.; described in U.S. Pat. No. 5,837,458; Chang, C.-C. et al. (1999) Nat. Biotechnol. 17:793–797; Christians, F. C. et al. (1999) Nat. Biotechnol. 17:259–264; and Crameri, A. et al. (1996) Nat. Biotechnol. 14:315–319) to alter or improve the biological properties of PRTS, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, sequences encoding PRTS may be synthesized, in whole or in part, using chemical methods well known in the art. (See, e.g., Caruthers, M. H. et al. (1980) Nucleic Acids Symp. Ser. 7:215–223; and Horn, T. et al. (1980) Nucleic Acids Symp. Ser. 7:225–232.)

Alternatively, PRTS itself or a fragment thereof may be synthesized using chemical methods. For example, peptide synthesis can be performed using various solution-phase or solid-phase techniques. (See, e.g., Creighton, T. (1984) *Proteins, Structures and Molecular Properties*, W H Freeman, New York N.Y., pp. 55–60; and Roberge, J. Y. et al. (1995) Science 269:202–204.) Automated synthesis may be achieved using the ABI 431A peptide synthesizer (Applied Biosystems). Additionally, the amino acid sequence of PRTS, or any part thereof, may be altered during direct synthesis and/or combined with sequences from other proteins, or any part thereof, to produce a variant polypeptide or a polypeptide having a sequence of a naturally occurring polypeptide.

The peptide may be substantially purified by preparative high performance liquid chromatography. (See, e.g., Chiez, R. M. and F. Z. Regnier (1990) Methods Enzymol. 182:392–421.) The composition of the synthetic peptides may be confirmed by amino acid analysis or by sequencing. (See, e.g., Creighton, supra, pp. 29–53.)

In order to express a biologically active PRTS, the nucleotide sequences encoding PRTS or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding PRTS. Such elements may vary in their strength and specificity. Specific initiation signals may also be used to achieve more efficient translation of sequences encoding PRTS. Such signals include the ATG initiation codon and adjacent sequences, e.g. the Kozak sequence. In cases where sequences encoding PRTS and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding PRTS and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview N.Y., ch. 4, 8, and 16–17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding PRTS. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Sambrook, supra; Ausubel, supra; Van Heeke, G. and S. M. Schuster (1989) J. Biol. Chem. 264:5503–5509; Engelhard, E. K. et al. (1994) Proc. Natl. Acad. Sci USA 91:3224–3227; Sandig, V. et al. (1996) Hum. Gene Ther. 7:1937–1945; Takamatsu, N. (1987) EMBO J. 6:307–311; *The McGraw Hill Yearbook of Science and Technology* (1992) McGraw Hill, New York N.Y., pp. 191–196; Logan, J. and T. Shenk (1984) Proc. Natl. Acad. Sci USA 81:3655–3659; and Harrington, J. J. et al. (1997) Nat. Genet. 15:345–355.) Expression vectors derived from retroviruses, adenoviruses, or herpes or vaccinia viruses, or from various bacterial plasmids, may be used for delivery of nucleotide sequences to the targeted organ, tissue, or cell population. (See, e.g., Di Nicola, M. et al. (1998) Cancer Gen. Ther. 5(6):350–356; Yu, M. et al. (1993) Proc. Natl Acad. Sci. USA 90(13):6340–6344; Buller, R. M. et al. (1985) Nature 317(6040):813–815; McGregor, D. P. et al. (1994) Mol. Immunol. 31(3):219–226; and Verma, J. M. and N. Somia (1997) Nature 389:239–242.) The invention is not limited by the host cell employed.

In bacterial systems, a number of cloning and expression vectors may be selected depending upon the use intended for polynucleotide sequences encoding PRTS. For example, routine cloning, subcloning, and propagation of polynucleotide sequences encoding PRTS can be achieved using a multifunctional *E. coli* vector such as PBLUESCRIPT (Stratagene, La Jolla Calif.) or PSPORT1 plasmnid (Life Technologies). Ligation of sequences encoding PRTS into the vector's multiple cloning site disrupts the lacZ gene, allowing a colorimetric screening procedure for identification of transformed bacteria containing recombinant molecules. In addition, these vectors may be useful for in vitro transcription, dideoy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of PRTS are needed, e.g. for the production of antibodies, vectors which direct high level expression of PRTS may be used. For example, vectors containing the strong, inducible SP6 or T7 bacteriophage promoter may be used.

Yeast expression systems may be used for production of PRTS. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel 1995, supra; Bitter, G. A. et al. (1987) Methods Enzymol. 153:516–544; and Scorer, C. A. et al. (1994) Bio/Technology 12:181–184.)

Plant systems may also be used for expression of PRTS. Transcription of sequences encoding PRTS may be driven by viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs canbe introduced into plant cells by direct DNA transformation or pathogen-mediated transfection. (See, e.g., *The McGraw Bill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding PRTS may be ligated into an adenovirus transcription/translation complex consisting of the late promoter and tripartite leader sequence. Insertion in a non-essential E1 or E3 region of the viral genome may be used to obtain infective virus which expresses PRTS in host cells. (See, e.g., Logan, J. and T. Shenk (1984) Proc. Natl. Acad. Sci. USA 81:3655–3659.) In addition, transcription enhancers, such as the Rous sarcoma virus (RSV) enhancer, may be used to increase expression in mammalian host cells. SV40 or EBV-based vectors way also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345–355.)

For long term production of recombinant proteins in mammalian systems, stable expression of PRTS in cell lines is preferred. For example, sequences encoding PRTS can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk and apr cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G418; and als and pat confer resistance to chlorsulfuron and phosphinotricin acetyltransferase, respectively. (See, e.g., Wigler, M. et al. (1980) Proc. Natl. Acad. Sci. USA 77:3567–3570; Colbere-Garapin, F. et al. (1981) J. Mol. Biol. 150:1–14.) Additional selectable genes have been described, e.g., rpB and hisD, which alter cellular requirements for metabolites. (See, e.g., Hartman, S. C. and R. C. Mulligan (1988) Proc. Natl. Acad. Sci. USA 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding PRTS is inserted within a marker gene sequence, transformed cells containing sequences encoding PRTS can be identified by the absence of marker gene function. Alternatively, a marker gene can be placed in tandem with a sequence encoding PRTS under the control of a single promoter. Expression of the marker gene in response to induction or selection usually indicates expression of the tandem gene as well.

In general, host cells that contain the nucleic acid sequence encoding PRTS and that express PRTS may be identified by a variety of procedures known to those of skill in the art. These procedures include, but are not limited to, DNA—DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of PRTS using either specific polyclonal or monoclonal anti-bodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on PRTS is preferred, but a competitive binding assay may be employed. These and other assays are well known in the art. (See, e.g., Hampton, R. et al. (1990) *Serological Methods, a Laboratory Manual*, APS Press, St. Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.)

A wide variety of labels and conjugation techniques are known by those skilled in the art and may be used in various nucleic acid and amino acid assays. Means for producing labeled hybridization or PCR probes for detecting sequences related to polynucleotides encoding PRTS include oligolabeling, nick translation, end-labeling, or PCR amplification using a labeled nucleotide. Alternatively, the sequences encoding PRTS, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inlibitors, magnetic particles, and the like.

Host cells transformed with nucleotide sequences encoding PRTS may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode PRTS may be designed to contain signal sequences which direct secretion of PRTS through a prokaryotic or eukayotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and WI38) are available from the American Type Culture Collection (ATCC, Manassas Va.) and may be chosen to ensure the correct modification and processing of the foreign protein.

In another embodiment of the invention, natural, modified, or recombinant nucleic acid sequences encoding PRTS may be ligated to a heterologous sequence resulting in translation of a fusion protein in any of the aforementioned host systems. For example, a chimeric PRTS protein containing a heterologous moiety that can be recognized by a commercially available antibody may facilitate the screening of peptide libraries for inhibitors of PRTS activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calrnodulin, and metal-chelate resins, respectively. FLAG, c-myc, and hemagglutinin (A) enable immunoaffinity purification of fusion proteins using commercially available monoclonal and polyclonal antibodies that specifically recognize these epitope tags. A fusion protein may also be engineered to contain a proteolytic cleavage site located between the PRTS encoding sequence and the heterologous protein sequence, so that PRTS may be cleaved away from the heterologous moiety following purification. Methods for fusion protein expression and purification are discussed in Ausubel (1995, supra, ch. 10). A variety of commercially available kits may also be used to facilitate expression and purification of fusion proteins.

In a further embodiment of the invention, synthesis of radiolabeled PRTS may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

PRTS of the present invention or fragments thereof may be used to screen for compounds that specifically bind to PRTS. At least one and up to a plurality of test compounds may be screened for specific binding to PRTS. Examples of test compounds include antibodies, oligonucleotides, proteins (e.g., receptors), or small molecules.

In one embodiment, the compound thus identified is closely related to the natural ligand of PRTS, e.g., a ligand or fragment thereof, a natural substrate, a structural or functional mimetic, or a natural binding partner. (See, e.g., Coligan, J. E. et al. (1991) Current Protocols in Immunology 1(2): Chapter 5.) Similarly, the compound can be closely related to the natural receptor to which PRTS binds, or to at least a fragment of the receptor, e.g., the ligand binding site. In either case, the compound can be rationally designed using known techniques. In one embodiment, screening for these compounds involves producing appropriate cells which express PRTS, either as a secreted protein or on the cell membrane. Preferred cells include cells from mammals, yeast, Drosophila, or E. coli. Cells expressing PRTS or cell membrane fractions which contain PRTS are then contacted with a test compound and binding, stimulation, or inhibition of activity of either PRTS or the compound is analyzed.

An assay may simply test binding of a test compound to the polypeptide, wherein binding is detected by a fluorophore, radioisotope, enzyme conjugate, or other detectable label. For example, the assay may comprise the steps of combing at least one test compound with PRTS, either in solution or affixed to a solid support, and detecting the binding of PRTS to the compound. Alternatively, the assay may detect or measure binding of a test compound in the presence of a labeled competitor. Additionally, the assay may be carried out using cell-free preparations, chemical libraries, or natural product mixtures, and the test compound (s) may be free in solution or affixed to a solid support.

PRTS of the present invention or fragments thereof may be used to screen for compounds that modulate the activity of PRTS. Such compounds may include agonists, antagonists, or partial or inverse agonists. In one embodiment, an assay is performed under conditions permissive for PRTS activity, wherein PRTS is combined with at least one test compound, and the activity of PRTS in the presence of a test compound is compared with the activity of PRTS in the absence of the test compound. A change in the activity of PRTS in the presence of the test compound is indicative of a compound that modulates the activity of PRTS. Alternatively, a test compound is combined with an in vitro or cell-free system comprising PRTS under conditions suitable for PRTS activity, and the assay is performed. In either of these assays, a test compound which modulates the activity of PRTS may do so indirectly and need not come in direct contact with the test compound. At least one and up to a plurality of test compounds may be screened.

In another embodiment, polynucleotides encoding PRTS or their mammalian homologs may be "knocked out" in an animal model system using homologous recombination in embryonic stem (ES) cells. Such techniques are well known in the art and are useful for the generation of animal models of human disease. (See, e.g., U.S. Pat. No. 5,175,383 and U.S. Pat. No. 5,767,337.) For example, mouse ES cells, such as the mouse 129/SvJ cell line, are derived from the early mouse embryo and grown in culture. The ES cells are transformed with a vector containing the gene of interest disrupted by a marker gene, e.g., the neomycin phosphotransferase gene (neo; Capecchi, M. R. (1989) Science 244:1288–1292). The vector integrates into the corresponding region of the host, genome byhomologous recombination. Alternatively, homologous recombination takes place using the Cre-loxP system to knockout a gene of interest in a tissue- or developmental stage-specific manner (Marth, J. D. (1996) Clin. Invest. 97:1999–2002; Wagner, K. U. et al. (1997) Nucleic Acids Res. 25:4323–4330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Transgenic animals thus generated may be tested with potential therapeutic or toxic agents.

Polynucleotides encoding PRTS may also be manipulated in vitro in ES cells derived from human blastocysts. Human ES cells have the potential to differentiate into at least eight separate cell lineages including endoderm, mesoderm, and ectodermal cell types. These cell lineages differentiate into, for example, neural cells, hematopoietic lineages, and cardiomyocytes (Thomson, J. A. et al. (1998) Science 282:1145–1147).

Polynucleotides encoding PRTS can also be used to create "iocin" humanized animals (pigs) or transgenic animals (mice or rats) to model human disease. With knockin technology, a region of a polynucleotide encoding PRTS is injected into animal ES cells, and the injected sequence integrates into the animal cell genome. Transformed cells are injected into blastulae, and the blastulae are implanted as described above. Transgenic progeny or inbred lines are studied and treated with potential pharmaceutical agents to obtain information on treatment of a human disease. Alternatively, a mammal inbred to overexpress PRTS, e.g., by secreting PRTS in its milk, may also serve as a convenient source of that protein (Janne, J. et al. (1998) Biotechnol. Annu. Rev. 4:55–74).

Therapeutics

Chemical and structural similarity, e.g., in the context of sequences and motifs, exists between regions of PRTS and proteases. In addition, the expression of PRTS is closely associated with digestive, lung, neurological, gastrointestinal cardiovascular, urinary, reproductive, fibroblastic, developmental, and endothelial tissues, and also prostate cancer and other tumorous tissue. Therefore, PRTS appears to play a role in gastrointestinal, cardiovascular, autoimmune/inflammatory, cell proliferative, developmental, epithelial, neurological, and reproductive disorders. In the treatment of disorders associated with increased PRTS expression or activity, it is desirable to decrease the expression or activity of PRTS. In the treatment of disorders associated with decreased PRTS expression or activity, it is desirable to increase the expression or activity of PRTS.

Therefore, in one embodiment, PRTS or a fragment or derivative thereof may be administered to a subject to treat or prevent a disorder associated with decreased expression or activity of PRTS. Examples of such disorders include, but are not limited to, a gastrointestinal disorder, such as dysphagia, peptic esophagitis, esophageal spasm, esophageal stricture, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatitis, hyperbilirubinemia, cirrhosis, passive congestion of the liver, hepatoma, infectious colitis, ulcerative colitis, ulcerative proctitis, Crohn's disease, Whipple's disease, Mallory-Weiss syndrome, colonic carcinoma, colonic obstruction, irritable bowel syndrome, short bowel syndrome, diarrhea, constipation, gastrointestinal hemorrhage, acquired immunodeficiency syndrome (AIDS) enteropathy, jaundice, hepatic encephalopathy, hepatorenal syndrome, hepatic steatosis, hemochromatosis, Wilson's disease, alpha$_1$-antitrypsin deficiency, Reye's syndrome, primary sclerosing cholangitis, liver infarction, portal vein obstruction and thrombosis, centrilobular necrosis, peliosis hepatis, hepatic vein thrombosis, veno-occlusive disease, preeclampsia, eclampsia, acute fatty liver of pregnancy, intrahepatic cholestasis of pregnancy, and hepatic tumors including nodular hyperplasias, adenonias, and carcinomas; a cardiovascular disorder, such as arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation; an autoimmune/inflammatory disorder, such as acquired immunodeficiency syndrome (AIDS), Addison's disease, adult respiratory distress syndrome, allergies, ankylosing spondylitis, amyloidosis, anemia, asthma, atherosclerosis, atherosclerotic plaque rupture, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, degradation of articular cartilage, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a developmental disorder, such as renal tubular acidosis, anemia, Cushing's syndrome, achondroplastic dwarfism, Duchenne and Becker muscular dystrophy, bone resorption, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary nueuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, age-related macular degeneration, and sensorineural hearing loss; an epithelial disorder, such as dyshidrotic eczema, allergic contact dermatitis, keratosis pilaris, melasma, vitiligo, actinic keratosis, basal cell carcinoma, squamous cell carcinoma, seborrheic keratosis, folliculitis, herpes simplex, herpes zoster, varicella, candidiasis, dermatophytosis, scabies, insect bites, cherry angioma, keloid, dermatofibroma, acrochordons, urticaria, transient acantholytic dermatosis, xerosis, eczema, atopic dermatitis, contact dermatitis, hand eczema, nummular eczema, lichen simplex chronicus, asteatotic eczema, stasis dermatitis and stasis ulceration, seborrheic dermatitis, psoriasis, lichen planus, pityriasis rosea, impetigo, ecthyma, dermatophytosis, tinea versicolor, warts, acne vulgaris, acne rosacea, pemphigus vulgaris, pemphigus foliaceus, paraneoplastic pemphigus, bullous pemphigoid, herpes gestationis, dermatitis herpetiformis, linear IgA disease, epidermolysis bullosa acquisita, dermatomyositis, lupus erythematosus, scleroderma and morphea, erythroderma, alopecia, figurate skin lesions, telangiectasias, hypopigmentation, hyperpigmentation, vesicles/bullae, exanthems, cutaneous drug reactions, papulonodular skin lesions, chronic non-healing wounds, photosensitivity diseases, epidermolysis bullosa simplex, epidermolytic hyperkeratosis, epidernolytic and nonepideimolytic palmoplantar keratoderma, ichthyosisbullosa of Siemens, ichthyosis exfoliativa, keratosis palmaris et plantaris, keratosis palmoplantaris, palmoplantar keratoderma, keratosis punctata, Meesmann's corneal dystrophy, pachyonychia congenita, white sponge nevus, steatocystoma multiplex, epidermal nevi/epidermolytic hyperleratosis type, monilethrix, trichothiodystrophy, chronic hepatitis/cryptogenic cirrhosis, and colorectal hyperplasia; a neurological disorder, such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; and a reproductive disorder, such as infertility, including tubal disease, ovulatory defects, and endometriosis, a disorder of prolactin production, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis; cancer of the breast, fibrocystic breast disease, and galactorrhea; a disruption of spermatogenesis, abnormal sperm physiology, cancer of the testis, cancer of the prostate, benign prostatic hyperplasia, prostatitis, Peyronie's disease, impotence, carcinoma of the male breast, and gynecomastia.

In another embodiment, a vector capable of expressing PRTS or a fragment or derivative thereof may be administered to a subject to treat or prevent a disorder associated with decreased expression or activity of PRTS including, but not limited to, those described above.

In a further embodiment, a composition comprising a substantially purified PRTS in conjunction with a suitable pharmaceutical carrier may be administered to a subject to treat or prevent a disorder associated with decreased expression or activity of PRTS including, but not limited to, those provided above.

In still another embodiment, an agonist which modulates the activity of PRTS may be administered to a subject to treat or prevent a disorder associated with decreased expression or activity of PRTS including, but not limited to, those listed above.

In a further embodiment, an antagonist of PRTS may be administered to a subject to treat or prevent a disorder associated with increased expression or activity of PRTS. Examples of such disorders include, but are not limited to, those gastrointestinal, cardiovascular, autoimmune/inflammatory, cell proliferative, developmental, epithelial, neurological, and reproductive disorders described above. In one aspect, an antibody which specifically binds PRTS may be used directly as an antagonist or indirectly as a targeting or delivery mechanism for bringing a pharmaceutical agent to cells or tissues which express PRTS.

In an additional embodiment, a vector expressing the complement of the polynucleotide encoding PRTS may be administered to a subject to treat or prevent a disorder associated with increased expression or activity of PRTS including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PRTS may be produced using methods which are generally known in the art. In particular, purified PRTS may be used to produce antibodies or to screen libraries of pharmaceutical agents to identify those which specifically bind PRTS. Antibodies to PRTS may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are generally preferred for therapeutic use.

For the production of antibodies, various hosts including goats, rabbits, rats, mice, humans, and others may be immunized by injection with PRTS or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to PRTS have an amino acid sequence consisting of at least about 5 amino acids, and generally will consist of at least about 10 amino acids. It is also preferable that these oligopeptides, peptides, or fragments are identical to a portion of the amino acid sequence of the natural protein. Short stretches of PRTS amino acids may be fused with those of another protein, such as KLH, and antibodies to the chimeric molecule may be produced.

Monoclonal antibodies to PRTS may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kobler, G. et al. (1975) Nature 256:495–497; Kozbor, D. et al. (1985) J. Immunol. Methods 81:31–42; Cote, R. J. et al. (1983) Proc. Natl. Acad. Sci. USA 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. USA 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce PRTS-specific single chain antibodies. Antibodies with related specificity, but of distinct idiotypic composition, may be generated by chain shuffling from random combinatorial-immuno globul libraries. (See, e.g., Burton, D. R. (1991) Proc. Natl. Acad. Sci. USA 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833–3837; Winter, G. et al. (1991) Nature 349:293–299.)

Antibody fragments which contain specific binding sites for PRTS may also be generated. For example, such fragments include, but are not limited to, $F(ab')_2$ fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such inmmunoassays typically involve the measurement of complex formation between PRTS and its specific antibody. A two-site, monoclonal-based immunoassays utilizing monoclonal antibodies reactive to two non-interfering PRTS epitopes is generally used, but a competitive binding assay may also be employed (Pound, supra).

Various methods such as Scatchard analysis in conjunction with radioimmunoassay techniques may be used to assess the affinity of antibodies for PRTS. Affinity is expressed as an association constant, $K_a$, which is defined as the molar concentration of PRTS-antibody complex divided by the molar concentrations of free antigen and free antibody under equilibrium conditions. The $K_a$ determined for a preparation of polyclonal antibodies, which are heterogeneous in their affinities for multiple PRTS epitopes, represents the average affinity, or avidity, of the antibodies for PRTS. The $K_a$ determined for a preparation of monoclonal antibodies, which are monospecific for a particular PRTS epitope, represents a true measure of affinity. High-affinity antibody preparations with $K_a$ ranging from about $10^9$ to $10^{12}$ L/mole are preferred for use in immunoassays in which the PRTS-antibody complex must withstand rigorous manipulations. Low-affinity antibody preparations with $K_a$ ranging from about $10^6$ to $10^7$ L/mole are preferred for use in immunopurification and similar procedures which ultimately require dissociation of PRTS, preferably in active form, from the antibody (Catty, D. (1988) Antibodies, Volume I: A Practical Approach, IRL Press, Washington D.C.; Liddell, J. E. and A. Cryer (1991) A Practical Guide to Monoclonal Antibodies, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is generally employed in procedures requiring precipitation of PRTS-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding PRTS, or any fragment or complement thereof, may be used for therapeutic purposes. In one aspect, modifications of gene expression can be achieved by designing complementary sequences or antisense molecules (DNA, RNA, PNA, or modified oligonucleotides) to the coding or regulatory regions of the gene encoding PRTS. Such technology is well known in the art, and antisense oligonucleotides or larger fragments can be designed from various locations along the coding or control regions of sequences encoding PRTS. (See, e.g., Agrawal, S., ed. (1996) Antisense Therapeutics, Humana Press Inc., Totawa N.J.)

In therapeutic use, any gene delivery system suitable for introduction of the antisense sequences into appropriate target cells can be used. Antisense sequences can be delivered intracellularly in the form of an expression plasmid which, upon transcription, produces a sequence complementary to at least a portion of the cellular sequence encoding the target protein. (See, e.g., Slater, J. E. et al. (1998) J. Allergy Clin. Immunol. 102(3):469–475; and Scanlon, K. J. et al. (1995) 9(13):1288–1296.) Antisense sequences can also be introduced intracellularly through the use of viral vectors, such as retrovirus and adeno-associated virus vectors. (See, e.g., Miller, A. D. (1990) Blood 76:271; Ausubel, supra; Uckert, W. and W. Walther (1994) Pharmacol. Ther. 63(3):323–347.) Other gene delivery mechanisms include liposome-derived systems, artificial viral envelopes, and other systems known in the art. (See, e.g., Rossi, J. J. (1995) Br. Med. Bull. 51(1):217–225; Boado, R. J. et al. (1998) J. Pharm. Sci. 87(11):1308–1315; and Morris, M. C. et al. (1997) Nucleic Acids Res. 25(14):2730–2736.)

In another embodiment of the invention, polynucleotides encoding PRTS may be used for somatic or germline gene therapy. Gene therapy may be performed to (i) correct a genetic deficiency (e.g., in the cases of severe combined immunodeficiency (SCID)-XI disease characterized by X-linked inheritance (Cavazzana-Calvo, M. et al. (2000) Science 288:669–672), severe combined immunodeficiency syndrome associated with an inherited adenosine deaminase (ADA) deficiency (Blaese, R. M. et al. (1995) Science 270:475–480; Bordignon, C. et al. (1995) Science 270:470–475), cystic fibrosis (Zabner, J. et al. (1993) Cell 75:207–216; Crystal, R. G. et al. (1995) Hum. Gene Therapy 6:643–666; Crystal, R. G. et al. (1995) Hum. Gene Therapy 6:667–703), thalassamias, familial hypercholesterolemia, and hemophilia resulting from Factor VIII or Factor IX deficiencies (Crystal, R. G. (1995) Science 270:404–410; Verma, I. M. and N. Somia (1997) Nature 389:239–242)), (ii) express a conditionally lethal gene product (e.g., in the case of cancers which result from unregulated cell proliferation), or (iii) express a protein which affords protection against intracellular parasites (e.g., against human retroviruses, such as human immunodeficiency virus (HIV) (Baltimore, D. (1988) Nature 335:395–396; Poeschla, E. et al. (1996) Proc. Natl. Acad. Sci. USA. 93:11395–11399), hepatitis B or C virus (HBV, HCV); fungal parasites, such as *Candida albicans* and *Paracoccidioides brasiliensis*; and protozoan parasites such as *Plasmodium falciparum* and *Trypanosoma cruzi*). In the case where a genetic deficiency in PRTS expression or regulation causes disease, the expression of PRTS from an appropriate population of transduced cells may alleviate the clinical manifestations caused by the genetic deficiency.

In a further embodiment of the invention, diseases or disorders caused by deficiencies in PRTS are treated by constructing mammalian expression vectors encoding PRTS and introducing these vectors by mechanical means into PRTS-deficient cells. Mechanical transfer technologies for use with cells in vivo or ex vitro include (i) direct DNA microinjection into individual cells, (ii) ballistic gold particle delivery, (iii) liposome-mediated transfection, (iv) receptor-mediated gene transfer, and (v) the use of DNA transposons (Morgan, R. A. and W. F. Anderson (1993) Annu. Rev. Biochem. 62:191–217; Ivics, Z. (1997) Cell 91:501–510; Boulay, J-L. and H. Récipon (1998) Curr. Opin. Biotechnol. 9:445–450).

Expression vectors that may be effective for the expression of PRTS include, but are not limited to, the PCDNA 3.1, EPITAG, PRCCMV2, PREP, PVAX, PCR2-TOPOTA vectors (Initrogen, Carlsbad Calif.), PCMV-SCRIPT, PCMV-TAG, PEGSH/PERV (Stratagene, La Jolla, Calif.), and PTET-OFF, PTET-ON, PTRE2, PTRE2-LUC, PTK-HYG (Clontech, Palo Alto Calif.). PRTS may be expressed using (i) a constitutively active promoter, (e.g., from cytomegaloviums (CMV), Rous sarcoma virus (RSV), SV40 virus, thymidine kinase (TK), or β-actin genes), (ii) an inducible promoter (e.g., the tetracycline-regulated promoter (Gossen, M. and H Bujard (1992) Proc. Natl. Acac Sci. USA 89:5547–5551; Gossen, M. et al. (1995) Science 268:1766–1769; Rossi, F. M. V. and H. M. Blau (1998) Curr. Opin. Biotechnol. 9:451–456), commercially available in the T-REX plasmid (Invitrogen)); the ecdysone-inducible promoter (available in the plasmids PVGRXR and PIND; Invitrogen); the FK506/rapamycin inducible promoter; or the RU486/mifepristone inducible promoter (Rossi, F. M. V. and Blau, H. M. supra)), or (iii) a tissue-specific promoter or the native promoter of the endogenous gene encoding PRTS from a normal individual.

Commercially available liposome transformation kits (e.g., the PERFECT LIPID TRANSFECTION KIT, available from Invitrogen) allow one with ordinary skill in the art to deliver polynucleotides to target cells in culture and require minimal effort to optimise experimental parameters. In the alternative, transformation is performed using the calcium phosphate method (Graham, P. L. and A. J. Eb (1973) Virology 52:456–467), or by electroporation (Neumann, E. et al. (1982) EMBO J. 1:841–845). The introduction of DNA to primary cells requires modification of these standardized mammalian transfection protocols.

In another embodiment of the invention, diseases or disorders caused by genetic defects with respect to PRTS expression are treated by constructing a retrovirus vector consisting of (i) the polynucleotide encoding PRTS under the control of an independent promoter or the retrovirus long terminal repeat (LTR) promoter, (ii) appropriate RNA packaging signals, and (iii) a Rev-responsive element (RRE) along with additional retrovirus cis-acting RNA sequences and coding sequences required for efficient vector propagation. Retrovirus vectors (e.g., PFB and PFBNEO) are commercially available (Stratagene) and are based on published data (Riviere, I. et al. (1995) Proc. Natl. Acad. Sci. USA 92:6733–6737), incorporated by reference herein. The vector is propagated in an appropriate vector producing cell line (VPCL) that expresses an envelope gene with a tropism for receptors on the target cells or a promiscuous envelope protein such as VSVg (Armentano, D. et al. (1987) J. Virol. 61:1647–1650; Bender, M. A. et al. (1987) J. Virol. 61:1639–1646; Adam, M. A. and A. D. Miller (1988) J. Virol. 62:3802–3806; Dull, T. et al. (1998) J. Virol. 72:8463–8471; Zufferey, R. et al. (1998) J. Virol. 72:9873–9880). U.S. Pat. No. 5,910,434 to Rigg ("Method for obtaining retrovirus packaging cell lines producing high transducing efficiency retroviral supernatant") discloses a method for obtaining retrovirus packaging cell lines and is hereby incorporated by reference. Propagation of retrovirus vectors, transduction of a population of cells (e.g., CD4+ T-cells), and the return of transduced cells to a patient are procedures well known to persons skilled in the art of gene therapy and have been well documented (Ranga, U. et al. (1997) J. Virol. 71:7020–7029; Bauer, G. et al. (1997) Blood 89:2259–2267; Bonyhadi, M. L. (1997) J. Virol. 71:4707–4716; Ranga, U. et al. (1998) Proc. Natl. Acad. Sci. USA 95:1201–1206; Su, L. (1997) Blood 89:2283–2290).

In the alternative, an adenovirus-based gene therapy delivery system is used to deliver polynucleotides encoding PRTS to cells which have one or more genetic abnormalities with respect to the expression of PRTS. The construction and packaging of adenovirus-based vectors are well known to those with ordinary skill in the art. Replication defective adenovirts vectors have proven to be versatile for importing genes encoding immunoregulatory proteins into intact islets in the pancreas (Csete, M. E. et al. (1995) Transplantation 27:263–268). Potentially useful adenoviral vectors are described in U.S. Pat. No. 5,707,618 to Armentano ("Adenovirus vectors for gene therapy"), hereby incorporated by reference. For adenoviral vectors, see also Antinozzi, P. A. et al. (1999) Annu. Rev. Nutr. 19:511–544 and Verma, L. M. and N. Somia (1997) Nature 18:389:239–242, both incorporated by reference herein.

In another alternative, a herpes-based, gene therapy delivery system is used to deliver polynucleotides encoding PRTS to target cells which have one or more genetic abnormalities with respect to the expression of PRTS. The use of herpes simplex virus (HSV)-based vectors may be especially valuable for introducing PRTS to cells of the central nervous system, for which HSV has a tropism. The construction and packaging of herpes-based vectors are well known to those with ordinary skill in the art. A replication-competent herpes simplex virus (HSV) type 1-based vector has been used to deliver a reporter gene to the eyes of primates (Liu, X. et al. (1999) Exp. Eye Res. 169:385–395). The construction of a HSV-1 virus vector has also been disclosed in detail in U.S. Pat. No. 5,804,413 to DeLuca ("Herpes simplex virus strains for gene transfer"), which is hereby incorporated by reference. U.S. Pat. No. 5,804,413 teaches the use of recombinant HSV d92 which consists of a genome containing at least one exogenous gene to be transferred to a cell under the control of the appropriate promoter for purposes including human gene therapy. Also taught by this patent are the construction and use of recombinant HSV strains deleted for ICP4, ICP27 and ICP22. For HSV vectors, see also Goins, W. F. et al. (1999) J. Virol. 73:519–532 and Xu, H. et al. (1994) Dev. Biol. 163:152–161, hereby incorporated by reference. The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

In another alternative, an alphavirus (positive, single-stranded RNA virus) vector is used to deliver polynucleotides encoding PRTS to target cells. The biology of the prototypic alphavirus, Semliki Forest Virus (SFV), has been studied extensively and gene transfer vectors have been based on the SFV genome (Garoff, H. and K.-J. Li (1998) Curr. Opin. Biotechnol. 9:464–469). During alphavirus RNA replication, a subgenomic RNA is generated that normally encodes the viral capsid proteins. This subgenomic RNA replicates to higher levels than the full length genomic RNA, resulting in the overproduction of capsid proteins relative to the viral proteins with enzymatic activity (e.g., protease and polymerase). Similarly, inserting the coding sequence for PRTS into the alphavirus genome in place of the capsid-coding region results in the production of a large number of PRTS-coding RNAs and the synthesis of high levels of PRTS in vector transduced cells. While alphavirus infection is typically associated with cell lysis within a few days, the ability to establish a persistent infection in hamster normal kidney cells (BHK-21) with a variant of Sindbis virus (SIN) indicates that the lytic replication of alphaviruses can be altered to suit the needs of the gene therapy application (Dryga, S. A. et al. (1997) Virology 228:74–83). The wide host range of alphaviruses will allow the introduction of PRTS into a variety of cell types. The specific transduction of a subset of cells in a population may require the sorting of cells prior to transduction. The methods of manipulating infectious cDNA clones of alphaviruses, performing alphavirus cDNA and RNA transfections, and performing alphavirus infections, are well known to those with ordinary skill in the art.

Oligonucleotides derived from the transcription initiation site, e.g., between about positions −10 and +10 from the start site, may also be employed to inhibit gene expression. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. J. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding PRTS.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PRTS. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

An additional embodiment of the invention encompasses a method for screening for a compound which is effective in altering expression of a polynucleotide encoding PRTS. Compounds which may be effective in altering expression of a specific polynucleotide may include, but are not limited to, oligonucleotides, antisense oligonucleotides, triple helix-forming oligonucleotides, transcription factors and other polypeptide transcriptional regulators, and non-macromolecular chemical entities which are capable of interacting with specific polynucleotide sequences. Effective compounds may alter polynucleotide expression by acting as either inhibitors or promoters of polynucleotide expression. Thus, in the treatment of disorders associated with increased PRTS expression or activity, a compound which specifically inhibits expression of the polynucleotide encoding PRTS may be therapeutically useful, and in the treatment of disorders associated with decreased PRTS expression or activity, a compound which specifically promotes expression of the polynucleotide encoding PRTS may be therapeutically useful.

At least one, and up to a plurality, of test compounds may be screened for effectiveness in altering expression of a specific polynucleotide. A test compound may be obtained by any method commonly known in the art, including chemical modification of a compound known to be effective in altering polynucleotide expression; selection from an existing, commercially-available or proprietary library of naturally-occurring or non-natural chemical compounds; rational design of a compound based on chemical and/or structural properties of the target polynucleotide; and selection from a library of chemical compounds created combinatorially or randomly. A sample comprising a polynucleotide encoding PRTS is exposed to at least one test compound thus obtained. The sample may comprise, for example, an intact or permeabilized cell, or an in vitro cell-free or reconstituted biochemical system. Alterations in the expression of a polynucleotide encoding PRTS are assayed by any method commonly known in the art. Typically, the expression of a specific nucleotide is detected by hybridization with a probe having a nucleotide sequence complementary to the sequence of the polynucleotide encoding PRTS. The amount of hybridization may be quantified, thus forming the basis for a comparison of the expression of the polynucleotide both with and without exposure to one or more test compounds. Detection of a change in the expression of a polynucleotide exposed to a test compound indicates that the test compound is effective in altering the expression of the polynucleotide. A screen for a compound effective in altering expression of a specific polynucleotide can be carried out, for example, using a *Schizosaccharomyces pombe* gene expression system (Atkins, D. et al. (1999) U.S. Pat. No. 5,932,435; Arndt, G. M. et al. (2000) Nucleic Acids Res. 28:E15) or a human cell line such as HeLa cell (Clarke, M. L. et al. (2000) Biochem. Biophys. Res. Commun. 268:8–13). A particular embodiment of the present invention involves screening a combinatorial library of oligonucleotides (such as deoxyribonucleotides, ribonucleotides, peptide nucleic acids, and modified oligonucleotides) for antisense activity against a specific polynucleotide sequence (Bruice, T. W. et al. (1997) U.S. Pat. No. 5,686,242; Bruice, T. W. et al. (2000) U.S. Pat. No. 6,022,691).

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nat. Biotechnol. 15:462–466.)

Any of the therapeutic methods described above may be applied to any subject in need of such therapy, including, for example, mammals such as humans, dogs, cats, cows, horses, rabbits, and monkeys.

An additional embodiment of the invention relates to the administration of a composition which generally comprises an active ingredient formulated with a pharmaceutically acceptable excipient. Excipients may include, for example, sugars, starches, celluloses, gums, and proteins. Various formulations are commonly known and are thoroughly discussed in the latest edition of *Remington's Pharmaceutical Sciences* (Maack Publishing, Easton Pa.). Such compositions may consist of PRTS, antibodies to PRTS, and mimetics, agonists, antagonists, or inhibitors of PRTS.

The compositions utilized in this invention may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Compositions for pulmonary administration may be prepared in liquid or dry powder form. These compositions are generally aerosolized immediately prior to inhalation by the patient. In the case of small molecules (e.g. traditional low molecular weight organic drugs), aerosol delivery of fast-acting formulations is well-known in the art. In the case of macromolecules (e.g. larger peptides and proteins), recent developments in the field of pulmonary delivery via the alveolar region of the lung have enabled the practical delivery of drugs such as insulin to blood circulation (see, e.g., Patton, J. S. et al., U.S. Pat. No. 5,997,848). Pulmonary delivery has the advantage of administration without needle injection, and obviates the need for potentially toxic penetration enhancers.

Compositions suitable for use in the invention include compositions wherein the active ingredients are contained in an effective amount to achieve the intended purpose. The determination of an effective dose is well within the capability of those skilled in the art.

Specialized forms of compositions may be prepared for direct intracellular delivery of macromolecules comprising PRTS or fragments thereof. For example, liposome preparations containing a cell-impermeable macromolecule may promote cell fusion and intracellular delivery of the macromolecule. Alternatively, PRTS or a fragment thereof may be joined to a short cationic N-terminal portion from the HIV Tat-1 protein. Fusion proteins thus generated have been found to transduce into the cells of all tissues, including the brain, in a mouse model system (Schwarze, S. R. et al. (1999) Science 285:1569–1572).

For any compound, the therapeutically effective dose can be estimated initially either in cell culture assays, e.g., of neoplastic cells, or in animal models such as mice, rats, rabbits, dogs, monkeys, or pigs. An animal model may also be used to determine the appropriate concentration range and route of administration. Such information can then be used to determine useful doses and routes for administration in humans.

A therapeutically effective dose refers to that amount of active ingredient, for example PRTS or fragments thereof, antibodies of PRTS, and agonists, antagonists or inhibitors of PRTS, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind PRTS may be used for the diagnosis of disorders characterized by expression of PRTS, or in assays to monitor patients being treated with PRTS or agonists, antagonists, or inhibitors of PRTS. Antibodies useful for diagnostic purposes may be prepared in the same manner as described above for therapeutics. Diagnostic assays for PRTS include methods which utilize the antibody and a label to detect PRTS inhuman body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring PRTS, including ELISAs, RIAs, and FACS, are known in the art and provide a basis for diagnosing altered or abnormal levels of PRTS expression. Normal or standard values for PRTS expression are established by combining body fluids or cell extracts taken from normal mammalian subjects, for example, human subjects, with antibodies to PRTS under conditions suitable for complex formation. The amount of standard complex formation may be quantitated by various methods, such as photometric means. Quantities of PRTS expressed in subject, control, and disease samples from biopsied tissues are compared with the standard values. Deviation between standard and subject values establishes the parameters for diagnosing disease.

In another embodiment of the invention, the polynucleotides encoding PRTS may be used for diagnostic purposes. The polynucleotides which may be used include oligonucleotide sequences, complementary RNA and DNA molecules, and PNAs. The polynucleotides may be used to detect and quantify gene expression in biopsied tissues in which expression of PRTS may be correlated with disease. The diagnostic assay may be used to determine absence, presence, and excess expression of PRTS, and to monitor regulation of PRTS levels during therapeutic intervention.

In one aspect, hybridization with PCR probes which are capable of detecting polynucleotide sequences, including genomic sequences, encoding PRTS or closely related molecules may be used to identify nucleic acid sequences which encode PRTS. The specificity of the probe, whether it is made from a highly specific region, e.g., the 5' regulatory region, or from a less specific region, e.g., a conserved motif, and the stringency of the hybridization or amplification will determine whether the probe identifies only naturally occurring sequences encoding PRTS, allelic variants, or related sequences.

Probes may also be used for the detection of related sequences, and may have at least 50% sequence identity to any of the PRTS encoding sequences. The hybridization probes of the subject invention may be DNA or RNA and may be derived from the sequence of SEQ ID NO:18–34 or from genomic sequences including promoters, enhancers, and introns of the PRTS gene.

Means for producing specific hybridization probes for DNAs encoding PRTS include the cloning of polynucleotide sequences encoding PRTS or PRTS derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding PRTS may be used for the diagnosis of disorders associated with expression of PRTS. Examples of such disorders include, but are not limited to, a gastrointestinal disorder, such as dysphagia, peptic esophagitis, esophageal spasm, esophageal stricture, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatitis, hyperbilirubinemia, cirrhosis, passive congestion of the liver, hepatoma, infectious colitis, ulcerative colitis, ulcerative proctitis, Crohn's disease, Whipple's disease, Mallory-Weiss syndrome, colonic carcinoma, colonic obstruction, irritable. bowel syndrome, short bowel syndrome, diarrhea, constipation, gastrointestinal hemorrhage, acquired immunodeficiency syndrome (AIDS) enteropathy, jaundice, hepatic encephalopathy, hepatorenal syndrome, hepatic steatosis, hemochromatosis, Wilson's disease, $alpha_1$-antitrypsin deficiency, Reye's syndrome, primary sclerosing cholangitis, liver infarction, portal vein obstruction and thrombosis, centrilobular necrosis, peliosis hepatis, hepatic vein thrombosis, veno-occlusive disease, preeclampsia, eclampsia, acute fatty liver of pregnancy, intrahepatic cholestasis of pregnancy, and hepatic tumors including nodular hyperplasias, adenomas, and carcinomas; a cardiovascular disorder, such as arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation; an autoimmune/inflammatory disorder, such as acquired immunodeficiency syndrome (AIDS), Addison's disease, adult respiratory distress syndrome, allergies, ankylosing spondylitis, amyloidosis, anemia, asthma, atherosclerosis, atherosclerotic plaque rupture, autoimmune hemolytic anenia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, degradation of articular cartilage, osteoporosis, pancreatitis, polymyositis, psoriasis, Reiter's syndrome, rheumatoid arrhritis, scleroderma, Sjögren's syndrome, systemic anaphylaxis, systemic lupus erythematosus, systemic sclerosis, dirombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adendcarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a developmental disorder, such as renal tubular acidosis, anemia, Cushing's syndrome, achondroplastic dwarfism, Duchenne and Becker muscular dystrophy, bone resorption, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, age-related macular degeneration, and sensorineural hearing loss; an epithelial disorder, such as dyshidrotic eczema, allergic contact dermatitis, keratosis pilaris, melasma, vitiligo, actinic keratosis, basal cell carcinoma, squamous cell carcinoma, seborrheic keratosis, folliculitis, herpes simplex, herpes zoster, varicella, candidiasis, dermatophytosis, scabies, insect bites, cherry angioma, keloid, dermatofibroma, acrochordons, urticaria, transient acantholytic dermatosis, xerosis, eczema, atopic dermatitis, contact dermatitis, hand eczema, nummular eczema, lichen simplex chronicus, asteatotic eczema, stasis dermatitis and stasis ulceration, seborrheic dermatitis, psoriasis, lichen planus, pityriasis rosea, impetigo, ecthyma, dermatophytosis, tinea versicolor, warts, acne vulgaris, acne rosacea, pemphigus vulgaris, pemphigus foliaceus, paraneoplastic pemphigus, bulbous pemphigoid, herpes gestationis, dermatitis herpetiformis, linear IgA disease, epidermolysis bullosa acquisita, dermatomyositis, lupus erythematosus, scleroderma and morphea, erythroderma, alopecia, figurate skin lesions, telangiectasias, hypopigmentation, hyperpigmentation, vesicles/bullae, exanthems, cutaneous drug reactions, papulonodular skin lesions, chronic non-healing wounds, photosensitivity diseases, epidermolysis bullosa simplex, epidermolytic hyperkeratosis, epidermolytic and nonepidermolytic palmoplantar keratoderma, ichthyosis bullosa of Siemens, ichthyosis exfoliativa, keratosis palmaris et plantaris, keratosis palmoplantaris, palmoplantar keratoderma, keratosis punctata, Meesmann's corneal dystrophy, pachyonychia congenita, white sponge nevus, steatocystoma multiplex, epidermal nevi/epidermolytic hyperkeratosis type, monilethrix, trichothiodystrophy, chronic hepatitis/cryptogenic cirrhosis, and colorectal hyperplasia; a neurological disorder, such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; and a reproductive disorder, such as infertility, including tubal disease, ovulatory defects, and endometriosis, a disorder of prolactin production, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis; cancer of the breast, fibrocystic breast disease, and galactorrhea; a disruption of spermatogenesis, abnormal sperm physiology, cancer of the testis, cancer of the prostate, benign prostatic hyperplasia, prostatitis, Peyronie's disease, impotence, carcinoma of the male breast, and gynecomastia. The polynucleotide sequences encoding PRTS may be used in Southern or northern analysis, dot blot, or other membrane-based technologies; in PCR technologies; in dipstick, pin, and multiformat ELISA-like assays; and in microarrays utilizing fluids or tissues from patients to detect altered PRTS expression. Such qualitative or quantitative methods are well known in the art.

In a particular aspect, the nucleotide sequences encoding PRTS may be useful in assays that detect the presence of associated disorders, particularly those mentioned above. The nucleotide sequences encoding PRTS may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is signicantly altered in comparison to a control sample then the presence of altered levels of nucleotide sequences encoding PRTS in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of PRTS, a normal or standard profile for expression is established This may be accomplished by combining body fluids or cell extracts taken from normal subjects, either animal or human, with a sequence, or a fragment thereof, encoding PRTS, under conditions suitable for hybridization or amplification Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PRTS may involve the use of PCP. These oligomers may be chemically synthesized, generated enzymatically, or produced in vitro. Oligomers will preferably contain a fragment of a polynucleotide encoding PRTS, or a fragment of a polynucleotide complementary to the polynucleotide encoding PRTS, and will be employed under optimized conditions for identification of a specific gene or condition. Oligomers may also be employed under less stringent conditions for detection or quantification of closely related DNA or RNA sequences.

In a particular aspect, oligonucleotide primers derived from the polynucleotide sequences encoding PRTS may be used to detect single nucleotide polymorphisms (SNPs). SNPs are substitutions, insertions and deletions that are a frequent cause of inherited or acquired genetic disease in humans. Methods of SNP detection include, but are not limited to, single-stranded conformation polymorphism (SSCP) and fluorescent SSCP (fSSCP) methods. In SSCP, oligonucleotide primers derived from the polynucleotide sequences encoding PRTS are used to amplify DNA using the polymerase chain reaction (PCR). The DNA may be derived, for example, from diseased or normal tissue, biopsy samples, bodily fluids, and the like. SNPs in the DNA cause differences in the secondary and tertiary structures of PCR products in single-stranded form, and these differences are detectable using gel electrophoresis in non-denaturing gels. In fSCCP, the oligonucleotide primers are fluorescently labeled, which allows detection of the amplimers in high-throughput equipment such as DNA sequencing machines. Additionally, sequence database analysis methods, termed in silico SNP (isSNP), are capable of identifying polymorphisms by comparing the sequence of individual overlapping DNA fragments which assemble into a common consensus sequence. These computer-based methods filter out sequence variations due to laboratory preparation of DNA and sequencing errors using statistical models and automated analyses of DNA sequence chromatograms. In the alternative, SNPs may be detected and characterized by mass spectrometry using, for example, the high throughput MASSARRAY system (Sequenom, Inc., San Diego Calif.).

Methods which may also be used to quantify the expression of PRTS include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in a high-throughput format where the oligomer or polynucleotide of interest is presented in various dilutions and a spectrophotometric or colorimetric response gives rapid quantitation.

In further embodiments, oligonucleotides or longer fragments derived from any of the polynucleotide sequences described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

In another embodiment, PRTS, fragments of PRTS, or antibodies specific for PRTS may be used as elements on a microarray. The microarray may be used to monitor or measure protein-protein interactions, drug-target interactions, and gene expression profiles, as described above.

A particular embodiment relates to the use of the polynucleotides of the present invention to generate a transcript image of a tissue or cell type. A transcript image represents the global pattern of gene expression by a particular tissue or cell type. Global gene expression patterns are analyzed by quantifying the number of expressed genes and their relative abundance under given conditions and at a given time. (See Seilhamer et al, "Comparative Gene Transcript Analysis," U.S. Pat. No. 5,840,484, expressly incorporated by reference herein.) Thus a transcript image may be generated by hybridizing the polynucleotides of the present invention or their complements to the totality of transcripts or reverse transcripts of a particular tissue or cell type. In one embodiment, the hybridization takes place in high-throughput format, wherein the polynucleotides of the present invention or their complements comprise a subset of a plurality of elements on a microarray. The resultant transcript image would provide a profile of gene activity.

Transcript images may be generated using transcripts isolated from tissues, cell lines, biopsies, or other biological samples. The transcript image may thus reflect gene expression in vivo, as in the case of a tissue or biopsy sample, or in vitro, as in the case of a cell line.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir, E. F. et al. (1999) Mol. Carcinog. 24:153–159; Steiner, S. and N. L. Anderson (2000) Toxicol. Lett. 112–113:467–471, expressly incorporated by reference herein). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data. The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity. (See, for example, Press Release 00-02 from the National Institute of Environmental Health Sciences, released Feb. 29, 2000, available at http://www.niehs.nih.gov/oc/news/toxchip.htm.) Therefore, it is important and desirable in toxicological screening using toxicant signatures to include all expressed gene sequences.

In one embodiment, the toxicity of a test compound is assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

Another particular embodiment relates to the use of the polypeptide sequences of the present invention to analyze the proteome of a tissue or cell type. The term proteome refers to the global pattern of protein expression in a particular tissue or cell type. Each protein component of a proteome can be subjected individually to further analysis. Proteome expression patterns, or profiles, are analyzed by quantifying the number of expressed proteins and their relative abundance under given conditions and at a given time. A profile of a cell's proteome may thus be generated by separating and analyzing the polypeptides of a particular tissue or cell type. In one embodiment, the separation is achieved using two dimensional gel electrophoresis, in which proteins from a sample are separated by isoelectric focusing in the first dimension, and then according to molecular weight by sodium dodecyl sulfate slab gel electrophoresis in the second dimension (Steiner and Anderson, supra). The proteins are visualized in the gel as discrete and uniquely positioned spots, typically by staining the gel with an agent such as Coomassie Blue or silver or fluorescent stains. The optical density of each protein spot is generally proportional to the level of the protein in the sample. The optical densities of equivalently positioned protein spots from different samples, for example, from biological samples either treated or untreated with a test compound or therapeutic agent, are compared to identify any changes in protein spot density related to the treatment. The proteins in the spots are partially sequenced using, for example, standard methods employing chemical or enzymatic cleavage followed by mass spectrometry. The identity of the protein in a spot may be determined by comparing its partial sequence, preferably of at least 5 contiguous amino acid residues, to the polypeptide sequences of the present invention. In some cases, further sequence data may be obtained for definitive protein identification.

A proteomic profile may also be generated using antibodies specific for PRTS to quantify the levels of PRTS expression. In one embodiment, the antibodies are used as elements on a microarray, and protein expression levels are quantified by exposing the microarray to the sample and detecting the levels of protein bound to each array element (Lueking, A. et al. (1999) Anal. Biochem. 270:103–111; Mendoze, L. G. et al. (1999) Biotechniques 27:778–788). Detection may be performed by a variety of methods known in the art, for example, by reacting the proteins in the sample with a thiol- or amino-reactive fluorescent compound and detecting the amount of fluorescence bound at each array element.

Toxicant signatures at the proteome level are also useful for toxicological screening, and should be analyzed in parallel with toxicant signatures at the transcript level. There is a poor correlation between transcript and protein abundances for some proteins in some tissues (Anderson, N. L. and J. Seilhamer (1997) Electrophoresis 18:533–537), so proteome toxicant signatures may be useful in the analysis of compounds which do not significantly affect the transcript image, but which alter the proteomic profile. In addition, the analysis of transcripts in body fluids is difficult, due to rapid degradation of mRNA, so proteomic profiling may be more reliable and informative in such cases.

In another embodiment, the toxicity of a test compound is assessed by treating a biological sample containing proteins with the test compound. Proteins that are expressed in the treated biological sample are separated so that the amount of each protein can be quantified. The amount of each protein is compared to the amount of the corresponding protein in an untreated biological sample. A difference in the amount of protein between the two samples is indicative of a toxic response to the test compound in the treated sample. Individual proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies specific to the polypeptides of the present invention. The amount of protein recognized by the antibodies is quantified. The amount of protein in the treated biological sample is compared with the amount in an untreated biological sample. A difference in the amount of protein between the two samples is indicative of a toxic response to the test compound in the treated sample.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. USA 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. USA 94:2150–2155; and Heller, M. J. et al. (1997) U.S. Pat. No. 5,605,662.) Various types of microarrays are well known and thoroughly described in *DNA Microarrays: A Practical Aproach*, M. Schena, ed. (1999) Oxford University Press, London, hereby expressly incorporated by reference.

In another embodiment of the invention, nucleic acid sequences encoding PRTS may be used to generate hybridization probes useful in mapping the naturally occurring genomic sequence. Either coding or noncoding sequences may be used, and in some instances, noncoding sequences may be preferable over coding sequences. For example, conservation of a coding sequence among members of a multi-gene family may potentially cause undesired cross hybridization during chromosomal mapping. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat. Genet. 15:345–355; Price, C. M. (1993) Blood Rev. 7:127–134; and Trask, B. J. (1991) Trends Genet. 7:149–154.) Once mapped, the nucleic acid sequences of the invention may be used to develop genetic linkage maps, for example, which correlate the inheritance of a disease state with the inheritance of a particular chromosome region or restriction fragment length polymorphism (RFLP). (See, for example, Lander, E. S. and D. Botstein (1986) Proc. Natl. Acad. Sci. USA 83:7353–7357.)

Fluorescent in situ hybridization (FISH) may be correlated with other physical and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) World Wide Web site. Correlation between the location of the gene encoding PRTS on a physical map and a specific disorder, or a predisposition to a specific disorder, may help define the region of DNA associated with that disorder and thus may further positional cloning efforts.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the exact chromosomal locus is not known. This information is valuable to investigators searching for disease genes using positional cloning or other gene discovery techniques. Once the gene or genes responsible for a disease or syndrome have been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577–580.) The nucleotide sequence of the instant invention may also be used to detect differences in the chromosomal location due to translocation, inversion, etc., among normal, carrier, or affected individuals.

In another embodiment of the invention, PRTS, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between PRTS and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with PRTS, or fragments thereof, and washed. Bound PRTS is then detected by methods well known in the art. Purified PRTS can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PRTS specifically compete with a test compound for binding PRTS. In this manner, antibodies can be used to detect the presence of any peptide which shares one or more antigenic determinants with PRTS.

In additional embodiments, the nucleotide sequences which encode PRTS may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following embodiments are, therefore, to be construed as merely illustrative, and not limitative of the remainder of the disclosure in any way whatsoever.

The disclosures of all patents, applications, and publications mentioned above and below, including U.S. Ser. No. 60/231,039, U.S. Ser. No. 60/232,812, U.S. Ser. No. 60/234,850, U.S. Ser. No. 60/236,500, U.S. Ser. No. 60/238,773, and U.S. Ser. No. 60/239,658, are hereby expressly incorporated by reference.

EXAMPLES

I. Construction of cDNA Libraries

Incyte cDNAs were derived from cDNA libraries described in the LIFESEQ GOLD database (Incyte Genomics, Palo Alto Calif.) and shown in Table 4, column 5. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A)+ RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the at (See, e.g., Ausubel, 1997, supra, units 5.1–6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), PCDNA2.1 plasmid (invitrogen, Carlsbad Calif.), PBK-CMV plasmid (Stratagene), PCR2-TOPOTA (Invitrogen), PCMV-ICIS (Stratagene), or pINCY (Incyte Genomics, Palo Alto Calif.), or derivatives thereof. Recombinant plasmids were transformed into competent *E. coli* cells including XL1-Blue, XL1-BlueMRF, or SOLR from Stratagene or DH5α, DH10B, or ElectroMAX DH10B from Life Technologies.

II. Isolation of cDNA Clones

Plasmids obtained as described in Example I were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWEIL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a FLUOROSKAN II fluorescence scanner (Labsystems Oy, Helsinki, Finland).

III. Sequencing and Analysis

Incyte cDNA recovered in plasmids as described in Example II were sequenced as follows. Sequencing reactions were processed using standard methods or high-throughput instrumentation such as the ABI CATALYST 800 (Applied Biosystems) thermal cycler or the PTC-200 thermal cycler (MJ Research) in conjunction with the HYDRA microdispenser (Robbins Scientific) or the MICROLAB 2200 Hamilton) liquid transfer system. cDNA sequencing reactions were prepared using reagents provided by Amersham Pharmacia Biotech or supplied in ABI sequencing kits such as the ABI PRISM BIGDYE Terminator cycle sequencing ready reaction kit (Applied Biosystems). Electrophoretic separation of cDNA sequencing reactions and detection of labeled polynucleotides were carried out using the MEGABACE 1000 DNA sequencing system (Molecular Dynamics); the ABI PRISM 373 or 377 sequencing system (Applied Biosystems) in conjunction with standard ABI protocols and base calling software; or other sequence analysis systems known in the art. Reading frames within the cDNA sequences were identified using standard methods (reviewed in Ausubel, 1997, supra, unit 7.7). Some of the cDNA sequences were selected for extension using the techniques disclosed in Example VIII.

The polynucleotide sequences derived from Incyte cDNAs were validated by removing vector, linker, and poly(A) sequences and by masking ambiguous bases, using algorithms and programs based on BLAST, dynamic programming, and dinucleotide nearest neighbor analysis. The Incyte cDNA sequences or translations thereof were then queried against a selection of public databases such as the GenBank primate, rodent, mammalian, vertebrate, and eukaryote databases, and BLOCKS, PRINTS, DOMO, PRODOM, and hidden Markov model (HMM)-based protein family databases such as PFAM. (HMM is a probabilistic approach which analyzes consensus primary structures of gene families. See, for example, Eddy, S. R. (1996) Curr. Opin. Struct. Biol. 6:361–365.) The queries were performed using programs based on BLAST, FASTA, BLIMPS, and HMMER. The Incyte cDNA sequences were assembled to produce full length polynucleotide sequences. Alternatively, GenBank cDNAs, GenBank ESTs, stitched sequences, stretched sequences, or Genscan-predicted coding sequences (see Examples IV and V) were used to extend Incyte cDNA assemblages to full length. Assembly was performed using programs based on Phred, Phrap, and Consed, and cDNA assemblages were screened for open reading frames using programs based on GeneMark, BLAST, and FASTA. The full length polynucleotide sequences were translated to derive the corresponding fall length polypeptide sequences. Alternatively, a polypeptide of the invention may begin at any of the methionine residues of the full length translated polypeptide. Full length polypeptide sequences were subsequently analyzed by querying against databases such as the GenBank protein databases (genpept), SwissProt, BLOCKS, PRINTS, DOMO, PRODOM, Prosite, and hidden Markov model (HMM)-based protein family databases such as PFAM. Full length polynucleotide sequences are also analyzed using MACDNASIS PRO software (Hitachi Software Engineering, South San Francisco Calif.) and LASERGENE software (DNASTAR). Polynucleotide and polypeptide sequence alignments are generated using default parameters specified by the CLUSTAL algorithm as incorporated into the MEGALIGN multisequence alignment program (DNASTAR), which also calculates the percent identity between aligned sequences.

Table 7 summarizes the tools, programs, and algorithms used for the analysis and assembly of Incyte cDNA and full length sequences and provides applicable descriptions, references, and threshold parameters. The first column of Table 7 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score or the lower the probability value, the greater the identity between two sequences).

The programs described above for the assembly and analysis of full length polynucleotide and polypeptide sequences were also used to identify polynucleotide sequence fragments from SEQ ID NO:18–34. Fragments from about 20 to about 4000 nucleotides which are useful in hybridization and amplification technologies are described in Table 4, column 4.

IV. Identification and Editing of Coding Sequences from Genomic DNA

Putative proteases were initially identified by running the Genscan gene identification program against public genomic sequence databases (e.g., gbpri and gbhtg). Genscan is a general-purpose gene identification program which analyzes genomic DNA sequences from a variety of organisms (See Burge, C. and S. Karlin (1997) J. Mol. Biol. 268:78–94, and Burge, C. and S. Karlin (1998) Curr. Opin. Struct. Biol. 8:346–354). The program concatenates predicted exons to form an assembled cDNA sequence extending from a methionine to a stop codon The output of Genscan is a FASTA database of polynucleotide and polypeptide sequences. The maximum range of sequence for Genscan to analyze at once was set to 30 kb. To determine which of these Genscan predicted cDNA sequences encode proteases, the encoded polypeptides were analyzed by querying against PFAM models for proteases. Potential proteases were also identified by homology to Incyte cDNA sequences that had been annotated as proteases. These selected Genscan-predicted sequences were then compared by BLAST analysis to the genpept and gbpri public databases. Where necessary, the Genscan-predicted sequences were then edited by comparison to the top BLAST hit from genpept to correct errors in the sequence predicted by Genscan, such as extra or omitted exons. BLAST analysis was also used to find any Incyte cDNA or public cDNA coverage of the Genscan-predicted sequences, thus providing evidence for transcription. When Incyte cDNA coverage was available, this information was used to correct or confirm the Genscan predicted sequence. Full length polynucleotide sequences were obtained by assembling Genscan-predicted coding sequences with Incyte cDNA sequences and/or public cDNA sequences using the assembly process described in Example III. Alternatively, full length polynucleotide sequences were derived entirely from edited or unedited Genscan-predicted coding sequences.

V. Assembly of Genomic Sequence Data with CDNA Sequence Data

"Stitched" Sequences

Partial cDNA sequences were extended with exons predicted by the Genscan gene identification program described in Example IV. Partial cDNAs assembled as described in Example III were mapped to genomic DNA and parsed into clusters containing related cDNAs and Genscan exon predictions from one or more genomic sequences. Each cluster was analyzed using an algorithm based on graph theory and dynamic programming to integrate cDNA and genomic information, generating possible splice variants that were subsequently confirmed, edited, or extended to create a full length sequence. Sequence intervals in which the entire length of the interval was present on more than one sequence in the cluster were identified, and intervals thus identified were considered to be equivalent by transitivity. For example, if an interval was present on a cDNA and two genomic sequences, then al three intervals were considered to be equivalent This process allows unrelated but consecutive genomic sequences to be brought together, bridged by cDNA sequence. Intervals thus identified were then "stitched" together by the stitching algorithm in the order that they appear along their parent sequences to generate the longest possible sequence, as well as sequence variants. Linkages between intervals which proceed along one type of parent sequence (cDNA to cDNA or genomic sequence to genomic sequence) were given preference over linkages which change parent type (cDNA to genomic sequence). The resultant stitched sequences were translated and compared by BLAST analysis to the genpept and gbpri public databases. Incorrect exons predicted by Genscan were corrected by comparison to the top BLAST hit from genpept Sequences were further extended with additional cDNA sequences, or by inspection of genomic DNA, when necessary.

"Stretched" Sequences

Partial DNA sequences were extended to full length with an algorithm based on BLAST analysis. First, partial cDNAs assembled as described in Example III were queried against public databases such as the GenBank primate, rodent, mammalian, vertebrate, and eukaryote databases using the BLAST program. The nearest GenBank protein homolog was then compared by BLAST analysis to either Incyte cDNA sequences or GenScan exon predicted sequences described in Example IV. A chimeric protein was generated by using the resultant high-scoring segment pairs (HSPs) to map the translated sequences onto the GenBank protein homolog. Insertions or deletions may occur in the chimeric protein with respect to the original GenBank protein homolog. The GenBank protein homolog, the chimeric protein, or both were used as probes to search for homologous genomic sequences from the public human genome databases. Partial DNA sequences were therefore "stretched" or extended by the addition of homologous genomic sequences. The resultant stretched sequences were examined to determine whether it contained a complete gene.

VI. Chromosomal Mapping of PRTS Encoding Polynucleotides

The sequences which were used to assemble SEQ ID NO:18–34 were compared with sequences from the Incyte LIFESEQ database and public domain databases using BLAST and other implementations of the Smith-Waterman algorithm Sequences from these databases that matched SEQ ID NO:18–34 were assembled into clusters of contiguous and overlapping sequences using assembly algorithms such as Phrap (Table 7). Radiation hybrid and genetic mapping data available from public resources such as the Stanford Human Genome Center (SHGC), Whitehead Institute for Genome Research (WIGR), and Généthon were used to determine if any of the clustered sequences had been previously mapped. Inclusion of a mapped sequence in a cluster resulted in the assignment of all sequences of that cluster, including its particular SEQ ID NO:, to that map location.

Map locations are represented by ranges, or intervals, of human chromosomes. The map position of an interval, in centiMorgans, is measured relative to the terminus of the chromosome's p-arm. (The centiMorgan (cM) is a unit of measurement based on recombination frequencies between chromosomal markers. On average, 1 cM is roughly equivalent to 1 megabase (Mb) of DNA in humans, although this can vary widely due to hot and cold spots of recombination.) The cM distances are based on genetic markers mapped by Généthon which provide boundaries for radiation hybrid markers whose sequences were included in each of the clusters. Human genome maps and other resources available to the public, such as the NCBI "GeneMap'99" World Wide Web site (http://www.ncbi.nlm.nih.gov/genemap/), can be employed to determine if previously identified disease genes map within or in proximity to the intervals indicated above.

In this manner, SEQ ID NO:18 was mapped to chromosome 16 within the interval from 33.4 to 42.7 centiMorgans. In this manner, SEQ ID NO:22 was mapped to chromosome 1 within the interval from 219.2 to 222.7 centiMorgans.

VII. Analysis of Polynucleotide Expression

Northern analysis is a laboratory technique used to detect the presence of a transcript of a gene and involves the hybridization of a labeled nucleotide sequence to a membrane on which RNAs from a particular cell type or tissue have been bound (See, e.g., Sambrook, supra, ch. 7; Ausubel (1995) supra, ch. 4 and 16.)

Analogous computer techniques applying BLAST were used to search for identical or related molecules in cDNA databases such as GenBank or LIFESEQ (Incyte Genomics). This analysis is much faster than multiple membrane-based hybridizations. In addition, the sensitivity of the computer search can be modified to determine whether any particular match is categorized as exact or similar. The basis of the search is the product score, which is defined as:

$$\frac{\text{BLAST Score} \times \text{Percent Identity}}{5 \times \text{minimum}\{\text{length (Seq. 1), length (Seq. 2)}\}}$$

The product score takes into account both the degree of similarity between two sequences and the length of the sequence match The product score is a normalized value between 0 and 100, and is calculated as follows: the BLAST score is multiplied by the percent nucleotide identity and the product is divided by (5 times the length of the shorter of the two sequences). The BLAST score is calculated by assigning a score of +5 for every base that matches in a high-scoring segment pair (HSP), and −4 for every mismatch. Two sequences may share more than one HSP (separated by gaps). If ere is more than one HSP, then the pair with the highest BLAST score is used to calculate the product score. The product score represents a balance between fractional overlap and quality in a BLAST alignment. For example, a product score of 100 is produced only for 100% identity over the entire length of the shorter of the two sequences being compared. A product score of 70 is produced either by 100% identity and 70% overlap at one end, or by 88% identity and 100% overlap at the other. A product score of 50 is produced either by 100% identity and 50% overlap at one end, or 79% identity and 100% overlap.

Alternatively, polynucleotide sequences encoding PRTS are analyzed with respect to the tissue sources from which they were derived. For example, some full length sequences are assembled, at least in part, with overlapping Incyte cDNA sequences (see Example III). Each cDNA sequence is derived from a cDNA library constructed from a human tissue. Each human tissue is classified into one of the following organ/tissue categories: cardiovascular system; connective tissue; digestive system; embryonic structures; endocrine system; exocrine glands; genitalia, female; genitalia, male; germ cells; hemic and immune system; liver; musculoskeletal system; nervous system; pancreas; respiratory system; sense organs; skin; stomatognathic system; unclassified/mixed; or urinary tract. The number of libraries in each category is counted and divided by the total number of libraries across all categories. Similarly, each human tissue is classified into one of the following disease/condition categories: cancer, cell line, developmental, inflammation, neurological, trauma, cardiovascular, pooled, and other, and the number of libraries in each category is counted and divided by the total number of libraries across all categories. The resulting percentages reflect the tissue- and disease-specific expression of cDNA encoding PRTS. cDNA sequences and cDNA library/tissue information are found in the LIFESEQ GOLD database (Incyte Genomics, Palo Alto Calif.).

VIII. Extension of PRTS Encoding Polynucleotides

Full length polynucleotide sequences were also produced by extension of an appropriate fragment of the full length molecule using oligonucleotide primers designed from this fragment. One primer was synthesized to initiate 5' extension of the known fragment, and the other primer was synthesized to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and 2-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 µl PICOGREEN quantitation reagent (0.25% (v/v) PICOGREEN; Molecular Probes, Eugene Oreg.) dissolved in 1×TE and 0.5 µl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antbiotic-containing media, and individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulfoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Applied Biosystems).

In like manner, full length polynucleotide sequences are verified using the above procedure or are used to obtain 5' regulatory sequences using the above procedure along with oligonucleotides designed for such extension, and an appropriate genomic library.

IX. Labeling and Use of Individual Hybridization Probes

Hybridization probes derived from SEQ ID NO:18–34 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 $\mu$Ci of [$\gamma$-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to nylon membranes (Nytran Plus, Schleicher & Schuell Durham N.H). Hybridization is carried out for 16 hours at 40° C. To remove nonspecific signals, blots are sequentially washed at room temperature under conditions of up to, for example, 0.1× saline sodium citrate and 0.5% sodium dodecyl sulfate. Hybridization patterns are visualized using autoradiography or an alternative imaging means and compared.

X. Microarrays

The linkage or synthesis of array elements upon a microarray can be achieved utilizing photolithography, piezoelectric printing (ink-jet printing, See, e.g., Baldeschweiler, supra), mechanical microspotting technologies, and derivatives thereof. The substrate in each of the aforementioned technologies should be uniform and solid with a non-porous surface (Schena (1999), supra). Suggested substrates include silicon, silica, glass slides, glass chips, and silicon wafers. Alternatively, a procedure analogous to a dot or slot blot may also be used to arrange and link elements to the surface of a substrate using thermal, UV, chemical, or mechanical bonding procedures. A typical array may be produced using available methods and machines well known to those of ordinary skill in the art and may contain any appropriate number of elements. (See, e.g., Schena. M. et al. (1995) Science 270:467–470; Shalon, D. et al. (1996) Genome Res. 6:639–645; Marshall, A. and J. Hodgson (1998) Nat. Biotechnol. 16:27–31.)

Full length cDNAs, Expressed Sequence Tags (ESTs), or fragments or oligomers thereof may comprise the elements of the microarray. Fragments or oligomers suitable for hybridization can be selected using software well known in the art such as LASERGENE software (DNASTAR). The array elements are hybridized with polynucleotides in a biological sample. The polynucleotides in the biological sample are conjugated to a fluorescent label or other molecular tag for ease of detection. After hybridization, nonhybridized nucleotides from the biological sample are removed, and a fluorescence scanner is used to detect hybridization at each array element. Alternatively, laser desorption and mass spectrometry may be used for detection of hybridization. The degree of complementarity and the relative abundance of each polynucleotide which hybridizes to an element on the microarray may be assessed. In one embodiment, microarray preparation and usage is described in detail below.

Tissue or Cell Sample Preparation

Total RNA is isolated from tissue samples using the guanidinium thiocyanate method and poly(A)$^+$ RNA is purified using the oligo-(dT) cellulose method. Each poly (A)$^+$ RNA sample is reverse transcribed using MMLV reverse-transcriptase, 0.05 pg/$\mu$l oligo-(dT) primer (21mer), 1× first strand buffer, 0.03 units/$\mu$l RNase inhibitor, 500 $\mu$M dATP, 500 $\mu$M dGTP, 500 $\mu$M dTTP, 40 $\mu$M dCTP, 40 $\mu$M dCTP-Cy3 (BDS) or dCTP-Cy5 (Amersham Pharmacia Biotech). The reverse transcription reaction is performed in a 25 ml volume containing 200 ng poly(A)$^+$ RNA with GEMBRIGHT kits (Incyte). Specific control poly(A)$^+$ RNAs are synthesized by in vitro transcription from non-coding yeast genomic DNA. After incubation at 37° C. for 2 hr, each reaction sample (one with Cy3 and another with Cy5 labeling) is treated with 2.5 ml of 0.5M sodium hydroxide and incubated for 20 minutes at 85° C. to the stop the reaction and degrade the RNA. Samples are purified using two successive CHROMA SPIN 30 gel filtration spin columns (CLONTECH Laboratories, Inc. (CLONTECH), Palo Alto Calif.) and after combining, both reaction samples are ethanol precipitated using 1 ml of glycogen (1 mg/ml), 60 ml sodium acetate, and 300 ml of 100% ethanol. The sample is then dried to completion using a SpeedVAC (Savant Instruments Inc., Holbrook N.Y.) and resuspended in 14 $\mu$l 5×SSC/ 0.2% SDS.

Microarray Preparation

Sequences of the present invention are used to generate array elements. Each array element is amplified from bacterial cells containing vectors with cloned cDNA inserts. PCR amplification uses primers complementary to the vector sequences flaking the cDNA insert. Array elements are amplified in thirty cycles of PCR from an initial quantity of 1–2 ng to a final quantity greater than 5 $\mu$g. Amplified array elements are then purified using SEPHACRYL-400 (Amersham Pharmacia Biotech).

Purified array elements are inmmobilized on polymer-coated glass slides. Glass microscope slides (Corning) are cleaned by ultrasound in 0.1% SDS and acetone, with extensive distilled water washes between and after treatments. Glass slides are etched in 4% hydrofluoric acid (VWR Scientific Products Corporation (VWR), West Chester Pa.), washed extensively in distilled water, and coated with 0.05% aminopropyl silane (Sigma) in 95% ethanol. Coated slides are cured in a 110° C. oven.

Array elements are applied to the coated glass substrate using a procedure described in U.S. Pat. No. 5,807,522, incorporated herein by reference. 1 $\mu$l of the array element DNA, at an average concentration of 100 ng/$\mu$l, is loaded into the open capillary printing element by a high-speed robotic apparatus. The apparatus then deposits about 5 nl of array element sample per slide.

Microarrays are UV-crosslinked using a STRATALINKER UV-crosslinker (Stratagene). Microarrays are washed at room temperature once in 0.2% SDS and three times in distilled water. Non-specific binding sites are blocked by incubation of microarrays in 0.2% casein in phosphate buffered saline (PBS) (Tropix, Inc., Bedford Mass.) for 30 minutes at 60° C. followed by washes in 0.2% SDS and distilled water as before.

Hybridization

Hybridization reactions contain 9 $\mu$l of sample mixture consisting of 0.2 $\mu$g each of Cy3 and Cy5 labeled cDNA synthesis products in 5×SSC, 0.2% SDS hybridization buffer. The sample mixture is heated to 65° C. for 5 minutes and is aliquoted onto the microarray surface and covered with an 1.8 cm$^2$ coverslip. The arrays are transferred to a waterproof chamber having a cavity just slightly larger than a microscope slide. The chamber is kept at 100% humidity internally by the addition of 140 $\mu$l of 5×SSC in a corner of the chamber. The chamber containing the arrays is incubated for about 6.5 hours at 60° C. The arrays are washed for 10 min at 45° C. in a first wash buffer (0.1×SSC, 0.1% SDS), three times for 10 minutes each at 45° C. in a second wash buffer (0.1×SSC), and dried.

Detection

Reporter-labeled hybridization complexes are detected with a microscope equipped with an Innova 70 mixed gas 10 W laser (Coherent, Inc., Santa Clara Calif.) capable of generating spectral lines at 488 nm for excitation of Cy3 and at 632 nm for excitation of Cy5. The excitation laser light is focused on the array using a 20× microscope objective (Nikon, Inc., Melville N.Y.). The slide containing the array is placed on a computer-controlled X-Y stage on the microscope and raster-scanned past the objective. The 1.8 cm×1.8 cm array used in the present example is scanned with a resolution of 20 micrometers.

In two separate scans, a mixed gas multiline laser excites the two fluorophores sequentially. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. Each array is typically scanned twice, one scan per fluorophore using the appropriate filters at the laser source, although the apparatus is capable of recording the spectra from both fluorophores simultaneously:

The sensitivity of the scans is typically calibrated using the signal intensity generated by a cDNA control species added to the sample mixture at a known concentration. A specific location on the array contains a complementary DNA sequence, allowing the intensity of the signal at that location to be correlated with a weight ratio of hybridizing species of 1:100,000. When two samples from different sources (e.g., representing test and control cells), each labeled with a different fluorophore, are hybridized to a single array for the purpose of identifying genes that are differentially expressed, the calibration is done by labeling samples of the calibrating cDNA with the two fluorophores and adding identical amounts of each to the hybridization mixture.

The output of the photomultiplier tube is digitized using a 12-bit RTI-835H analog-to-digital (A/D) conversion board (Analog Devices, Inc., Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum.

A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS gene expression analysis program (Incyte).

XI. Complementary Polynucleotides

Sequences complementary to the PRTS-encoding sequences, or any parts thereof, are used to detect, decrease, or inhibit expression of naturally occurring PRTS. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of PRTS. To inhibit transcription, a complementary oligonucleotide is designed from the most unique 5' sequence and used to prevent promoter binding to the coding sequence. To inhibit translation, a complementary oligonucleotide is designed to prevent ribosomal binding to the PRTS-encoding transcript.

XII. Expression of PRTS

Expression and purification of PRTS is achieved using bacterial or virus-based expression systems. For expression of PRTS in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element Recombinant vectors are transformed into suitable bacterial hosts, e.g., BL21(DE3). Antibiotic resistant bacteria express PRTS upon induction with isopropyl beta-D-thiogalactopyranoside (IPTG). Expression of PRTS in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding PRTS by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K et al. (1994) Proc. Natl. Acad. Sci. USA 91:3224–3227; Sandig, V. et al. (1996) Hum. Gene Ther. 7:1937–1945.)

In most expression systems, PRTS is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from PRTS at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch. 10 and 16). Purified PRTS obtained by these methods can be used directly in the assays shown in Examples XVI, XVII, XVIII, and XIX where applicable.

XIII. Functional Assays

PRTS function is assessed by expressing the sequences encoding PRTS at physiologically elevated levels in mammalian cell culture systems. cDNA is subcloned into a mammalian expression vector containing a strong promoter that drives high levels of cDNA expression. Vectors of choice include PCMV SPORT (Life Technologies) and PCR3.1 (Invitrogen, Carlsbad Calif.), both of which contain the cyt megalovirus promoter. 5–10 $\mu$g of recombinant vector are transiently trasfected into a human cell line, for example, an endothelial or hematopoietic cell line, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxynridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of PRTS on gene expression can be assessed using highly purified populations of cells transfected with sequences encoding PRTS and either CD64 or CD64-GFP. CD64 and CD64-GEP are expressed on the surface of transfected cells and bind to conserved regions of human immunoglobulin G (IgG). Transfected cells are efficiently-separated from nontransfected cells using magnetic beads coated with either human IgG or antibody against CD64 (DYNAL, Lake Success N.Y.). mRNA can be purified from the cells using methods well known by those of skill in the art. Expression of mRNA encoding PRTS and other genes of interest can be analyzed by northern analysis or microarray techniques.

XIV. Production of PRTS Specific Antibodies

PRTS substantially purified using polyacrylamide gel electrophoresis (PAGE; see, e.g., Harrington, M. G. (1990) Methods Enzymol. 182:488–495), or other purification techniques, is used to immnunize rabbits and to produce antibodies using standard protocols.

Alternatively, the PRTS amino acid sequence is analyzed using LASERGENE software (DNASTAR) to determine regions of high immunogenicity, and a corresponding oligopeptide is synthesized and used to raise antibodies by means kmown to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides of about 15 residues in length are synthesized using an ABI 431A peptide synthesizer (Applied Biosystems) using FMOC chemistry and coupled to OM (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant Resulting antisera are tested for antipeptide and anti-PRTS activity by, for example, binding the peptide or PRTS to a substrate, blocking with 1% BSA, reacting with rabbit antisera, washing, and reacting with radio-iodinated goat anti-rabbit IgG.

XV. Purification of Naturally Occurring PRTS Using Specific Antibodies

Naturally occurring or recombinant PRTS is substantially purified by immuno-affinity chromatography using antibodies specific for PRTS. An immunoaffinity column is constructed by covalently coupling anti-PRTS antibody to an activated chromatographic resin, such as CNBr-activated SEPHAROSE (Amersham Pharmacia Biotech). After the coupling, the resin is blocked and washed according to the manufacturer's instructions.

Media containing PRTS are passed over the immunoaffinity column, and the column is washed under conditions that allow the preferential absorbance of PRTS (e.g., high ionic strength buffers in the presence of detergent). The column is eluted under conditions that disrupt antibody/PRTS binding (e.g., a buffer of pH 2 to pH 3, or a high concentration of a chaotrope, such as urea or thiocyanate ion), and PRTS is collected.

XVI. Identification of Molecules Which Interact with PRTS

PRTS, or biologically active fragments thereof, are labeled with $^{125}$I Bolton-Hunter reagent. (See, e.g., Bolton A. E. and W. M. Hunter (1973) Biochem. J. 133:529–539.) Candidate molecules previously arrayed in the wells of a multi-well plate are incubated with the labeled PRTS, washed, and any wells with labeled PRTS complex are assayed. Data obtained using different concentrations of PRTS are used to calculate values for the number, affinity, and association of PRTS with the candidate molecules.

Alternatively, molecules interacting with PRTS are analyzed using the yeast two-hybrid system as described in Fields, S. and O. Song (1989) Nature 340:245–246, or using commercially available kits based on the two-hybrid system, such as the MATCHMAKER system (Clontech).

PRTS may also be used in the PATHCALLING process (CuraGen Corp., New Haven Conn.) which employs the yeast two-hybrid system in a high-throughput manner to determine all interactions between the proteins encoded by two large libraries of genes (Nandabalan, K. et al. (2000) U.S. Pat. No. 6,057,101).

XVII. Demonstration of PRTS Activity

Protease activity is measured by the hydrolysis of appropriate synthetic peptide substrates conjugated with various chromogenic molecules in which the degree of hydrolysis is quantified by spectrophotometric (or fluorometric) absorption of the released chromophore (Beynon, R. J. and J. S. Bond (1994) *Proteolytic Enzymes: A Practical Approach*, Oxford University Press, New York N.Y., pp. 25–55). Peptide substrates are designed according to the category of protease activity as endopeptidase (serine, cysteine, aspartic proteases, or metalloproteases), aminopeptidase (leucine aminopeptidase), or carboxypeptidase (carboxeypeptidases A and B, procollagen C-proteinase). Commonly used chromogens are 2-naphthylamine, 4-nitroaniline, and furylacrylic acid. Assays are performed at ambient temperature and contain an aliquot of the enzyme and the appropriate substrate in a suitable buffer. Reactions are carried out in an optical cuvette, and the increase/decrease in absorbance of the chromogen released during hydrolysis of the peptide substrate is measured. The change in absorbance is proportional to the enzyme activity in the assay.

An alternate assay for ubiquitin hydrolase activity measures the hydrolysis of a ubiquitin precursor. The assay is performed at ambient temperature and contains an aliquot of PRTS and the appropriate substrate in a suitable buffer. Chemically synthesized human ubiquitin-valine may be used as substrate. Cleavage of the C-terminal valine residue from the substrate is monitored by capillary electrophoresis (Franklin, K. et al. (1997) Anal. Biochem. 247:305–309).

In the alternative, an assay for protease activity takes advantage of fluorescence resonance energy transfer (FRET) that occurs when one donor and one acceptor fluorophore with an appropriate spectral overlap are in close proximity. A flexible peptide linker containing a cleavage site specific for PRTS is fused between a red-shifted variant (RSGFP4) and a blue variant (BFP5) of Green Fluorescent Protein. This fusion protein has spectral properties that suggest energy transfer is occurring from BFP5 to RSGFP4. When the fusion protein is incubated with PRTS, the substrate is cleaved, and the two fluorescent proteins dissociate. This is accompanied by a marked decrease in energy transfer which is quantified by comparing the emission spectra before and after the addition of PRTS (Mitra, R. D. et al. (1996) Gene 173:13–17). This assay can also be performed in living cells. In this case the fluorescent substrate protein is expressed constructively in cells and PRTS is introduced on an inducible vector so that FRET can be monitored in the presence and absence of PRTS (Sagot, I. et al. (1999) FEBS Lett. 447:53–57).

XVIII. Identification of PRTS Substrates

Phage display libraries can be used to identify optimal substrate sequences for PRTS. A random hexamer followed by a linker and a known antibody epitope is cloned as an N-terminal extension of gene III in a filamentous phage library. Gene III codes for a coat protein, and the epitope will be displayed on the surface of each phage particle. The library is incubated with PRTS under proteolytic conditions so that the epitope will be removed if the hexamer codes for a PRTS cleavage site. An antibody that recognizes the epitope is added along with immobilized protein A. Uncleaved phage, which still bear the epitope, are removed by centrifligation. Phage in the supernatant are then amplified and undergo several more rounds of screening. Individual phage clones are then isolated and sequenced. Reaction kinetics for these peptide substrates can be studied using an assay in Example XVII, and an optimal cleavage sequence can be derived (Ke, S. H. et al. (1997) J. Biol. Chem. 272:16603–16609).

To screen for in vivo PRTS substrates, this method can be expanded to screen a cDNA expression library displayed on the surface of phage particles (T7SELECT 10-3 Phage display vector, Novagen, Madison Wis.) or yeast cells (pYD1 yeast display vector kit, Invitrogen, Carlsbad Calif.). In this case, entire cDNAs are fused between Gene III and the appropriate epitope.

XIX. Identification of PRTS Inhibitors

Compounds to be tested are arrayed in the wells of a multi-well plate in varying concentrations along with an appropriate buffer and substrate, as described in the assays in Example XVII. PRTS activity is measured for each well and the ability of each compound to inhibit PRTS activity can be determined, as well as the dose-response kinetics. This assay could also be used to identify molecules which enhance PRTS activity.

In the alternative, phage display libraries can be used to screen for peptide PRTS inhibitors. Candidates are found among peptides which bind tightly to a protease. In this case, multi-well plate wells are coated with PRTS and incubated with a random peptide phage display library or a cyclic peptide library (Koivunen, E. et al. (1999) Nat. Biotechnol. 17:768–774). Unbound phage are washed away and selected phage amplified and rescreened for several more rounds. Candidates are tested for PRTS inhibitory activity using an assay described in Example XVI.

Various modifications and variations of the described methods and systems of the invention will be apparent to those skilled in the art without departing from the scope and spirit of the invention. Although the invention has been described in connection with certain embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Incyte Project ID | Incyte Polypeptide SEQ ID NO: | Incyte Polypeptide ID | Polynucleotide SEQ ID NO: | Incyte Polynucleotide ID |
|---|---|---|---|---|
| 6930294 | 1 | 6930294CD1 | 18 | 6930294CB1 |
| 7473018 | 2 | 7473018CD1 | 19 | 7473018CB1 |
| 7479221 | 3 | 7479221CD1 | 20 | 7479221CB1 |
| 2923874 | 4 | 2923874CD1 | 21 | 2923874CB1 |
| 55122335 | 5 | 55122335CD1 | 22 | 55122335CB1 |
| 7473550 | 6 | 7473550CD1 | 23 | 7473550CB1 |
| 7478108 | 7 | 7478108CD1 | 24 | 7478108CB1 |
| 7482021 | 8 | 7482021CD1 | 25 | 7482021CB1 |
| 7482145 | 9 | 7482145CD1 | 26 | 7482145CB1 |
| 55022586 | 10 | 55022586CD1 | 27 | 55022586CB1 |
| 3238072 | 11 | 3238072CD1 | 28 | 3238072CB1 |
| 7482034 | 12 | 7482034CD1 | 29 | 7482034CB1 |
| 7474351 | 13 | 7474351CD1 | 30 | 7474351CB1 |
| 2232483 | 14 | 2232483CD1 | 31 | 2232483CB1 |
| 7481712 | 15 | 7481712CD1 | 32 | 7481712CB1 |
| 8213480 | 16 | 8213480CD1 | 33 | 8213480CB1 |
| 7478405 | 17 | 7478405CD1 | 34 | 7478405CB1 |

TABLE 2

| Polypeptide SEQ ID NO: | Incyte Polypeptide ID | GenBank ID NO: | Probability score | GenBank Homolog |
|---|---|---|---|---|
| 1 | 6930294CD1 | g190418 | 4.50E–169 | [Homo sapiens] preprocathepsin L precursor (Joseph, L. J. et al. (1988) J. Clin. Invest. 81: 1621–1629) |
| 2 | 7473018CD1 | g5669607 | 2.20E–25 | [Equus caballus] caspase-1 Wardlow, S. et al. (1999) Nucleotide sequence of equine caspase-1 cDNA. DNA Seq. 10: 133–137. |
| 3 | 7479221CD1 | g6573163 | 3.80E–298 | [Rattus norvegicus] ubiquitin specific processing protease Lin, H. et al. (2000) Divergent N-terminal sequences |

TABLE 2-continued

| Polypeptide SEQ ID NO: | Incyte Polypeptide ID | GenBank ID NO: | Probability score | GenBank Homolog |
|---|---|---|---|---|
| | | | | target an inducible testis deubiquitinating enzyme to distinct subcellular structures. Mol. Cell Biol. 20: 6568–6578. |
| 4 | 2923874CD1 | g306706 | 5.20E−207 | [*Homo sapiens*] dipeptidyl aminopeptidase like protein (Yokotani, N. et al. (1993) Hum. Mol. Genet. 2: 1037–1039) |
| 5 | 55122335CD1 | g10800858 | 0 | [fl] [*Homo sapiens*] aminopeptidase B |
| 6 | 7473550CD1 | g2981641 | 6.40E−201 | [*Xenopus laevis*] ovochymase/ovotryptase polyprotease (Lindsay, L. L. et al. (1999) Proc. Natl. Acad. Sci. U.S.A. 96: 11253–11258) |
| 7 | 7478108CD1 | g544755 | 3.00E−166 | [*Oryctolagus cuniculus*] aminopeptidase N, APN {type II membrane protein} (Santos, A. N. et al. (2000) Cell. Immunol. 201: 22–32) |
| 8 | 7482021CD1 | g6573165 | 5.60E−210 | [*Rattus norvegicus*] testis ubiquitin specific processing protease Lin, H. et al. (2000) Divergent N-terminal sequences target an inducible testis deubiquitinating enzyme to distinct subcellular structures. Mol. Cell Biol. 20: 6568–6578. |
| 9 | 7482145CD1 | g6683668 | 1.70E−114 | [*Carassius auratus*] alpha 4 subunit of 20S proteasome (Tokumoto, M. et al. (2000) Eur. J. Biochem. 267: 97–103) |
| 10 | 55022586CD1 | g14279329 | 0 | [fl] [*Homo sapiens*] ubiquitin specific protease |
| 11 | 3238072CD1 | g5410230 | 5.50E−56 | [*Homo sapiens*] ubiquitin-specific protease 3 (Sloper-Mould, K. E. et al. (1999) J. Biol. Chem. 274: 26878–26884) |
| 12 | 7482034CD1 | g4545092 | 3.80E−60 | [*Sus scrofa*] proteasome subunit LMP7 (Chun, T. et al. (1999) Immunogenetics 49: 72–77) |
| 13 | 7474351CD1 | g4512604 | 5.00E−48 | [*Canis sp.*] mastin precursor (Rice, K. D. et al. (1998) Curr. Pharm. Des. 4: 381–396) |
| 14 | 2232483CD1 | g6465985 | 1.40E−229 | [[*Homo sapiens*] quiescent cell proline dipeptidase (Underwood, R. (1999) J. Biol. Chem. 274: 34053–34058) |
| 15 | 7481712CD1 | g13528975 | 1.00E−122 | [fl] [*Homo sapiens*] (BC005279) carboxypeptidase A1 (pancreatic) |
| 16 | 8213480CD1 | g13157560 | 0 | [3' incom] [*Homo sapiens*] dJ964F7.1 (novel disintegrin and reprolysin metalloproteinase family protein) |
| 17 | 7478405CD1 | g5923786 | 9.10E−164 | [*Homo sapiens*] zinc metalloprotease ADAMTS6 (Hurskainen, T. L. et al. (1999) J. Biol. Chem. 274: 25555–25563) |

TABLE 3

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 1 | 6930294CD1 | 333 | S160 S210 T155 T84 Y112 | N221 | Papain family cysteine protease Peptidase_C1: A114-T332 | HMMER_PFAM |
| | | | | | Eukaryotic thiol protease active site BL00139: Q132-F141, N175-M183, D275-S284, Y295-Y311 | BLIMPS_BLOCKS |
| | | | | | PAPAIN CYSTEINE PROTEASE PR00705: Q132-L147, H276-E286, Y295-R301 | BLIMPS_PRINTS |
| | | | | | EUKARYOTIC THIOL PROTEASES CYSTEINE DM00081\|P07711\|19–332: L19-V333 DM00081\|P25975\|20–333: D22-V333 DM00081\|P06797\|19–332: F21-V333 DM00081\|P15242\|20–332: T20-V333 | BLAST_DOMO |
| | | | | | PROTEASE PRECURSOR SIGNAL CYSTEINE PROTEINASE HYDROLASE THIOL ZYMOGEN CATHEPSIN GLYCOPROTEIN PD000158: S117-S218, C169-P331 PD000247: K31-E113 | BLAST_PRODOM |
| | | | | | Eukaryotic thiol (cysteine) protease active sites: Thiol_Protease_Cys: Q132-A143 Thiol_Protease_His: L274-S284 | MOTIFS |
| | | | | | Eukaryotic thiol (cysteine) protease active sites thiol_protease_cys.prf: E113-E163 thiol_protease_his.prf: Q257-G307 | PROFILESCAN |
| | | | | | signal_peptide: M1-T20 | HMMER |
| | | | | | signal_cleavage: M1-A17 | SPSCAN |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 2 | 7473018CD1 | 90 | S36 T49 T62 | N47 | CASPASE RECRUITMENT DOMAIN CARD: INTERLEUKIN-1 BETA CONVERTING ENZYME FAMILY HISTIDINE DM07463\|P29466\|1–122: M1-L89 DM07463\|P29452\|1–121: M1-L89 | HMMER_PFAM BLAST_DOMO |
|  |  |  |  |  | signal_cleavage: M1-S36 | SPSCAN |
| 3 | 7479221CD1 | 605 | S14 S142 S152 S158 S190 S207 S329 S335 S382 S42 S490 S506 S70 T12 T137 T175 T227 T235 T239 T377 T424 T433 T454 T463 T512 T572 T7 T99 Y17 Y22 | N548 N574 | Ubiquitin carboxyl-terminal hydrolase family 2 signatures UCH-1: A267-R298 UCH-2: N537-L598 | HMMER_PFAM |
|  |  |  |  |  | Ubiquitin carboxyl-terminal hydrolase family 2 signature BL00972: G268-L285, Y353-L362, I411-C425, V540-S564, T567-T588 | BLIMPS_BLOCKS |
|  |  |  |  |  | UBIQUITIN CARBOXYL-TERMINAL HYDROLASES FAMILY 2 DM00659\|P40818\|782–1103: L272-L594 DM00659\|P35123\|139–432: L272-I445 DM00659\|P35125\|220–508: L272-L455 DM00659\|P32571\|566–873: N271-F531 | BLAST_DOMO |
|  |  |  |  |  | PROTEASE UBIQUITIN HYDROLASE ENZYME UBIQUITINSPECIFIC CARBOXYLTERMINAL DEUBIQUITINATING THIOLESTERASE PROCESSING CONJUGATION PD000590: M258-S432 PD017412: F435-E534 | BLAST_PRODOM |
|  |  |  |  |  | Ubiquitin carboxyl-terminal hydrolase family 2 signatures Uch_2_1: G268-Q283 Uch_2_2: Y541-Y558 | MOTIFS |
| 4 | 2923874CD1 | 743 | S157 S163 S260 S304 S355 S393 S589 S593 S635 S643 S709 T238 T294 T361 T382 T423 T524 T71 Y508 | N204 N289 N58 N66 N695 N707 | Dipeptidyl peptidase IV active site signature DPPIV_N_term: M1-D525 | HMMER_PFAM |
|  |  |  |  |  | Prolyl oligopeptidase family Peptidase_S9: F527-I603 | HMMER_PFAM |
|  |  |  |  |  | Prolyl endopeptidase family BL00708B: D573-I603 | BLIMPS_BLOCKS |
|  |  |  |  |  | Dipeptidyl peptidase IV PF00930: H77-Y98, R159-P209, Y221-Y247, E265-E297, L365-I375, E420-N465, P499-I536, D537-K579, F615-P642, N665-L685 | BLIMPS_PFAM |
|  |  |  |  |  | PROLYL ENDOPEPTIDASE FAMILY SERINE DM02461\|P42659\|335–862: P222-E743 DM02461\|P27487\|192–765: E167-C727 DM02461\|I38593\|190–759: I169-C727 DM02461\|P33894\|340–930: I169-V694, Y221-H715 | BLAST_DOMO |
|  |  |  |  |  | DPP IV HYDROLASE PROTEASE SERINE PEPTIDASE DIPEPTIDASE TRANSMEMBRANE GLYCOPROTEIN PD003086: Y20-P493, S275-T524 PD003048: I603-C727 | BLAST_PRODOM |
| 5 | 55122335CD1 | 650 | S208 S318 S359 S496 T141 T368 T374 T386 T408 T412 |  | Peptidase family M1 Peptidase_M1: R32-G417 | HMMER_PFAM |
|  |  |  |  |  | MEMBRANE ALANYL DIPEPTIDASE FAMILY SIGNATURE PR00756: R176-Y191, F220-I235, F295-L305, V322-T337, W341-Y353 | BLIMPS_PRINTS |
|  |  |  |  |  | Neutral Zn metalloprotease, Zn-binding region BL00142: V322-F332 | BLIMPS_BLOCKS |
|  |  |  |  |  | do HYDROLASE; LEUKOTRIENE; A-4; ZINC; DM08707\|P19602\|7–609: H38-H634 DM08707\|Q10740\|58–670: W152-H634, A26-S82 | BLAST_DOMO |
|  |  |  |  |  | do ZINC; AMINOPEPTIDASE; METALLOPEPTIDASE; NEUTRAL; DM00700\|I55441\|163–916: A159-P489 DM00700\|S47274\|1–784: G160-P489 | BLAST_DOMO |
|  |  |  |  |  | AMINOPEPTIDASE B EC 3.4.11.6 ARGINYL ARGININE CYTOSOL IV APB HYDROLASE ZINC METALLOPROTEASE PD143187: A2-F165 | BLAST_PRODOM |
|  |  |  |  |  | HYDROLASE ZINC METALLOPROTEASE LEUKOTRIENE A4 LTA4 A4 MULTIFUNCTIONAL ENZYME BIOSYNTHESIS PD008823: Y533-Q643 | BLAST_PRODOM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | AMINOPEPTIDASE HYDROLASE METALLOPROTEASE ZINC N GLYCOPROTEIN TRANSMEMBRANE SIGNALANCHOR MEMBRANE PD001134: R248-D518 | BLAST_PRODOM |
| | | | | | Neutral Zn metalloprotease, Zn-binding region Zinc_Protease: V322-W331 | MOTIFS |
| 6 | 7473550CD1 | 932 | S319 S326 S353 S387 S394 S426 S49 S565 S665 S708 S840 S906 S91 S93 T103 T126 T297 T337 T454 T545 T744 T853 T910 Y735 | N324 N424 N500 N52 N706 N99 | Trypsin family active site trypsin: I47-I291, I568-I809 | HMMER_PFAM |
| | | | | | CUB domain CUB: S310-V400, C412-F521 | HMMER_PFAM |
| | | | | | Serine proteases, trypsin family active site BL00134: C593-C609, D759-G782, P796-I809 | BLIMPS_BLOCKS |
| | | | | | Kringle domain proteins BL00021B: C72-L89 | BLIMPS_BLOCKS |
| | | | | | CHYMOTRYPSIN SERINE PROTEASE ACTIVE SITE PR00722: G594-C609, S653-L667 | BLIMPS_PRINTS |
| | | | | | TRYPSIN DM00018\|P23578\|42–289: R567-I813, R46-P268 DM00018\|A57014\|45–284: I568-I813, N52-P268 DM00018\|P48038\|39–286: R567-I813, P259-P268 DM00018\|P03952\|392–624: G570-K812, N52-Q293 | BLAST_DOMO |
| | | | | | PROTEASE SERINE PRECURSOR SIGNAL HYDROLASE ZYMOGEN GLYCOPROTEIN FAMILY MULTIGENE FACTOR PD000046: G589-I809, W50-I291 | BLAST_PRODOM |
| | | | | | Serine proteases, trypsin family, active sites Trypsin_His: V83-C88, L604-C609 Trypsin_Ser: D231-V242 | MOTIFS |
| | | | | | Serine proteases, trypsin family, active sites trypsin_his.prf: L64-Q115, L585-T634 trypsin_ser.prf: L216-G264, I743-Q792 | PROFILESCAN |
| | | | | | signal_peptide: M1-G22 | HMMER |
| | | | | | signal_cleavage: M1-G22 | SPSCAN |
| 7 | 7478108CD1 | 990 | S200 S237 S282 S353 S442 S536 S54 S631 S641 S643 S74 S835 S917 S979 T128 T134 T141 T321 T403 T562 T605 T69 T706 T850 T885 T967 T990 | N132 N168 N261 N288 N319 N338 N346 N360 N582 N600 N607 N619 N653 N848 N887 | Peptidase family M1 Peptidase_M1: L98-G506 | HMMER_PFAM |
| | | | | | MEMBRANE ALANYL DIPEPTIDASE FAMILY SIGNATURE PR00756: W431-Y443, R245-F260, F297-I312, F376-L386, V412-T427 | BLIMPS_PRINTS |
| | | | | | Neutral Zn metalloprotease, Zn-binding region BL00142: V412-F422 | BLIMPS_BLOCKS |
| | | | | | do ZINC; AMINOPEPTIDASE; METALLOPEPTIDASE; NEUTRAL; DM00700\|P15541\|67–903: W93-I932 DM00700\|P15145\|66–901: W93-I929 DM00700\|P15684\|70–903: W93-I929 DM00700\|P15144\|70–904: W93-I932 | BLAST_DOMO |
| | | | | | AMINOPEPTIDASE HYDROLASE METALLOPROTEASE ZINC GLYCOPROTEIN TRANSMEMBRANE SIGNALANCHOR PD001134: Q95-T585 PD002091: V587-Y874 | BLAST_PRODOM |
| | | | | | Neutral Zn metalloprotease, Zn-binding region Zinc_Protease: V412-W421 | MOTIFS |
| | | | | | signal_peptide: M1-A31 | HMMER |
| | | | | | signal_cleavage: M1-A34 | SPSCAN |
| | | | | | transmembrane domain: A16-Y37 | HMMER |
| 8 | 7482021CD1 | 396 | S120 S126 S173 S281 S297 T168 T215 T224 T245 T254 T303 T363 T8 | N339 N365 | Ubiquitin carboxyl-terminal hydrolase family 2 UCH-1: A58-R89 UCH-2: N328-L389 | HMMER_PFAM |
| | | | | | Ubiquitin carboxyl-terminal hydrolase family 2 BL00972: G59-L76, Y144-L153, I202-C216, V331-S355, T358-T379 | BLIMPS_BLOCKS |
| | | | | | UBIQUITIN CARBOXYL-TERMINAL HYDROLASE FAMILY 2 DM00659\|P40818\|782–1103: L63-L385 DM00659\|P35123\|139–432: L63-I236 DM00659\|P35125\|220–508: L63-L246 DM00659\|P32571\|566–873: N62-F322 | BLAST_DOMO |
| | | | | | PROTEASE UBIQUITINSPECIFIC HYDROLASE ENZYME C-TERMINAL DEUBIQUITINATING THIOLESTERASE PROCESSING CONJUGATION PD000590: S51-S223 | BLAST_PRODOM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | PD017412: F226-E325 | |
| | | | | | Ubiquitin carboxyl-terminal hydrolase family 2 Uch_2_1: G59-Q74 Uch_2_2: Y332-Y349 | MOTIFS |
| | | | | | signal_cleavage: M1-N46 | SPSCAN |
| 9 | 7482145CD1 | 250 | S166 S185 S223 S246 S3 S32 S95 T115 T169 T232 T60 T99 Y178 | N177 | Proteasome A-type and B-type proteasome: T33-T179 | HMMER_PFAM |
| | | | | | Proteasome A-type subunits signature BL00388: Y5-K50, K63-V104, Q118-D139, L146 -K176 | BLIMPS_BLOCKS |
| | | | | | Proteasome A-type and B-type PF00227: F12-Y23 | BLIMPS_PFAM |
| | | | | | Proteasome A-type subunits signature proteasome.prf: M1-V47 | PROFILESCAN |
| | | | | | PROTEASOME A-TYPE SUBUNITS DM00341\|P48004\|1–226: Y5-S223 DM00341\|S23451\|3–222: S3-M221 DM00341\|P22769\|3–222: S3-M221 DM00341\|P34120\|4–220: S3-L219 | BLAST_DOMO |
| | | | | | PROTEASOME HYDROLASE PROTEASE SUBUNIT MULTICATALYTIC COMPLEX ENDOPEPTIDASE MACROPAIN COMPONENT PROTEIN PD000280: S32-K191 | BLAST_PRODOM |
| | | | | | Proteasome A-type subunits signature Proteasome_A: Y5-A27 | MOTIFS |
| 10 | 55022586CD1 | 1045 | S47, S76, S109, S113, T130, T134, S137, S205, T207, S228, S248, T260, S279, S347, S368, S453, S479, T484, T489, S494, S503, S504, S517, S520, T532, T534, S550, S620, S624, S625, T662, S668, S700, S713, T719, T753, S760, S787, T813, S824, S867, T872, Y888, S930, T934, S939, S964, T1016, S1021, T1043 | N282, N310, N373, N639, N711, N822 | PROBABLE UBIQUITIN CARBOXYLTERMINAL HYDROLASE K02C4.3 EC 3.1.2.15 THIOLESTERASE UBIQUITINSPECIFIC PROCESSING PROTEASE DEUBIQUITINATING ENZYME HYPOTHETICAL PROTEIN CONJU-GATION THIOL: PD138085: F540-S720, Y316-S720 | BLAST-PRODOM |
| | | | | | Ubiquitin carboxyl-terminal hydrolase family 2 proteins: BL00972: G163-L180, E251-T260, P583-N607, R610-R631 | BLIMPS-BLOCKS |
| | | | | | Ubiquitin carboxyl-terminal hydrolase family: UCH-1: V162-Y193, UCH-2: R580-N649 | HMMER-PFAM |
| | | | | | Ubiquitin carboxyl-terminal hydrolase family: Uch_2_2: Y584-Y601 | MOTIFS |
| 11 | 3238072CD1 | 622 | S142 S166 S221 S238 S245 S250 S285 S304 S363 S455 S460 S493 S523 S56 S574 S611 S96 T149 T165 T173 T354 T355 T368 T438 T50 T589 T88 | N243 N424 N566 | Ubiquitin carboxyl-terminal hydrolase family 2 UCH-1: T187-L218 UCH-2: E528-Q590 | HMMER_PFAM |
| | | | | | Ubiquitin carboxyl-terminal hydrolase family 2 BL00972: G188-L205, Y329-L338; V375-C389, Y532-N556, G559-K580 | BLIMPS_BLOCKS |
| | | | | | UBIQUITIN CARBOXYL-TERMINAL HYDROLASES FAMILY 2 DM00659\|P40818\|782–1103: L291-G542, V421-L586, L192-F215 DM00659\|Q09738\|149–388: K306-V421, V421-G542, N191-N217 DM00659\|S57874\|537–787: H288-T426, L192-N217 | BLAST_DOMO |
| | | | | | PROTEASE UBIQUITINSPECIFIC HYDROLASE ENZYME CARBOXYLTERMINAL DEUBIQUITINATING THIOLESTERASE PROCESSING CONJUGATION PD000590: N281-T398, A183-T223 | BLAST_PRODOM |
| | | | | | Ubiquitin carboxyl-terminal hydrolase family 2 Uch_2_1: G188-Q203 Uch_2_2: Y532-Y550 | MOTIFS |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 12 | 7482034CD1 | 345 | S125 S201 S242 S276 S282 S37 T142 T258 T332 Y207 | | Proteasome A-type and B-type subunit proteasome: T96-R238 | HMMER_PFAM |
| | | | | | Proteasome B-type subunit BL00854: A99-A144, F206-D234, A257-G266 | BLIMPS_BLOCKS |
| | | | | | PROTEASOME COMPONENT SIGNATURE PR00141: H259-L270, F102-G117, G223-D234, D234-E245 | BLIMPS_PRINTS |
| | | | | | PROTEASOME B-TYPE SUBUNITS DM00618\|P28062\|46–260: G77-V281 DM00618\|P30656\|48–264: P80-W278 DM00618\|P28072\|5–222: P80-E279 DM00618\|I49120\|1–185: L98-E279 | BLAST_DOMO |
| | | | | | PROTEASOME HYDROLASE PROTEASE SUBUNIT MULTICATALYTIC COMPLEX ENDOPEPTIDASE MACROPAIN COMPONENT PD000280: T95-E245 | BLAST_PRODOM |
| | | | | | Proteasome_B: L98-D145 | MOTIFS |
| | | | | | signal_peptide: M1-A30 | HMMER |
| | | | | | signal_cleavage: M1-A30 | SPSCAN |
| 13 | 7474351CD1 | 948 | S179 S19 S194 S287 S310 S514 S522 S613 S648 S687 S751 S923 T150 T315 T327 T337 T578 T653 T718 T722 T738 T760 T919 T95 Y467 | N159 N247 N325 N335 N372 N630 | Trypsin family serine protease active site trypsin: A218-I406, V419-Q496, L636-R761 | HMMER_PFAM |
| | | | | | Trypsin family serine protease active site trypsin_ser.prf: R705-G748 | PROFILESCAN |
| | | | | | CHYMOTRYPSIN SERINE PROTEASE PR00722C: R720-V732 | BLIMPS_PRINTS |
| | | | | | TRYPSIN DM00018\|P19236\|20–262: E212-Q408, L636-W766 DM00018\|P21845\|31–271: F219-Q408, L643-R761 DM00018\|Q02844\|29–268: R220-I406, P629-R761 DM00018\|P15157\|31–270: E215-I406, P629-R761 | BLAST_DOMO |
| | | | | | PROTEASE SERINE PRECURSOR SIGNAL HYDROLASE ZYMOGEN GLYCOPROTEIN FAMILY MULTIGENE PD000046: D232-I406 | BLAST_PRODOM |
| | | | | | Kringle domain proteins BL00021: V276-G297, G365-I406 | BLIMPS_BLOCKS |
| 14 | 2232483CD1 | 444 | S291 S305 S402 S409 S60 T121 T212 T314 T75 | N289 N330 N337 N380 N50 N86 | Prolyl aminopeptidase family PR00793C: V158-R172 | BLIMPS_PRINTS |
| | | | | | Prolyl oligopeptidase family BL00862D: G160-A180 | BLIMPS_PRINTS |
| | | | | | Prolyl endopeptidase family BL00708B: D137-L167 | BLIMPS_BLOCKS |
| | | | | | alpha/beta hydrolase fold abhydrolase: A100-A334 | HMMER_PFAM |
| | | | | | do LYSOSOMAL; PRO-X; CARBOXYPEPTIDASE; DM03192\|P42785\|3–487: A4-T206, V213-F342, D355-E417 DM03192\|P34676\|1–498: F31-V189, Y210-I377, S354-K426 DM03192\|P34610\|31–480: R39-F342, Q324-R414 DM03192\|P34528\|84–584: F36-A191, C326-K415, S291-T339 | BLAST_DOMO |
| | | | | | PROTEIN CARBOXYPEPTIDASE LYSOSOMAL PROX SIMILAR HUMAN CHROMOSOME III F23B2.12 PD149833: L243-N337, S360-L416 | BLAST_PRODOM |
| | | | | | signal_peptide: M1-A21 | HMMER |
| | | | | | Leucine_Zipper: L128-L149 | MOTIFS |
| | | | | | signal_cleavage: M1-A21 | SPSCAN |
| 15 | 7481712CD1 | 514 | S202 S225 S336 S377 T219 T316 T494 T504 Y436 | N115 N249 N334 N359 N93 | Zinc carboxypeptidase Zn binding region Zn_carbOpept: Y217-E497 | HMMER_PFAM |
| | | | | | Zinc carboxypeptidases, Zn binding region BL00132: Y217-F257, P265-W278, Y295-K335, P339-K353, P365-H391, N393-L414, T450-G467 | BLIMPS_BLOCKS |
| | | | | | CARBOXYPEPTIDASE A METALLOPROTEASE FAMILY PR00765: I243-L255, P265-I279, G345-K353, I398-Y411 | BLIMPS_PRINTS |
| | | | | | Zn carboxypeptidases, Zn-binding region signatures carboxypept_zn_2.prf: E380-L435 | PROFILESCAN |
| | | | | | ZINC CARBOXYPEPTIDASES, ZINC-BINDING | BLAST_DOMO |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | REGION 1 DM00683\|P15085\|112–418: R207-P513 DM00683\|P48052\|111–416: E206-P513 DM00683\|A56171\|111–416: E206-P513 DM00683\|P19222\|111–416: E206-P513 | |
| | | | | | CARBOXYPEPTIDASE PRECURSOR SIGNAL HYDROLASE ZINC ZYMOGEN PROTEIN D B GP180CARBOXYPEPTIDASE PD001916: Y217-Y411 | BLAST_PRODOM |
| | | | | | Zinc carboxypeptidases, Zn binding region signatures Carboxypept_Zn_1: P265-T287 Carboxypept_Zn_2: H401-Y411 | MOTIFS |
| 16 | 8213480CD1 | 787 | S162 S389 S450 S547 S55 S61 S761 T174 T208 T258 T264 T302 T605 Y243 | N109 N145 N231 N276 N448 | Reprolysin (M12B) family zinc metalloprotease Reprolysin: K210-P409 | HMMER_PFAM |
| | | | | | Reprolysin family propeptide Pep_M12B_propep: E80-Q198 | HMMER_PFAM |
| | | | | | Neutral Zn metallopeptidase Zn-binding region BL00142: T342-G352 | BLIMPS_BLOCKS |
| | | | | | Neutral Zn metallopeptidase Zn-binding region zinc_protease.prf: E323-A376 | PROFILESCAN |
| | | | | | Disintegrin signature disintegrin: E426-L501 | HMMER_PFAM |
| | | | | | Disintegrins signature disintegrins.prf: G352-D498 | PROFILESCAN |
| | | | | | Disintegrin signature BL00427: C443-P497 | BLIMPS_BLOCKS |
| | | | | | DISINTEGRIN SIGNATURE PR00289: C457-R476, E486-D498 | BLIMPS_PRINTS |
| | | | | | do ZINC; NEUTRAL METALLOPEPTIDASE; ATROLYSIN; DM00368\|S60257\|204–414: R202-D410 DM00368\|Q05910\|189–395: R206-D410 DM00368\|P28891\|1–202: E204-P409 | BLAST_DOMO |
| | | | | | do ZINC; REGULATED; EPIDIDYMAL; NEUTRAL; DM00591\|S60257\|492–628: F487-G608 | BLAST_DOMO |
| | | | | | METALLOPROTEASE PRECURSOR HYDROLASE SIGNAL ZINC VENOM CELL TRANSMEMBRANE ADHESION PD000791: R209-P409 PD000935: L70-M169 | BLAST_PRODOM |
| | | | | | CELL ADHESION PLATELET BLOOD COAGULATION VENOM DISINTEGRIN METALLOPROTEASE PRECURSOR SIGNAL PD000664: E426-Y500 | BLAST_PRODOM |
| | | | | | TRANSMEMBRANE METALLOPROTEASE SIGNAL PRECURSOR GLYCOPROTEIN CELL FERTILIN BETA ADHESION PD001269: D503-L572 | BLAST_PRODOM |
| | | | | | signal_peptide: M1-G27 | HMMER |
| | | | | | Neutral Zn metallopeptidase Zn binding region Zinc_Protease: T342-L351 | MOTIFS |
| | | | | | signal_cleavage: M1-G27 | SPSCAN |
| 17 | 7478405CD1 | 1082 | S1021 S1060 S220 S279 S289 S396 S631 S698 S795 S89 S914 S953 T1025 T135 T171 T206 T390 T421 T65 T674 T747 T817 T871 Y270 | N151 N190 N313 N745 N838 N909 | Reprolysin family propeptide Pep_M12B_propep: E111-R222 | HMMER_PFAM |
| | | | | | Reprolysin (M12B) family zinc metalloprotease zinc binding region Reprolysin: V295-P498 | HMMER_PFAM |
| | | | | | Neutral Zn metalloprotease, Zn-binding region BL00142: T433-G443 | BLIMPS_BLOCKS |
| | | | | | do ZINC; METALLOPEPTIDASE; NEUTRAL; ATROLYSIN; DM00368\|Q05910\|189–395: V295-P498 DM00368\|S48169\|140–343: V295-P498 DM00368\|P34179\|1–202: V295-P498 DM00368\|P15167\|190–392: V295-P498 | BLAST_DOMO |
| | | | | | METALLOPROTEASE PRECURSOR HYDROLASE SIGNAL ZINC VENOM CELL PROTEIN TRANSMEMBRANE ADHESION PD000791: V295-P498 | BLAST_PRODOM |
| | | | | | PROTEIN PROCOLLAGEN THROMBOSPONDIN MOTIFS NPROTEINASE A DISINTEGRIN METALLOPROTEASE WITH ADAMTS1 PD011654: V676-C748 PD013511: K509-V578 | BLAST_PRODOM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | Thrombospondin type 1 domain tsp_1: S593-C643, R873-C931, G938-C991, P993-C1048 | HMMER_PFAM |
| | | | | | signal_cleavage: M1-S16 | SPSCAN |

TABLE 4

| Polynucleotide SEQ ID NO: | Incyte Polynucleotide ID | Sequence Length | Selected Fragment(s) | Sequence Fragments | 5' Position | 3' Position |
|---|---|---|---|---|---|---|
| 18 | 6930294CB1 | 1187 | 1091–1187 | 6917460H1 (PLACFER06) | 217 | 927 |
| | | | | GBI: g7939149_000003.2.edit | 814 | 1187 |
| | | | | 5118206F6 (SMCBUNT01) | 1 | 506 |
| 19 | 7473018CB1 | 461 | | g1365166 | 1 | 461 |
| | | | | GNN.g7651935_000011_002 | 21 | 293 |
| 20 | 7479221CB1 | 1884 | 591–773 | 6981403H1 (BRAIFER05) | 1144 | 1758 |
| | | | | 6618712H1 (BRAITDR02) | 375 | 1024 |
| | | | | 7269080H1 (OVARDIJ01) | 977 | 1598 |
| | | | | 1241675R6 (LUNGNOT03) | 1311 | 1884 |
| | | | | GBI.g7960351_edit | 1 | 774 |
| 21 | 2923874CB1 | 2576 | 1–158 | 72004319V1 | 490 | 1356 |
| | | | | 71998773V1 | 1899 | 2576 |
| | | | | 7015044F8 (KIDNNOC01) | 1 | 591 |
| | | | | 72004394V1 | 1276 | 2171 |
| 22 | 55122335CB1 | 2000 | 1792–2000 | 8268324H1 (BLYRTXF01) | 1 | 636 |
| | | | | 70942077V1 | 1323 | 1994 |
| | | | | 7699471H1 (KIDPTDE01) | 578 | 1226 |
| | | | | 71984458V1 | 1365 | 2000 |
| | | | | 71986878V1 | 1255 | 1928 |
| | | | | 55114534J1 | 677 | 1275 |
| 23 | 7473550CB1 | 3522 | 1–735, 2323–2786, 1799–1940, 930–1690, 2913–3522, 2140–2240 | FL7473550_g8102345_000 001_g2981641 | 98 | 3522 |
| | | | | GNN.g7076703_000017_002 | 1 | 312 |
| 24 | 7478108CB1 | 3277 | 709–831, 1–179, 3244–3277, 1957–2354 | 6926255F8 (PLACFER06) | 2274 | 2745 |
| | | | | 6923595F6 (PLACFER06) | 1750 | 2603 |
| | | | | 55142456J1 | 1 | 736 |
| | | | | 55047371J1 | 666 | 1574 |
| | | | | 55047372J1 | 1063 | 1960 |
| | | | | 6926255H1 (PLACFER06) | 2273 | 2689 |
| | | | | 5329258F6 (DRGTNON04) | 2801 | 3277 |
| | | | | GBI.g9256180_000003_000004.edit | 2708 | 3268 |
| 25 | 7482021CB1 | 1254 | 1–76 | g3016366 | 77 | 592 |
| | | | | 7037834H1 (UTRSTMR02) | 180 | 645 |
| | | | | 1241675R6 (LUNGNOT03) | 684 | 1254 |
| | | | | 6450560H1 (BRAINOC01) | 594 | 1238 |
| | | | | GBI.g7960351_edit_1 | 1 | 147 |
| 26 | 7482145CB1 | 1120 | 806–854 | 70197639V1 | 1 | 448 |
| | | | | GBI.g8516058_edit | 111 | 863 |
| | | | | 70166902V1 | 661 | 1120 |
| 27 | 55022586CB1 | 4577 | 1–71, 4368–4577, 986–2809 | 55057844J1 | 583 | 1360 |
| | | | | 71764468V1 | 2926 | 3719 |
| | | | | 6920230F6 (PLACFER06) | 1290 | 2134 |
| | | | | 71760331V1 | 2434 | 3064 |
| | | | | 71760332V1 | 3836 | 4381 |
| | | | | 5763279F8 (PROSBPT02) | 3899 | 4577 |
| | | | | 71188036V1 | 2409 | 3037 |
| | | | | 55022577H1 | 788 | 1479 |
| | | | | 55057841H1 | 1 | 738 |
| | | | | 71764426V1 | 3058 | 3795 |
| | | | | 2725111T6 (OVARTUT05) | 3772 | 4359 |
| | | | | 6920230R6 (PLACFER06) | 1589 | 2433 |
| 28 | 3238072CB1 | 1952 | 592–644, 1820–1952 | 71929643V1 | 659 | 1445 |
| | | | | GBI.g10186764_000001.edit | 1762 | 1952 |
| | | | | 3238072F6 (COLAUCT01) | 1127 | 1830 |

TABLE 4-continued

| Polynucleotide SEQ ID NO: | Incyte Polynucleotide ID | Sequence Length | Selected Fragment(s) | Sequence Fragments | 5' Position | 3' Position |
|---|---|---|---|---|---|---|
| | | | | 7725175J1 (THYRDIE01) | 1 | 685 |
| | | | | 71928050V1 | 781 | 1460 |
| 29 | 7482034CB1 | 1092 | 1–181, 924–1092 | GBI.g9756020_000001.edit | 1 | 174 |
| | | | | GNN.g8217882_012 | 55 | 1092 |
| 30 | 7474351CB1 | 2847 | 1–290, 500–2847 | 60123248D3 | 901 | 1116 |
| | | | | GBI: g9798436_CDS_1 | 1 | 2847 |
| | | | | CpG_WDJ300089003.R1 | 1323 | 1489 |
| | | | | 3532405H1 (KIDNNOT25) | 960 | 1164 |
| 31 | 2232483CB1 | 1396 | 1–25 | 8094675H1 (EYERNOA01) | 636 | 1096 |
| | | | | 71152873V1 | 858 | 1396 |
| | | | | 1628644F6 (COLNPOT01) | 1 | 482 |
| | | | | 60220501D1 | 459 | 833 |
| 32 | 7481712CB1 | 1853 | 1–873 | 6810286H1 (SKIRNOR01) | 1 | 547 |
| | | | | 55051982H1 | 876 | 1416 |
| | | | | GNN: g5306288_002 | 90 | 1853 |
| 33 | 8213480CB1 | 3344 | 1–1904, 2575–2624 | 1479739H1 (CORPNOT02) | 1592 | 1837 |
| | | | | 7174969F8 (BRSTTMC01) | 610 | 1253 |
| | | | | 6831592H1 (SINTNOR01) | 1 | 334 |
| | | | | 72142924D1 | 1922 | 2427 |
| | | | | 7663110F6 (UTRSTME01) | 573 | 1021 |
| | | | | 2786453T6 (BRSTNOT13) | 2780 | 3344 |
| | | | | 55113148H1 | 2325 | 3142 |
| | | | | 6958043R8 (BLADNOR01) | 196 | 644 |
| | | | | 1252335T6 (LUNGFET03) | 2663 | 3341 |
| | | | | 7659180J1 (OVARNOE02) | 1716 | 2302 |
| 34 | 7478405CB1 | 3389 | 563–3086 | 72420192D1 | 865 | 1338 |
| | | | | g6702073 | 1 | 561 |
| | | | | 4018316F8 (BRAXNOT01) | 2756 | 3219 |
| | | | | 58005173H1 | 2118 | 2793 |
| | | | | 55123782H1 | 1340 | 2115 |
| | | | | 55141002J1 | 567 | 1334 |
| | | | | 55065490J1 | 1300 | 1997 |
| | | | | 55123882J1 | 2095 | 2747 |
| | | | | g1550049 | 3089 | 3389 |
| | | | | 4293359F6 (BRABDIR01) | 336 | 816 |

TABLE 5

| Polynucleotide SEQ ID NO: | Incyte Project ID | Representative Library |
|---|---|---|
| 18 | 6930294CB1 | CONFNOT03 |
| 20 | 7479221CB1 | LUNGNOT03 |
| 21 | 2923874CB1 | BRAINOT22 |
| 22 | 55122335CB1 | KIDEUNE02 |
| 24 | 7478108CB1 | PLACFER06 |
| 25 | 7482021CB1 | LUNGNOT03 |
| 26 | 7482145CB1 | COLITUT02 |
| 27 | 55022586CB1 | PROSTUS23 |
| 28 | 3238072CB1 | ESOGTUE01 |
| 30 | 7474351CB1 | KIDNNOT25 |
| 31 | 2232483CB1 | BRSTNOT05 |
| 32 | 7481712CB1 | SKIRNOR01 |
| 33 | 8213480CB1 | UTRSTME01 |
| 34 | 7478405CB1 | ENDMUNE01 |

TABLE 6

| Library | Vector | Library Description |
|---|---|---|
| BRAINOT22 | pINCY | Library was constructed using RNA isolated from right temporal lobe tissue removed from a 45-year-old Black male during a brain lobectomy. Pathology for the associated tumor tissue indicated dysembryoplastic neuroepithelial tumor of the right temporal lobe. The right temporal region dura was consistent with calcifying pseudotumor of the neuraxis. Family history included obesity, benign hypertension, cirrhosis of the liver, obesity, hyperlipidemia, cerebrovascular disease, and type II diabetes. |

TABLE 6-continued

| Library | Vector | Library Description |
|---|---|---|
| BRSTNOT05 | PSPORT1 | Library was constructed using RNA isolated from breast tissue removed from a 58-year-old Caucasian female during a unilateral extended simple mastectomy. Pathology for the associated tumor tissue indicated multicentric invasive grade 4 lobular carcinoma. Patient history included skin cancer, rheumatic heart disease, osteoarthritis, and tuberculosis. Family history included cerebrovascular and cardiovascular disease, breast and prostate cancer, and type I diabetes. |
| COLITUT02 | pINCY | Library was constructed using RNA isolated from colon tumor tissue of the ileocecal valve removed from a 29-year-old female. Pathology indicated malignant lymphoma, small cell, non-cleaved (Burkitt's lymphoma, B-cell phenotype), forming a polypoid mass in the region of the ileocecal valve, associated with intussusception and obstruction clinically. The liver and multiple (3 of 12) ileocecal region lymph nodes were also involved by lymphoma. |
| CONFNOT03 | pINCY | Library was constructed using RNA isolated from mesenteric fat tissue removed from a 71-year-old Caucasian male during a partial colectomy and permanent colostomy. Pathology indicated mesenteric fat tissue associated with diverticulosis and diverticulitis with abscess formation. Approximately 50 diverticula were noted, one of which was perforated and associated with abscess formation in adjacent mesenteric fat. The patient presented with atrialfibrillation. Patient history included viral hepatitis, a hemangioma, and diverticulitis of colon. Family history included extrinsic asthma, atheroscleroticcoronary artery disease, and myocardial infarction. |
| ENDMUNE01 | pINCY | This 5' biased random primed library was constructed using RNA isolated from untreated umbilical artery endothelial cell tissue removed from a Caucasian male (Clonetics) newborn. |
| ESOGTUE01 | pINCY | This 5' biased random primed library was constructed using RNA isolated from esophageal tumor tissue removed from a 61-year-old Caucasian male during a partial esophagectomy, proximal gastrectomy, pyloromyotomy, and regional lymph node excision. Pathology indicated an invasive grade 3 adenocarcinoma in the esophagus, extending distally to involve the gastroesophageal junction. The tumor extended through the muscularis to involve periesophageal and perigastric soft tissues. One perigastric and two periesophageal lymph nodes were positive for tumor. There were multiple perigastric and periesophageal tumor implants. The patient presented with deficiency anemia and myelodysplasia. Patient history included hyperlipidemia, and tobacco and alcohol abuse in remission. Previous surgeries included adenotonsillectomy, rhinoplasty, vasectomy, and hemorrhoidectomy. A previous bone marrow aspiration found the marrow to be hypercellular for age and had a cellularity-to-fat ratio of 95:5. The marrow was focally densely fibrotic. Granulocytic precursors were slightly increased with normal maturation. The estimate of blast cells was greater than 5%. Megakaryocytes were increased and appeared atypical in clusters. Storage cells and granulomata were absent. Patient medications included Epoetin, Danocrine, Berocca Plus tablets, Selenium, vitamin B6 phosphate, vitamins E & C, and beta carotene. Family history included alcohol abuse, atherosclerotic coronary artery disease, type II diabetes, chronic liver disease, and primary cardiomyopathy in the father; and benign hypertension and cerebrovascular disease in the mother. |
| KIDEUNE02 | pINCY | This 5' biased random primed library was constructed using RNA isolated from an untreated transformed embryonal cell line (293-EBNA) derived from kidney epithelial tissue (Invitrogen). The cells were transformed with adenovirus 5 DNA. |
| KIDNNOT25 | pINCY | Library was constructed using RNA isolated from kidney tissue removed from the left lower kidney pole of a 42-year-old Caucasian female during nephroureterectomy. Pathology indicated slight hydronephrosis and nephrolithiasis. Patient history included calculus of the kidney. |
| LUNGNOT03 | PSPORT1 | Library was constructed using RNA isolated from lung tissue of a 79-year-old Caucasian male. Pathology for the associated tumor tissue indicated grade 4 carcinoma. Patient history included a benign prostate neoplasm and atherosclerosis. |
| PLACFER06 | pINCY | This random primed library was constructed using RNA isolated from placental tissue removed from a Caucasian fetus who died after 16 weeks' gestation from fetal demise and hydrocephalus. Patient history included umbilical cord wrapped around the head (3 times) and the shoulders (1 time). Serology was positive for anti-CMV. Family history included multiple pregnancies and live births, and an abortion. |
| PROSTUS23 | pINCY | This subtracted prostate tumor library was constructed using 10 million clones from a pooled prostate tumor library that was subjected to 2 rounds of subtractive hybridization with 10 million clones from a pooled prostate tissue library. The starting library for subtraction was constructed by pooling equal numbers of clones from 4 prostate tumor libraries using mRNA isolated from prostate tumor removed from Caucasian males at ages 58 (A), 61 (B), 66 (C), and 68 (D) during prostatectomy with lymph node excision. Pathology indicated adenocarcinoma in all donors. History included elevated PSA, induration and tobacco abuse in donor A; elevated PSA, induration, prostate hyperplasia, renal failure, osteoarthritis, renal artery stenosis, benign HTN, thrombocytopenia, hyperlipidemia, tobacco/alcohol abuse and hepatitis C (carrier) in donor B; elevated PSA, induration, and tobacco abuse in donor C; and elevated PSA, induration, hypercholesterolemia, and kidney calculus in donor D. The hybridization probe for subtraction was constructed by pooling equal numbers of cDNA clones from 3 prostate tissue libraries derived from prostate tissue, prostate epithelial cells, |

TABLE 6-continued

| Library | Vector | Library Description |
|---|---|---|
| | | and fibroblasts from prostate stroma from 3 different donors. Subtractive hybridization conditions were based on the methodologies of Swaroop et al., NAR 19 (1991): 1954 and Bonaldo, et al. Genome Research 6 (1996): 791. |
| SKIRNOR01 | PCDNA2.1 | This random primed library was constructed using RNA isolated from skin tissue removed from the breast of a 17-year-old Caucasian female during bilateral reduction mammoplasty. Patient history included breast hypertrophy. Family history included benign hypertension. |
| UTRSTME01 | PCDNA2.1 | This 5' biased random primed library was constructed using RNA isolated from uterus tissue removed from a 49-year-old Caucasian female during vaginal hysterectomy and bilateral salpingo-oophorectomy. Pathology for the matched tumor tissue indicated multiple (6) intramural leiomyomata. The patient presented with excessive menstruation, deficiency anemia, and dysmenorrhea. Patient history included abdominal pregnancy, headache, and chronic obstructive asthma. Previous surgeries included hemorrhoidectomy, knee ligament repair, and intranasal lesion destruction. Patient medications included Azmacort, Proventil, Trazadone, Zostrix HP, iron, Premarin, and vitamin C. Family history included alcohol abuse, atherosclerotic coronary artery disease, upper lobe lung cancer, and carotid endarterectomy in the father; breast fibroadenosis in the sibling(s); and acute myocardial infarction, liver cancer, acute leukemia, and breast cancer (central) in the grandparent(s). |

TABLE 7

| Program | Description | Reference | Parameter Threshold |
|---|---|---|---|
| ABIFACTURA | A program that removes vector sequences and masks ambiguous bases in nucleic acid sequences. | Applied Biosystems, Foster City, CA. | |
| ABI/PARACEL FDF | A Fast Data Finder useful in comparing and annotating amino acid or nucleic acid sequences. | Applied Biosystems, Foster City, CA; Paracel Inc., Pasadena, CA. | Mismatch < 50% |
| ABI AutoAssembler | A program that assembles nucleic acid sequences. | Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215: 403–410; Altschul, S. F. et al. (1997) Nucleic Acids Res. 25: 3389–3402. | ESTs: Probability value = 1.0E–8 or less Full Length sequences: Probability value = 1.0E–10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. USA 85: 2444–2448; Pearson, W. R. (1990) Methods Enzymol. 183: 63–98; and Smith, T. F. and M. S. Waterman (1981) Adv. Appl. Math. 2: 482–489. | ESTs: fasta E value = 1.06E–6 Assembled ESTs: fasta Identity = 95% or greater and Match length = 200 bases or greater; fastx E value = 1.0E–8 or less Full Length sequences: Probability value = 1.0E–3 or less |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S. and J. G. Henikoff (1991) Nucleic Acids Res. 19: 6565–6572; Henikoff, J. G. and S. Henikoff (1996) Methods Enzymol. 266: 88–105; and Attwood, T. K. et al. (1997) J. Chem. Inf. Comput. Sci. 37: 417–424. | |
| HMMER | An algorithm for searching a query sequence against hidden Markov model (HMM)-based databases of protein family consensus sequences, such as PFAM. | Krogh, A. et al. (1994) J. Mol. Biol. 235: 1501–1531; Sonnhammer, E. L. L. et al. (1988) Nucleic Acids Res. 26: 320–322; Durbin, R. et al. (1998) Our World View, in a Nutshell, Cambridge Univ. Press, pp. 1–350. | PFAM hits: Probability value = 1.0E–3 or less Signal peptide hits: Score = 0 or greater |
| ProfileScan | An algorithm that searches for structural and sequence motifs in protein sequences that match sequence patterns defined in Prosite. | Gribskov, M. et al. (1988) CABIOS 4: 61–66; Gribskov, M. et al. (1989) Methods Enzymol. 183: 146–159; Bairoch, A. et al. (1997) Nucleic Acids Res. 25: 217–221. | Normalized quality score ≧ GCG-specified "HIGH" value |

TABLE 7-continued

| Program | Description | Reference | Parameter Threshold |
|---|---|---|---|
| | | | for that particular Prosite motif. Generally, score = 1.4–2.1. |
| Phred | A base-calling algorithm that examines automated sequencer traces with high sensitivity and probability. | Ewing, B. et al. (1998) Genome Res. 8: 175–185; Ewing, B. and P. Green (1998) Genome Res. 8: 186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482–489; Smith, T.F. and M.S. Waterman (1981) J. Mol. Biol. 147: 195–197; and Green, P., University of Washington, Seattle, WA. | Score = 120 or greater; Match length = 56 or greater |
| Consed | A graphical tool for viewing and editing Phrap assemblies. | Gordon, D. et al. (1998) Genome Res. 8: 195–202. | |
| SPScan | A weight matrix analysis program that scans protein sequences for the presence of secretory signal peptides. | Nielson, H. et al. (1997) Protein Engineering 10: 1–6; Claverie, J.M. and S. Audic (1997) CABIOS 12: 431–439. | Score = 3.5 or greater |
| TMAP | A program that uses weight matrices to delineate transmembrane segments on protein sequences and determine orientation. | Persson, B. and P. Argos (1994) J. Mol. Biol. 237: 182–192; Persson, B. and P. Argos (1996) Protein Sci. 5: 363–371. | |
| TMHMMER | A program that uses a hidden Markov model (HMM) to delineate transmembrane segments on protein sequences and determine orientation. | Sonnhammer, E. L. et al. (1998) Proc. Sixth Intl. Conf. on Intelligent Systems for Mol. Biol., Glasgow et al., eds., The Am. Assoc. for Artificial Intelligence Press, Menlo Park, CA, pp. 175–182. | |
| Motifs | A program that searches amino acid sequences for patterns that matched those defined in Prosite. | Bairoch, A. et al. (1997) Nucleic Acids Res. 25: 217–221; Wisconsin Package Program Manual, version 9, page M51–59, Genetics Computer Group, Madison, WI. | |

What is claimed is:

1. An isolated polynucleotide encoding (a) a polypeptide comprising the amino acid sequence depicted in SEQ ID NO: 1, (b) a biologically active fragment of the polypeptide that consists of the amino acid sequence depicted in SEQ ID NO: 1, wherein the fragment has cysteine protease activity, or (c) a polypeptide that has at least 95% sequence identity to the amino acid sequence depicted in SEQ ID NO: 1 and has cysteine protease activity.

2. The isolated polynucleotide of claim 1, wherein the isolated polynucleotide comprises the nucleic acid sequence depicted in SEQ ID NO. 18.

3. A recombinant polynucleotide comprising a promoter sequence operably linked to the polynucleotide of claim 1.

4. A cell transformed with the recombinant polynucleotide of claim 3.

5. A method of producing a polypeptide encoded by the polynucleotide of claim 1 comprising: a) culturing a cell, which has been transformed with a recombinant polynucleotide that comprises a promoter operably linked to the polynucleotide of claim 1, under conditions suitable for expression of the polypeptide, and b) recovering the expressed polypeptide.

6. The method of claim 5, wherein the polypeptide comprises the amino acid sequence of SEQ ID NO. 1.

7. An isolated polynucleotide selected from the group consisting of: (a) a polynucleotide comprising the nucleic acid sequence depicted in SEQ ID NO. 18, (b) a polynucleotide comprising a nucleic acid sequence that has at least 95% sequence identity to the nucleic acid sequence depicted in SEQ ID NO. 18, wherein the polynucleotide encodes a polypeptide that has cysteine protease activity, c) a polynucleotide complementary to the polynucleotide of (a), (d) a polynucleotide complementary to the polynucleotide of (b), and (e) an RNA equivalent of (a)–(d).

* * * * *